(12) United States Patent
Simon et al.

(10) Patent No.: US 10,556,931 B2
(45) Date of Patent: Feb. 11, 2020

(54) BROAD SPECTRUM CONJUGATE VACCINE TO PREVENT KLEBSIELLA PNEUMONIAE AND PSEUDOMONAS AERUGINOSA INFECTIONS

(71) Applicants: Raphael Simon, Baltimore, MD (US); Alan Cross, Chevy Chase, MD (US); Sharon Tennant, Baltimore, MD (US)

(72) Inventors: Raphael Simon, Baltimore, MD (US); Alan Cross, Chevy Chase, MD (US); Sharon Tennant, Baltimore, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

(21) Appl. No.: 15/842,068

(22) Filed: Dec. 14, 2017

(65) Prior Publication Data
US 2018/0194812 A1 Jul. 12, 2018

Related U.S. Application Data

(62) Division of application No. 15/509,041, filed as application No. PCT/US2015/051032 on Sep. 18, 2015, now Pat. No. 9,988,426.

(60) Provisional application No. 62/052,256, filed on Sep. 18, 2014.

(51) Int. Cl.

| | |
|---|---|
| *A61K 39/02* | (2006.01) |
| *C07K 14/21* | (2006.01) |
| *A61K 39/104* | (2006.01) |
| *C07K 14/26* | (2006.01) |
| *A61K 39/108* | (2006.01) |
| *A61K 47/64* | (2017.01) |
| *A61K 39/00* | (2006.01) |
| *A61K 47/61* | (2017.01) |

(52) U.S. Cl.
CPC .......... *C07K 14/26* (2013.01); *A61K 39/0266* (2013.01); *A61K 39/104* (2013.01); *C07K 14/21* (2013.01); *A61K 47/61* (2017.08); *A61K 47/646* (2017.08); *A61K 2039/70* (2013.01)

(58) Field of Classification Search
None
See application file for complete search history.

(56) References Cited

U.S. PATENT DOCUMENTS

| | | | |
|---|---|---|---|
| 5,153,312 A | 10/1992 | Porro | |
| 5,739,313 A | 4/1998 | Collins | |
| 9,988,426 B2 * | 6/2018 | Simon | A61K 39/104 |

OTHER PUBLICATIONS

Trautmann Clin Diagn Lab Immunol. 4(5):550-555 (Year: 1997).*
Edelman et al, Vaccine (Guildford Then London Then Oxford) vol. 12 Issue: 14, pp. 1288-1288. (Year: 1994).*
UniProt and Accession No. P72151. (Year: 2000).*
Chhibber et al., Immunoprotective potential of polysaccharide-tetanus toxoid conjugate in Klebsiella pneumoniae induced lobar pneumonia in rats, Indian Journal of Experimental Biology, 43:40-45 (2005).
Weimer et al., A Fusion Protein Vaccine Containing OprF Epitope 8, Oprl, and Type A and B Flagellins Promotes Enhanced Clearance of Nonmucoid Pseudomonas aeruginosa, Infection and Immunity, 77:2356-2366 (2009).
Cryz et al., Safety and immunogenicity of a polyvalent Klebsiella capsular polysaccharide vaccine in humans, Vaccine, 4:15-20 (1986).
Huleatt et al., Vaccination with recombinant fusion proteins incorporating Toll-like receptor ligands induces rapid cellular and humoral immunity, Vaccine, 25:763-775 (2007).
Sefidi et al., Adjuvant role of Pseudomonas flagellin for Acinetobacter baumannii biofilm associated protein, World Journal of Methodology, 6:190-199 (2016).
Delavari et al., Pseudomonas aeruginosa flagellin as an adjuvant: superiority of a conjugated form of flagellin versus a mixture with a human immunodeficiency virus type 1 vaccine candidate in the induction of immune responses, Journal of Medical Microbiology, 64:1361-1368 (2015).
Simon et al., *Salmonella enterica* Serovar Enteritidis Core O Polysaccharide Conjugated to H:g,m Flagellin as a Candidate Vaccine for Protection against Invasive Infection with *S. Enteritidis*, Infection and Immunity, 79:4240-4249 (2011).
Simon et al., Sustained Protection in Mice Immunized with Fractional Doses of *Salmonella enteritidis* Core and 0 Polysaccharide-Flagellin Glycoconjugates, PLOS ONE, 8:e64680 (2013).
Simon et al., A scalable method for biochemical purification of *Salmonella flagellin*, Protein Expression and Purification, 102:1-7 (2014).
Gat et al., Cell-Associated Flagella Enhance the Protection Conferred by Mucosally-Administered Attenuated *Salmonella paratyphi* A Vaccines, Plos Neglected Tropical Diseases, 5:e1373 (2011).
Serushago et al., Role of Antibodies against Outer-membrane Proteins in Murine Resistance to Infection with Encapsulated Klebsiella pneumoniae, Journal of General Microbiology, 135:2259-2268 (1989).
Extended European Search Report from European Appl. No. 15841265, dated May 23, 2018.
Kunf, Comparative effects of carrier proteins on vaccine-induced immune response, Vaccine, 29:4881-4890 (2011).
Cryz et al., Synthesis and Characterization of *Escherichia coli* 0180-Polysaccharide Conjugate Vaccines, Infect Immun, 58:373-377 (1990).
Konadu et al., Preparation, Characterization, and Immunological Properties in Mice of *Escherichia coli* 0157 O-Specific Polysaccharide-Protein Conjugate Vaccines, Infect Immun, 62:5048-5054 (1994).

(Continued)

*Primary Examiner* — Padmavathi Baskar
(74) *Attorney, Agent, or Firm* — Nevrivy Patent Law Group P.L.L.C.

(57) ABSTRACT

The present invention is drawn to conjugates and vaccine compositions comprising a *Pseudomonas* flagellin or an antigenic fragment or derivative thereof linked to one or more *Klebsiella* surface polysaccharide antigens, such as *Klebsiella pneumoniae* O polysaccharide from serovars O1, O2a, O2a,c, O3, O4, O5, O7, O8 and O12. The present invention also provides serovar reagent strains to produce the conjugates and vaccine compositions and methods of inducing an immune response with the conjugates and vaccine compositions.

11 Claims, 31 Drawing Sheets

Specification includes a Sequence Listing.

(56) References Cited

OTHER PUBLICATIONS

Passwell et al., Safety and Immunogenicity of Improved Shigella O-Specific Polysaccharide-Protein Conjugate Vaccines in Adults in Israel, Infect Immun, 69:1351-1357 (2001).
Cohen et al., Double-blind vaccine-controlled randomised efficacy trial of an investigational Shigella sonnei conjugate vaccine in young adults, Lancet, 349:155-159 (1997).
Campbell et al., Immunogenicity of a 24-Valent Klebsiella Capsular Polysaccharide Vaccine and an Eight-Valent Pseudomonas O-Polysaccharide Conjugate Vaccine Administered to Victims of Acute Trauma, Clin Infect Dis, 23:179-181 (1996).
Doring et al., A double-blind randomized placebo-controlled phase III study of a Pseudomonas aeruginosa flagella vaccine in cystic fibrosis patients, Proc Natl Acad Sci, 104:11020-11025 (2007).
Brett et al., Structural and Immunological Characterization of Burkholderia pseudomallei O-Polysaccharide-Flagellin Protein Conjugates, Infect Immun, 64:2824-2828 (1996).
Ibrahim et al., Method for the Isolation of Highly Purified *Salmonella flagellins*, J Clin Microbiol, 22:1040-1044 (1985).
Darveau et al., Procedure for Isolation of Bacterial Lipopolysaccharides from Both Smooth and Rough Pseudomonas aeruginosa and *Salmonella typhimurium* strains, J. Bacteriol, 155:831-838 (1983).
Westphal et al., Bacterial Lipopolysaccharides Extraction with Phenol-Water and Further Applications of Procedure, Methods in Carbohydrate Chemistry, 5:83-91 (1965).
Tennant et al, Engineering and Preclinical Evaluation of Attenuated Nontyphoidal Salmonella Strains Serving as Live Oral Vaccines and as Reagent Strains, Infection & Immunity, 79:4175-4185 (2001).
Tomoyasu et al., The ClpXP ATP-Dependent Protease Regulates Flagellum Synthesis in *Salmonella enterica* Serovar Typhimurium, J Bacteriol, 184:645-653 (2002).
Datsenko et al., One-step inactivation of chromosomal genes in *Escherichia coli* K-12 using PCR products, PNAS USA 97:6640-6645 (2000).
Chu, Preparation, Characterization, and Immunogenicity of Conjugates Composed of the O-Specific Polysaccharide of Shigella dysenteriae Type 1 (Shiga's Bacillus) Bound to Tetanus Toxoid, Infect Immun, 59:4450-4458 (1991).
Sanders et al., Induction of adaptive immunity by flagellin does not require robust activation of innate immunity, Eur J Immunol, 39:359-371 (2009).
Turley et al., Safety and immunogenicity of a recombinant M2e-flagellin influenza vaccine (STF2.4×M2e) in healthy adults, Vaccine, 29:5145-5152 (2011).
Micoli et al., Production of a conjugate vaccine for *Salmonella enterica* serovar Typhi from Citrobacter Vi, Vaccine, 30:853-861 (2012).
Tacket et al., CVD 908, CVD 908-htrA, and CVD 909 Live Oral Typhoid Vaccines: A Logical Progression, Clin Infect Dis, 45:S20-23 (2007).
Inaba et al., Exchangeability of the Flagellin (FliC) and the Cap Protein (FliD) Among Different Species in Flagellar Assembly, Biopolymers, 99:63-72 (2013).
Kotloff et al., Safety and Immunogenicity of CVD 1208S, a Live, Oral ΔguaBA Δsen Δset Shigella flexneri 2a Vaccine Grown on Animal-Free Media, Hum Vaccine, 3:268-275 (2007).
Samant et al., Nucleotide Biosynthesis Is Critical for Growth of Bacteria in Human Blood, PLoS Pathog, 4:0001-0010 e37 (2008).
Shafer et al, Activation of soluble polysaccharides with 1-cyano-4-dimethylaminopyridinium tetrafluoroborate (CDAP) for use in protein-polysaccharide conjugate vaccines and immunological reagents. II. Selective crosslinking of proteins to CDAP-activated polysaccharides, Vaccine, 18:1273-1281 (2000).
Lees et al., Activation of soluble polysaccharides with 1-cyano-4-dimethylaminopyridinium tetrafluoroborate for use in protein-polysaccharide conjugate vaccines and immunological reagents, Vaccine, 14:190-198 (1996).
Wang et al., Construction, genotypic and phenotypic characterization, and immunogenicity of attenuated DeltaguaBA *Salmmonella enterica* serovar Typhi strain CVD 915, Infect Immun, 69:4734-4741 (2001).
Campodonico et al., Efficacy of a conjugate vaccine containing polymannuronic acid and flagellin against experimental Pseudomonas aeruginosa lung infection in mice, Infect Immun, 79:3455-3464 (2011).
Trautmann et al., Evaluation of a competitive ELISA method for the determination of Klebsiella O antigens, J Med Microbiol, 44:44-51 (1996).
International Search Report from International Application No. PCT/US2015/051032, dated Dec. 17, 2015.
Supplementary Partial European Search Report from European Appl. No. 15841265, dated Feb. 2, 2018.

\* cited by examiner

FIG 2. Transmission electron micrograph of PA strain PAK (Type A flagella) adapted from Dasgupta et al.[8]

SEQUENCE LISTING

```
<160> NUMBER OF SEQ ID NOS: 56

<210> SEQ ID NO 1
<211> LENGTH: 394
<212> TYPE: PRT
<213> ORGANISM: Pseudomonas aeruginosa

<400> SEQUENCE: 1

Met Ala Leu Thr Val Asn Thr Asn Ile Ala Ser Leu Asn Thr Gln Arg
1               5                   10                  15

Asn Leu Asn Asn Ser Ser Ala Ser Leu Asn Thr Ser Leu Gln Arg Leu
            20                  25                  30

Ser Thr Gly Ser Arg Ile Asn Ser Ala Lys Asp Asp Ala Ala Gly Leu
        35                  40                  45

Gln Ile Ala Asn Arg Leu Thr Ser Gln Val Asn Gly Leu Asn Val Ala
    50                  55                  60

Thr Lys Asn Ala Asn Asp Gly Ile Ser Leu Ala Gln Thr Ala Glu Gly
65                  70                  75                  80

Ala Leu Gln Gln Ser Thr Asn Ile Leu Gln Arg Met Arg Asp Leu Ser
                85                  90                  95

Leu Gln Ser Ala Asn Gly Ser Asn Ser Asp Ser Glu Arg Thr Ala Leu
            100                 105                 110

Asn Gly Glu Val Lys Gln Leu Gln Lys Glu Leu Asp Arg Ile Ser Asn
        115                 120                 125

Thr Thr Thr Phe Gly Gly Arg Lys Leu Leu Asp Gly Ser Phe Gly Val
    130                 135                 140

Ala Ser Phe Gln Val Gly Ser Ala Ala Asn Glu Ile Ile Ser Val Gly
145                 150                 155                 160

Ile Asp Glu Met Ser Ala Glu Ser Leu Asn Gly Thr Tyr Phe Lys Ala
                165                 170                 175

Asp Gly Gly Gly Ala Val Thr Ala Ala Thr Ala Ser Gly Thr Val Asp
            180                 185                 190

Ile Ala Ile Gly Ile Thr Gly Gly Ser Ala Val Asn Val Lys Val Asp
        195                 200                 205
```

```
Met Lys Gly Asn Glu Thr Ala Glu Gln Ala Ala Lys Ile Ala Ala
    210                 215                 220

Ala Val Asn Asp Ala Asn Val Gly Ile Gly Ala Phe Ser Asp Gly Asp
225                 230                 235                 240

Thr Ile Ser Tyr Val Ser Lys Ala Gly Lys Asp Gly Ser Gly Ala Ile
                245                 250                 255

Thr Ser Ala Val Ser Gly Val Val Ile Ala Asp Thr Gly Ser Thr Gly
                260                 265                 270

Val Gly Thr Ala Ala Gly Val Ala Pro Ser Ala Thr Ala Phe Ala Lys
                275                 280                 285

Thr Asn Asp Thr Val Ala Lys Ile Asp Ile Ser Thr Ala Lys Gly Ala
290                 295                 300

Gln Ser Ala Val Leu Val Ile Asp Glu Ala Ile Lys Gln Ile Asp Ala
305                 310                 315                 320

Gln Arg Ala Asp Leu Gly Ala Val Gln Asn Arg Phe Asp Asn Thr Ile
                325                 330                 335

Asn Asn Leu Lys Asn Ile Gly Glu Asn Val Ser Ala Ala Arg Gly Arg
                340                 345                 350

Ile Glu Asp Thr Asp Phe Ala Ala Glu Thr Ala Asn Leu Thr Lys Asn
                355                 360                 365

Gln Val Leu Gln Gln Ala Gly Thr Ala Ile Leu Ala Gln Ala Asn Gln
370                 375                 380

Leu Pro Gln Ser Val Leu Ser Leu Arg
385                 390

<210> SEQ ID NO 2
<211> LENGTH: 488
<212> TYPE: PRT
<213> ORGANISM: Pseudomonas aeruginosa

<400> SEQUENCE: 2

Met Ala Leu Thr Val Asn Thr Asn Ile Ala Ser Leu Asn Thr Gln Arg
1               5                   10                  15

Asn Leu Asn Ala Ser Ser Asn Asp Leu Asn Thr Ser Leu Gln Arg Leu
                20                  25                  30

Thr Thr Gly Tyr Arg Ile Asn Ser Ala Lys Asp Asp Ala Ala Gly Leu
            35                  40                  45

Gln Ile Ser Asn Arg Leu Ser Asn Gln Ile Ser Gly Leu Asn Val Ala
        50                  55                  60

Thr Arg Asn Ala Asn Asp Gly Ile Ser Leu Ala Gln Thr Ala Glu Gly
65                  70                  75                  80

Ala Leu Gln Gln Ser Thr Asn Ile Leu Gln Arg Ile Arg Asp Leu Ala
                85                  90                  95

Leu Gln Ser Ala Asn Gly Ser Asn Ser Asp Ala Asp Arg Ala Ala Leu
            100                 105                 110

Gln Lys Glu Val Ala Ala Gln Gln Ala Glu Leu Thr Arg Ile Ser Asp
        115                 120                 125

Thr Thr Thr Phe Gly Gly Arg Lys Leu Leu Asp Gly Ser Phe Gly Thr
130                 135                 140

Thr Ser Phe Gln Val Gly Ser Asn Ala Tyr Glu Thr Ile Asp Ile Ser
145                 150                 155                 160

Leu Gln Asn Ala Ser Ala Ser Ala Ile Gly Ser Tyr Gln Val Gly Ser
                165                 170                 175

Asn Gly Ala Gly Thr Val Ala Ser Val Ala Gly Thr Ala Thr Ala Ser
```

```
            180                 185                 190
Gly Ile Ala Ser Gly Thr Val Asn Leu Val Gly Gly Gln Val Lys
        195                 200                 205
Asn Ile Ala Ile Ala Ala Gly Asp Ser Ala Lys Ala Ile Ala Glu Lys
        210                 215                 220
Met Asp Gly Ala Ile Pro Asn Leu Ser Ala Arg Ala Arg Thr Val Phe
225                 230                 235                 240
Thr Ala Asp Val Ser Gly Val Thr Gly Gly Ser Leu Asn Phe Asp Val
                245                 250                 255
Thr Val Gly Ser Asn Thr Val Ser Leu Ala Gly Val Thr Ser Thr Gln
                260                 265                 270
Asp Leu Ala Asp Gln Leu Asn Ser Asn Ser Lys Leu Gly Ile Thr
        275                 280                 285
Ala Ser Ile Asn Asp Lys Gly Val Leu Thr Ile Thr Ser Ala Thr Gly
        290                 295                 300
Glu Asn Val Lys Phe Gly Ala Gln Thr Gly Thr Ala Thr Ala Gly Gln
305                 310                 315                 320
Val Ala Val Lys Val Gln Gly Ser Asp Gly Lys Phe Glu Ala Ala Ala
                325                 330                 335
Lys Asn Val Val Ala Ala Gly Thr Ala Ala Thr Thr Ile Val Thr
                340                 345                 350
Gly Tyr Val Gln Leu Asn Ser Pro Thr Ala Tyr Ser Val Ser Gly Thr
        355                 360                 365
Gly Thr Gln Ala Ser Gln Val Phe Gly Asn Ala Ser Ala Ala Gln Lys
        370                 375                 380
Ser Ser Val Ala Ser Val Asp Ile Ser Thr Ala Asp Gly Ala Gln Asn
385                 390                 395                 400
Ala Ile Ala Val Val Asp Asn Ala Leu Ala Ala Ile Asp Ala Gln Arg
                405                 410                 415
Ala Asp Leu Gly Ala Val Gln Asn Arg Phe Lys Asn Thr Ile Asp Asn
        420                 425                 430
Leu Thr Asn Ile Ser Glu Asn Ala Thr Asn Ala Arg Ser Arg Ile Lys
        435                 440                 445
Asp Thr Asp Phe Ala Ala Glu Thr Ala Ala Leu Ser Lys Asn Gln Val
        450                 455                 460
Leu Gln Gln Ala Gly Thr Ala Ile Leu Ala Gln Ala Asn Gln Leu Pro
465                 470                 475                 480
Gln Ala Val Leu Ser Leu Leu Arg
                485

<210> SEQ ID NO 3
<211> LENGTH: 1185
<212> TYPE: DNA
<213> ORGANISM: Pseudomonas aeruginosa

<400> SEQUENCE: 3
atggccttga ccgtcaacac caacatcgct tcgctgaaca ctcagcggaa cctgaacaac    60
tcttccgcgt cgctgaacac ttcgctgcag cgtctgtcca ccggttcgcg catcaacagc   120
gccaaggacg acgccgccgg cctgcagatc gccaaccgtc tgaccagcca ggtcaacggc   180
ctgaacgtgg ctaccaagaa cgccaacgac ggtatctccc tggcgcagac cgctgaaggc   240
gccctgcagc agtcgaccaa catcctgcag cgtatgcgtg acctgtccct gcagtcggcc   300
aacggctcca acagcgactc cgagcgtacc gctctgaacg gcgaagtgaa gcaactgcag   360
```

| | |
|---|---|
| aaagaactgg atcgtatcag caacaccacc accttcggtg gccgcaagct gctcgacggt | 420 |
| tccttcggcg tcgccagctt ccaggtgggt tcggccgcca acgaaatcat cagcgtcggc | 480 |
| atcgacgaga tgagcgcaga gtcgctgaac ggcacctact tcaaggctga cggcggcggc | 540 |
| gcggtcactg ctgcaaccgc ttcgggcacc gtcgacatcg cgatcggcat caccggcggc | 600 |
| agcgccgtga acgtcaaggt cgacatgaag ggcaacgaaa ccgccgagca ggcggctgcc | 660 |
| aagatcgccg cagcggtcaa cgacgccaac gtcggcatcg gtgccttcag cgacggcgat | 720 |
| accatcagct atgtttccaa agctggcaag gatggctccg gtgcgatcac tagcgcggtt | 780 |
| tccggcgttg tcatcgctga caccggcagc accggcgtag gcaccgcggc tggcgtagcc | 840 |
| ccttccgcta ccgctttcgc caagaccaac gacaccgtcg ccaagatcga catctccacc | 900 |
| gcgaagggcg ctcagtccgc cgtgctggtg atcgacgagg cgatcaagca gatcgacgcc | 960 |
| cagcgtgccg acctcggtgc ggtgcagaac cgcttcgaca acaccatcaa caacctgaag | 1020 |
| aacatcggtg agaacgtatc ggctgctcgc ggccggatcg aagacaccga cttcgcagcc | 1080 |
| gaaaccgcca acctgaccaa gaaccaagtg ctgcaacaag ccggcaccgc gatcctggcc | 1140 |
| caggccaacc agctgccgca gtcggttctg agcctgctgc gctaa | 1185 |

<210> SEQ ID NO 4
<211> LENGTH: 1467
<212> TYPE: DNA
<213> ORGANISM: Pseudomonas aeruginosa

<400> SEQUENCE: 4

| | |
|---|---|
| atggccctta cagtcaacac gaacattgct tccctgaaca ctcagcgcaa cctgaatgct | 60 |
| tcttccaacg acctcaacac ctcgttgcag cgtctgacca ccggctaccg catcaacagt | 120 |
| gccaaggacg atgctgccgg cctgcagatc tccaaccgcc tgtccaacca gatcagcggt | 180 |
| ctgaacgttg ccacccgcaa cgccaacgac ggcatctccc tggcgcagac cgctgaaggt | 240 |
| gccctgcagc agtccaccaa tatcctgcag cgtatccgcg acctggccct gcaatccgcc | 300 |
| aacggctcca acagcgacgc cgaccgtgcc gccctgcaga agaagtcgc tgcgcaacag | 360 |
| gccgaactga cccgtatctc cgataccacc accttcggtg gccgcaagct gctcgacggc | 420 |
| tccttcggca ccaccagctt ccaggtcggt tccaacgcct acgagaccat tgacatcagc | 480 |
| ctgcagaatg cctctgccag cgccatcggt tcttaccagg tcggcagcaa cggcgcgggt | 540 |
| accgtcgcca gcgtagcggg caccgcgacc gcttcgggca tcgcctcggg caccgtcaac | 600 |
| ctggtcggtg gcggtcaggt gaagaacatc gccatcgccg ccggcgatag cgccaaggcc | 660 |
| atcgccgaga agatggacgg tgcgatcccg aacctgtcgg ctcgtgcccg taccgtgttc | 720 |
| accgctgatg tcagcggcgt gaccggtggt tcgctgaact tcgacgtaac cgttggcagc | 780 |
| aacaccgtga gcctggcagg cgtgacctcc actcaggatc tggccgacca actgaactcc | 840 |
| aactcgtcga gctgggcat cactgccagc atcaacgaca agggtgtact gaccatcacc | 900 |
| tccgctaccg gcgagaacgt caagttcggt gcgcagaccg gtaccgctac tgccggtcag | 960 |
| gtcgcagtga aggtccaggg ttccgacggc aagttcgaag cggccgccaa gaacgtggta | 1020 |
| gctgccggta ctgccgctac caccaccatc gtgaccggct acgtgcaact gaactcgccg | 1080 |
| accgcctact cggtcagcgg taccggcacc caggcttcgc aggtcttcgg caacgccagc | 1140 |
| gccgcagaca gagcagcgt tgccagcgtc gacatctcca ctgccgacgg cgcccagaac | 1200 |
| gccatcgcgg tagtcgataa cgccctggct gcgatcgacg cccagcgtgc tgacctcggt | 1260 |
| gctgttcaga accgcttcaa gaacactatc gacaacctga ccaacatctc ggaaaacgct | 1320 |

```
accaacgctc gtagccgcat caaggacacc gacttcgctg ccgaaaccgc ggcgctgtcg    1380
aagaaccagg tgctgcaaca ggccggtacc gcgatcctgg cccaggccaa ccagctgccg    1440
caggcggtcc tgagcctgct gcgctaa                                        1467

<210> SEQ ID NO 5
<211> LENGTH: 1578
<212> TYPE: DNA
<213> ORGANISM: Klebsiella pneumoniae

<400> SEQUENCE: 5
atgacggaaa acattcataa acatcgcatc ctcatcctcg acttcgggtc tcagtatact      60
cagctggtgg cgcgtcgcgt gcgtgagctg ggcgtctact gtgagctgtg ggcatgggat     120
gtcacggaag cacagatccg cgaatttaat ccaagcggca tcattctttc cggcggcccg     180
gaaagcacca ccgaagagaa cagcccgcgc gcgccgcagt atgtgttcga agccggcgtg     240
ccggtatttg gcgtctgcta cggcatgcag accatggcga tgcagctggg cggccatgta     300
gaaggttcta acgagcgtga gtttggttac gcgcaggttg aagtggttaa cgacagcgcg     360
ctggtgcgcg gtatcgaaga ttccctgacc gcagacggca aaccgctgct ggacgtgtgg     420
atgagccacg gcgacaaagt gaccgccatc ccggcggact tcgtgaccgt cgccagcacc     480
gacaactgcc cgttcgccat tatggccaac gaagaaaaac gcttctacgg cgtgcagttc     540
cacccggaag tgacccacac ccgtcaggga atgcgtatgc tggagcgctt cgtgcgcgac     600
atctgccagt gcgaagcgct gtggacccccg gcgaaaatca ttgacgacgc cgttgagcgt     660
atccgtcagc aggttggcga cgacaaagtg atcctcggtc tctccggcgg tgtggactct     720
tcggtgaccg cgatgctgct gcaccgcgct atcggcaaaa acctgacctg tgtattcgtg     780
gacaacggtc tgctgcgcct gaacgaagcg cagcaggtga tggagatgtt cggcgaccac     840
tttggtctga acattgttca cgttgaaggc gagcagcgtt cctcgacgc gctggcgggt     900 gaaagcgatc cggaagcgaa gcgtaaaatt atcggtcgcg ttttcgtgga agtgttcgac     960
gaagaagcgc tgaagctgga cgacgtcaaa tggctggcgc agggtaccat ctaccctgac    1020
gttatcgagt ctgccgcttc cgccaccggt aaagcgcacg tcatcaaatc tcaccacaac    1080
gtgggcggcc tgccgaaaga gatgaagatg gcctggttga gccgctgcg tgagctgttt    1140 aaagacgaag tgcgtaagat cggcctggaa ctgggcctgc cgtacgacat gctctaccgt    1200
cacccgttcc cgggccccgg ccttggcgtg cgcgtgctgg gcgaagtgaa gaaagagtac    1260
tgcgacctgc tgcgtcgtgc ggacgctatc ttcatcgaag agctgcacaa agctgacctg    1320
tataacaaag tcagccaggc gttcactgtg ttcctgccgg ttcgttccgt cggcgtgatg    1380
ggcgatggcc gtaaatacga ctgggtggtt ccctgcgtg cggtggaaac catcgacttc    1440
atgaccgcgc actgggcaca cctgccgtac gatttcctcg gccgcgtctc caaccgtatc    1500
atcaatgaag tgaacggtat ctcccgcgtg gtgtatgaca tcagcggcaa gccgccagca    1560
acgattgagt gggagtaa                                                   1578

<210> SEQ ID NO 6
<211> LENGTH: 1467
<212> TYPE: DNA
<213> ORGANISM: Klebsiella pneumoniae

<400> SEQUENCE: 6
atgctacgta tcgctaaaga agccctgacg tttgacgacg tcctcctcgt tcccgctcat      60
```

| | |
|---|---|
| tctaccgttc tgccgaatac tgccgatctc agcactcagc tgacgaaaac cattcgtctg | 120 |
| aatattccta tgctctccgc agccatggat accgtaacgg aagcgcgtct ggctattgcc | 180 |
| ctggcacagg aaggcggcat cggctttatt cacaaaaaca tgtccatcga gcgccaggcg | 240 |
| gaagaagttc gtcgcgtgaa gaaacatgag tccggcgtgg tcaccgaccc gcagactgtt | 300 |
| ctgccgacga ccactctgcg tgaagtgaaa gagctgaccg agcgcaacgg tttcgccggc | 360 |
| tacccggtgg ttaccgaaga aaacgagctg gtcggcatca tcaccggccg cgacgtgcgt | 420 |
| ttcgtcaccg atctgaacca gccggtcagc gtctacatga cgccgaaaga gcgtctggtc | 480 |
| accgttcgtg aaggcgaaag ccgtgaagtg gtcttcgcta agatgcacga aaaacgcgtt | 540 |
| gagaaagcgc tggtcgtgga tgagagcttc cacctgcgcg gcatgatcac cgtcaaagac | 600 |
| ttccagaaag cagaacgtaa accgaacgcc tgtaaagatg agcagggccg tctgcgcgta | 660 |
| ggcgcggcgg tcggcgccgg tgccggcaac gaagagcgcg tagacgcgtt ggtagcggca | 720 |
| ggcgttgacg ttctgctgat cgactcctcg cacggtcact cagaaggcgt tctgcagcgt | 780 |
| atccgtgaaa cgcgcgcgaa atatcctgac ctgcagatca tcggcggcaa cgtcgccact | 840 |
| ggcgcaggcg cacgcgcgct ggcggaagcc ggctgcagcg cggtgaaagt gggcatcggc | 900 |
| ccgggctcca tctgtactac ccgtatcgtc accggcgtgg gtgtgccgca gatcaccgct | 960 |
| gtttccgacg cggtggaagc gctggaaggg accggtattc cggttatcgc tgacggcggt | 1020 |
| atccgtttct ccggcgatat cgccaaagcg atcgccgccg gtgcggcggc ggtgatggtt | 1080 |
| ggctccatgc tggcgggtac cgaagagtcc ccgggtgaaa tcgaactcta tcagggccgt | 1140 |
| tcttacaaat cttaccgcgg catgggctct cttggcgcga tgtctaaagg ctcctctgac | 1200 |
| cgctacttcc agagcgataa cgccgctgac aaactggtgc cggaaggtat cgaaggtcgc | 1260 |
| gtggcctata aaggccgcct gaaagagatc attcaccagc agatgggcgg tctgcgttcc | 1320 |
| tgtatgggtc tgaccggctg tggtaccatt gacctgctgc gtaccaaagc tgaattcgta | 1380 |
| cgcatcagcg gtgcgggcat tcaggaaagc cacgttcacg acgtgaccat caccaaagag | 1440 |
| tccccgaact accgtctggg ctcctga | 1467 |

<210> SEQ ID NO 7
<211> LENGTH: 1134
<212> TYPE: DNA
<213> ORGANISM: Klebsiella pneumoniae

<400> SEQUENCE: 7

| | |
|---|---|
| atgaagaaaa aacttgttag attttcggca ttagcgttag cgattgggtt tttatcgggt | 60 |
| tgtacaatca tccctggtca gggattaaac agtctgcgca agaacgtggt tgagcttcca | 120 |
| gacagcgact acgatctgga taagttagtg aacgtgtatc caatgacccc aggactgatc | 180 |
| gatcagcttc gtccggagac tgtactcgct cgtccaaacc cgcagcttga taatttactg | 240 |
| cgcaattatg aataccgcat tgggggttggt gacgtactga tggttaccgt atgggaccac | 300 |
| cctgaactaa ctactcctgc aggccaatac cgcagcgcca gcgatactgg taactgggtt | 360 |
| aactccgatg gtaccatttt ttatccttat attggtaagg tgcaggtagc gggaaaaact | 420 |
| ctcgctcagg tacgacagga tatagcgagc cgtttaacca cctatattga agcccacagg | 480 |
| ttgatgtta gtgttgctgc ttttcgttcg caaaaagcct atgtgacagg tgaggttact | 540 |
| aaatcagggc agcagccaat taccaatatt ccattaacgg tgatggatgc cattaacgcg | 600 |
| gccggcgggg ttgcaccaga tgcggactgg cggaatgttg tattaacaca taacgggaaa | 660 |
| gacacaaaag tctcattgta tgcattaatg cagaaaggcg atttgacaca aaatcatctg | 720 |

| | |
|---|---|
| ttatatccag gtgatattct ctttgtgccg cgtaatgacg atctaaaagt atttgtcatg | 780 |
| ggcgaagtag gtaagcaaag cacaatgaag atggatagaa gtggcatgac attggcggaa | 840 |
| gctctgggta acgctgaggg gatgtcacaa gctttcagtg atgctactgg ggtgtttgtc | 900 |
| attcgtcaga ttaaaaatga tagtcagggt aaaattgcga atatctatca gcttaatgct | 960 |
| caggatgctt cggccatggt gttaggtaca gagttccagt tacagccgta tgatattgtt | 1020 |
| tatgtcacta cagctccatt ggttcgttgg aatagagtta tatctcaact tgtgccaact | 1080 |
| attacgggag ttcatgatat gacagaaaca ggtaaattca ttcggacttg gtga | 1134 |

<210> SEQ ID NO 8
<211> LENGTH: 444
<212> TYPE: DNA
<213> ORGANISM: Klebsiella pneumoniae

<400> SEQUENCE: 8

| | |
|---|---|
| gtgatagaaa tgtttgattc aattcttgtg gtttgcacag gtaatatatg ccgctctccg | 60 |
| attggagagc gatatttacg aaacttatta cctgataaaa aaatcgattc agcagggact | 120 |
| ggagcactta ttgagcatgc ggctgataat agtgcgatta aggttgctca gctccatggg | 180 |
| cttttctttgg aggggcacct ctccaggcag tttacatcct ctcttgggcg tcaatacgat | 240 |
| ttgatattag caatggaaaa atcccatatt gagcagatcg ggcatatagc accagaagcc | 300 |
| aggggggaaaa cgatgctatt tggtcactgg ttggagcaac gcgatatacc tgacccttat | 360 |
| cgcaaaagtg acgaagcctt cttatcagtt tataaactta ttgagcaggc cggtagactt | 420 |
| tgggctcaga aattaggtgc ataa | 444 |

<210> SEQ ID NO 9
<211> LENGTH: 2163
<212> TYPE: DNA
<213> ORGANISM: Klebsiella pneumoniae

<400> SEQUENCE: 9

| | |
|---|---|
| atgtcatcag ttacaaacaa agctacatct aaagatgcgg atgaaattga tttaggtcgc | 60 |
| cttattggtg agtttataga tcatcgcaag cttattattt ctgttacttc tctattcaca | 120 |
| ttagtcgcat taatttatgc tattttttgcc acgcctatat atcaagctga tgctctaatt | 180 |
| caggttgaac agaaacaagc gaatgccata cttagcaatc ttagccagat gcttccggat | 240 |
| agccaacctc aatcggcccc agaaattgcg ttgattcgtt cccggatgat tttaggaaaa | 300 |
| acagttgatg atcttaacct gcaggcgagg gtaaaacaaa aatacttccc actattaggg | 360 |
| cgtggttttg cacgcttatc gggagataaa cctggtagtc tatctatttc tcggttgtat | 420 |
| ataccggaaa atgataatga tactcctgag atcatactaa ctgttaaaga gagaaatagt | 480 |
| ttttctatct ccgtaggtga ctttattatc aatggtaaag ttggagagct acttgatgag | 540 |
| cggggaattt cgctcaaagt tgatgaaatc agcgcaaaac cagggactga gttttcaatt | 600 |
| gtctatgtta gtcgattgaa ggctataaca gatcttcagg acgatatagc cgtagctgat | 660 |
| cagggaaaag atactgggat gctaacactc tccttgaccg gcgataatcc agtattaatt | 720 |
| gaacgtattc ttaatagcat tagtgaaaac tatttagctc agaatattgc acggcaagcc | 780 |
| gcacaagacg cgaaaagtct ggagtttttg agtaagcaac taccccaggt tcgtagtgat | 840 |
| ttggatcagg ccgaagataa attaaaccaa tatcggagaa agagtgattc cgttgattta | 900 |
| tctcttgagg caaaagccgt tcttgatcaa atagttaatg tcgataatca gcttaacgaa | 960 |

```
ttaactttc gtgagtcaga gatatcccag ctctatacca aggaacatcc tacgtataaa      1020
gcattgatgg aaaaaagaaa gactctacaa gatgaaaaag ctaagcttaa taagcgcgtt      1080
tctgctatgc ctgaaacgca gcaggaaata ttgcgtttaa gtcgtgatgt agaatctggt      1140
cgtgctgtat atatgcaatt attaaaccgg cagcaagagt taaatattgc taaatccagt      1200
gccattggta atgtgcggat tattgataat gccgtcactc aacctaaacc tgttaaaccg      1260
aaaaaagtat ttattgttct ttcagggatt atattcggta ttgtgttctc tgcaggaatt      1320
gtactactta gagttttctt gcgtagagga atagaaaccc ccgagcagct tgaagaactt      1380
ggtattaatg tctatgcaag tatcccagta gcagaaaaat ttacgaaaag tgtggtgcag      1440
agaaaagggt ggaataaaaa gtctgttgat gaaattcagg gcttcctggc agttgataac      1500
ccagcggatc tggcaattga agctatccgc agtttgcgca ccagtctcca tttcgccatg      1560
atggaggcaa gaaataatgt gctaatgatt tctggtgcaa gccctaatgc agggaaaacc      1620
tttgtaagtt cgaacttagc cgcagtgatt tctcagacag ggaaaaaagt attgtttatt      1680
gataccgata tgcgcaaagg ctatacgcat aagttgttca atgaaagcaa taccaatggc      1740
ctgtctgata ttctgtcagg taaaattgaa attaataaag caataaaaac gatcacatca      1800
gctggttttg attatatttc acgaggaatg gctccaccaa acccagctga attattaatg      1860
cacaggcgtt ttggtgaact gctgaattgg gccagtgaaa actacgatat tgttgttctc      1920
gatactccac cgatattagc cgtcacggat gcagcagtaa ttggtaatta tgcgggaaca      1980
acattaatgg ttgcccgatt tgagctgaat acggcgaaag aaatagaggt cggtattaaa      2040
cgcttcgagc aaactggtgt agtcgtaaaa ggttgcattc ttaatggtgt tgttaaaaaa      2100
gcaagtagtt attatggtta tggatataac cactatggtt attcctacaa ggataacaaa      2160
taa                                                                    2163

<210> SEQ ID NO 10
<211> LENGTH: 1578
<212> TYPE: DNA
<213> ORGANISM: Salmonella enterica

<400> SEQUENCE: 10
atgacggaaa acattcataa gcatcgcatc ctcattctgg acttcggttc tcagtacact        60
caactggttg cgcgccgcgt gcgtgagctg ggtgtttact gtgaactgtg ggcgtgggat       120
gtgacagaag cacaaattcg tgacttcaac ccaagcggca ttattctttc cggcggcccg       180
gaaagcacca ccgaagaaaa cagcccgcgc gcgccgcagt atgtctttga agcaggcgtg       240
ccggtatttg gcgtttgcta tggtatgcag accatggcga tgcagcttgg cggtcatgta       300
gaaggttcta atgagcgtga atttggttat gcgcaggtcg aagtgttgac cgacagcgcg       360
ctggttcgcg gtattgaaga ttccctgacc gcagacggca aaccgctgct ggacgtgtgg       420
atgagccacg gcgataaagt gacggcgatt ccgtccgact tcgtgaccgt cgccagcacc       480
gagagctgcc cgttcgccat tatggccaac gaagaaaaac gcttctacgg cgtacagttc       540
cacccggaag tgactcacac ccgccagggt atgcgcatgc tggagcgttt tgtacgcgat       600
atctgccagt gtgaagcgtt gtggacgccg gcgaagatca tcgatgacgc cgtggcgcgc       660
attcgcgagc aggtaggcga cgataaagtg atcctcggtc tctccggcgg cgtggattct       720
tccgtcaccg ccatgctgct gcaccgcgcg atcggtaaaa atctgacctg tgttttcgtc       780
gacaacggcc tgttgcgcct gaacgaagcc gagcaggtga tggacatgtt tggcgaccat       840
tttggtctga acattgttca cgtaccggca gaagatcgct tcctgtccgc gctggctggt       900
```

```
gagaacgatc cggaagccaa gcgtaagatc atcggccgcg ttttcgttga agtgttcgac    960
gaagaagcgc tgaaactgga agacgtgaaa tggctggcgc agggcaccat ctaccctgac   1020
gttatcgaat ctgcggcgtc tgcaaccggt aaagcgcacg tcatcaaatc tcaccacaat   1080
gtcggcggcc tgccgaaaga gatgaagatg gggctggttg aaccgctgaa agagctgttc   1140
aaagacgaag tgcgtaagat tggtctggag ctgggcctgc cgtacgacat gctgtatcgc   1200
catccgttcc gggggccggg cctcggcgtg cgcgtactgg gcgaagtgaa gaagagtac    1260 tgcgacctgc tgcgtcgcgc ggacgctatc ttcattgaag agctgcgcaa agcggatctg   1320
tacgacaaag tcagtcaggc gtttaccgtc ttcctgccgg tccgttccgt aggcgtgatg   1380
ggcgatggtc gtaagtacga ttgggttgtc tctctgcgtg ctgtcgaaac catcgacttt   1440
atgaccgcac actgggcaca tctgccgtat gatttcctgg gtcgtgtttc caaccgcatc   1500
atcaatgaag tcaacgggat tcccgtgtg gtgtatgaca tcagcggtaa accaccagct   1560
accattgagt gggaataa                                                 1578

<210> SEQ ID NO 11
<211> LENGTH: 1578
<212> TYPE: DNA
<213> ORGANISM: Salmonella enterica

<400> SEQUENCE: 11
atgacggaaa acattcataa gcatcgcatc ctcattctgg acttcggttc tcagtacact     60
caactggttg cgcgccgcgt gcgtgagctg ggtgtttact gtgaactgtg ggcgtgggat    120
gtgacagaag cacaaattcg tgacttcaac ccaagcggca ttattctttc cggcggcccg    180
gaaagcacca ccgaagaaaa cagcccgcgc gcgctgcagt atgtctttga agcaggcgtg    240
ccggtatttg gcgtttgcta tggtatgcag accatggcga tgcagcttgg cggtcatgta    300
gaaggttcta atgagcgtga atttggttat cgcgcaggtcg aagtgttgac cgacagcgcg    360
ctggttcgcg gtattgaaga ttccctgacc gcagacggca aaccgctgct ggacgtgtgg    420
atgagccacg gcgataaagt gacggcgatt ccgtccgact tcgtgaccgt cgccagcacc    480
gagagctgcc cgttcgccat tatggccaac gaagaaaaac gcttctacgg tgtacagttc    540
cacccggaag tgactcacac ccgccagggt atgcgcatgc tggagcgttt tgtacgcgat    600
atctgccagt gtgaagcgtt gtggacgccg gcgaagatca tcgacgacgc cgtggcgcgc    660
attcgcgagc aggtgggcga cgacaaagtg atcctcggcc tctctggtgg cgtggattct    720
tccgtcaccg caatgctgct gcaccgcgcg atcggtaaaa atctgacctg tgtattcgtc    780
gacaacggcc tgctgcgtct caacgaagcc gagcaggtga tggacatgtt tggcgaccat    840
tttggcctga atatcgttca cgtaccggca gaagagcgct tcctgtccgc gctggctggc    900
gagaacgatc cggaagccaa gcgtaagatc atcggtcgtg ttttgtaga agtgttcgac    960 gaagaagcgc tcaaactgga agacgtgaag tggctggcgc aaggcaccat ttaccctgac   1020
gttatcgaat ctgcggcgtc tgcaaccggt aaagcgcacg tcatcaaatc tcaccacaat   1080
gtcggcggct tgccgaaaga gatgaagatg gggctggttg aaccgctgaa agagctgttc   1140
aaagacgaag tgcgtaagat tggtctggag ctgggcctgc cgtacgacat gctgtatcgc   1200
catccgttcc gggggccggg cctcggcgtt cgtgttctgg gtgaagtgaa gaagagtac    1260 tgcgacctgc tgcgccgtgc tgacgctatc ttcattgaag agctgcgcaa agcggatctg   1320
tacgacaaag tcagtcaggc gtttaccgtc ttcctgccgg ttcgttccgt tggcgttatg   1380
```

| | |
|---|---|
| ggcgatggtc gtaagtatga ctgggttgtc tctctgcgtg ccgtcgaaac catcgacttt | 1440 |
| atgaccgcac actgggcgca cctgccgtat gacttcctcg gtcgcgtttc caaccgcatc | 1500 |
| atcaatgaag tcaacgggat ttcccgtgtg gtgtatgaca tcagcggtaa accgccggct | 1560 |
| accattgagt gggaataa | 1578 |

<210> SEQ ID NO 12
<211> LENGTH: 1578
<212> TYPE: DNA
<213> ORGANISM: Salmonella enterica

<400> SEQUENCE: 12

| | |
|---|---|
| atgacggaaa acattcataa gcatcgcatc ctcattctgg acttcggttc tcagtacact | 60 |
| caactggttg cgcgccgcgt gcgtgagctg ggtgtttact gcgaactgtg ggcgtgggat | 120 |
| gtgacagaag cacaaattcg tgacttcaac ccaagcggca ttattctttc cggcggcccg | 180 |
| gaaagcacca ccgaagaaaa cagcccgcgc gcgccgcagt atgtctttga agcaggcgtg | 240 |
| ccggtatttg gcgtctgcta cgggatgcag accatggcga tgcagcttgg cggtcatgta | 300 |
| gaaggttcta atgagcgtga atttggttac gcgcaggtcg aagtgctgac cgacagcgcg | 360 |
| ctggttcgcg gtattgaaga ttccctgacc gccgacggca accgctgct ggacgtgtgg | 420 |
| atgagccacg gcgataaagt gacggcgatt ccgtccgact tcgtgaccgt agccagcacc | 480 |
| gaaagctgcc cgttcgccat catggctaac gaagaaaaac gcttctacgg cgtacagttc | 540 |
| cacccggaag tgactcacac ccgccagggt atgcgcatgc tggagcgttt tgtgcgtgat | 600 |
| atctgccagt gtgaagccct gtggacgccg gcgaagatca tcgacgacgc cgtggcgcgc | 660 |
| attcgcgagc aggtaggcga cgataaagtg atcctcggtc tctccggcgg cgtggattct | 720 |
| tccgtaaccg caatgctgct gcaccgcgcg atcggtaaaa atctgacctg tgtattcgtc | 780 |
| gacaacggcc tgctgcgtct caacgaagcc gagcaggtga tggacatgtt tggcgaccat | 840 |
| tttggtctga acatcgttca cgtaccggca gaagatcgct tcctgtccgc gttggctggc | 900 |
| gaaaacgatc cggaagcgaa gcgtaagatc attggccgtg ttttttgtgga agtgttcgac | 960 |
| gaagaagcgt tgaaactgga agacgtgaaa tggctggcgc agggcaccat ctaccctgac | 1020 |
| gtcatcgaat ctgcggcgtc tgcaaccggt aaagcgcacg tcatcaaatc tcaccacaat | 1080 |
| gttggcggcc tgccgaaaga gatgaagatg gggctggttg aaccgctgaa agagctgttc | 1140 |
| aaagacgaag tgcgtaagat tggtctggag ctgggcctgc cgtacgacat gctgtaccgt | 1200 |
| catccgttcc cggggccggg cctcggcgta cgtgtactgg gtgaagtgaa gaaagagtac | 1260 |
| tgcgacctgc tgcgccgtgc tgatgccatc ttcattgaag agctgcgtaa ggcggatctg | 1320 |
| tacgacaaag tcagccaggc gttcaccgtc ttccctgccag tacgctccgt tggcgtaatg | 1380 |
| ggcgatggtc gtaagtacga ttgggtggtc tctctgcgtg ctgtcgaaac catcgacttt | 1440 |
| atgaccgcgc actgggcgca cctgccgtat gacttcctgg tcgtgtttc caaccgcatc | 1500 |
| atcaatgaag tcaacgggat ttcccgtgtg gtgtatgaca tcagcggtaa accaccggct | 1560 |
| accattgagt gggaataa | 1578 |

<210> SEQ ID NO 13
<211> LENGTH: 1578
<212> TYPE: DNA
<213> ORGANISM: Salmonella enterica

<400> SEQUENCE: 13

| | |
|---|---|
| atgacggaaa acattcataa gcatcgcatc ctcattctgg acttcggttc tcagtacact | 60 |

```
caactggttg cgcgccgcgt gcgtgagctg ggtgtttact gcgaactgtg ggcgtgggat      120
gtgacagaag cacaaattcg tgacttcaac ccaagcggca ttattctttc cggcggcccg      180
gaaagcacca ccgaagaaaa cagcccgcgc gcgccgcagt atgtctttga agcaggcgtg      240
ccggtatttg gcgtttgcta tggtatgcag accatggcga tgcagcttgg cggtcatgta      300
gaaggttcta atgagcgtga atttggttat gcgcaggtcg aagtgttgac cgacagcgcg      360
ctggttcgcg gtattgaaga ttccctgacc gcagacggca aaccgctgct ggacgtgtgg      420
atgagccacg gcgataaagt gacggcgatt ccgtccgact tcgtgaccgt cgccagcacc      480
gagagctgcc cgttcgccat catggctaac gaagaaaaac gcttctacgg cgtacagttc      540
cacccggaag tgacccacac ccgccagggg atgcgcatgc tggagcgttt tgtgcgtgat      600
atctgccagt gtgaagcgtt gtggacgccg gcgaagatca tcgacgacgc cgtggcgcgc      660
attcgcgagc aggtaggcga cgataaagtg atcctcggtc tctccggcgg cgtggattct      720
tccgtcaccg caatgctgct gcaccgcgcg atcggtaaaa atctgacctg tgtattcgtc      780
gacaacggcc tgctgcgtct caacgaagcc gagcaggtga tggacatgtt tggcgaccat      840
tttggcctga atatcgttca cgttccggcg gaagagcgct tcctgtccgc gttggctggc      900
gaaaacgatc cggaagcgaa gcgtaagatc attggccgtg tttttgtgga agtgttcgac      960
gaagaagcgt tgaaactgga agacgtgaaa tggctggcgc agggcaccat ctaccctgac     1020
gtcatcgagt ctgcggcgtc tgcaaccggt aaagcgcacg tcatcaaatc tcaccacaat     1080
gttggcggcc tgccgaaaga gatgaagatg gggctggttg aaccgctgaa agagctgttc     1140
aaagacgaag tgcgtaagat tggtctggag ctgggcctgc cgtacgacat gctgtaccgt     1200
catccgttcc cggggccggg cctcggcgta cgtgtactgg gtgaagtgaa gaaagagtac     1260
tgcgacctgt tgcgccgtgc tgacgccatc ttcattgaag agctgcgtaa ggcggatctg     1320
tacgacaaag tcagccaggc gttcaccgtc ttcctgccag tacgctccgt tggcgtaatg     1380
ggcgatggtc gtaagtacga ttgggtggtc tccctgcgtg ctgtcgaaac catcgacttt     1440
atgactgcgc actgggcgca tctgccgtat gacttcctgg tcgtgtttc caaccgcatc     1500 atcaatgaag tcaacgggat ttcccgtgtg gtgtatgaca tcagcggtaa accaccggct     1560
accattgagt gggaataa                                                   1578
```

<210> SEQ ID NO 14  
<211> LENGTH: 1578  
<212> TYPE: DNA  
<213> ORGANISM: Salmonella enterica

<400> SEQUENCE: 14

```
atgacggaaa acattcataa gcatcgcatc ctcattctgg acttcggttc tcagtacact       60
caactggttg cgcgccgcgt gcgtgagctg ggtgtttact gcgaactgtg ggcgtgggat      120
gtgacagaag cacaaattcg tgacttcaac ccaagcggca ttattctttc cggcggcccg      180
gaaagcacca ccgaagaaaa cagcccgcgc gcgccgcagt atgtctttga agcaggcgtg      240
ccggtatttg gcgtttgcta tggtatgcag accatggcga tgcagcttgg cggtcatgta      300
gaaggttcta atgagcgtga atttggttat gcgcaggtcg aagtgttgac cgacagcgcg      360
ctggttcgcg gtattgaaga ttccctgact gcagacggca aaccgctgct ggacgtgtgg      420
atgagccacg gcgataaagt gacggcgatt ccgtccgact tcgtgaccgt cgccagcacc      480
gagagctgcc cgttcgccat tatggccaac gaagaaaaac gcttctacgg tgtacagttc      540
```

```
cacccggaag tgactcacac ccgccagggt atgcgcatgc tggagcgttt tgtacgcgat    600
atctgccagt gtgaagccct gtggacgccg gcgaagatca tcgacgacgc cgtggcgcgc    660
attcgcgagc aggtgggcga cgacaaagtg atcctcggtc tctccggcgg cgtggattct    720
tccgtcaccg cgatgctgct gcaccgcgcc atcggtaaaa atctgacctg tgttttcgtc    780
gacaacggcc tgttgcgcct gaacgaagcc gagcaggtga tggacatgtt tggcgaccat    840
tttggcctga atatcgttca cgtaccggca gaagagcgct tcctgtccgc gctggctggc    900
gagaacgatc cggaagccaa gcgtaagatc atcggtcgtg tttttgtaga agtgttcgac    960
gaagaagcgc tcaaactgga agacgtgaag tggctggcgc aaggcaccat ttaccctgac   1020
gttatcgaat ctgcggcgtc tgcaaccggt aaagcgcacg tcatcaaatc tcaccacaat   1080
gtcggcggct tgccgaaaga gatgaagatg gggctggttg aaccgctgaa agagctgttc   1140
aaagacgaag tgcgtaagat tggtctggag ctgggcctgc cgtatgacat gctgtatcgc   1200
catccgttcc cggggccggg cctcggcgtt cgtgttctgg gtgaagtgaa gaaagagtac   1260
tgcgacctgc tgcgccgtgc tgacgctatc ttcattgaag agctgcgcaa agcggatctg   1320
tacgacaaag tcagtcaggc gtttaccgtc ttcctgccgg ttcgttccgt tggcgttatg   1380
ggcgatggtc gtaagtatga ctgggttgtc tctctgcgtg ccgtcgaaac catcgacttt   1440
atgaccgcac actgggcgca cctgccgtat gacttcctcg gtcgcgtttc caaccgcatc   1500
atcaatgaag tcaacgggat ttcccgtgtg gtgtatgaca tcagcggtaa accgccggct   1560
accattgagt gggaataa                                                 1578

<210> SEQ ID NO 15
<211> LENGTH: 1467
<212> TYPE: DNA
<213> ORGANISM: Salmonella enterica

<400> SEQUENCE: 15
atgctacgta tcgctaaaga agctctgacg tttgacgacg tcctccttgt tcccgctcac     60
tccaccgttt tgccgaatac tgccgatctc agcacgcagt tgacgaaaac tattcgtctg    120
aatattccta tgcttttctgc ggcgatggac accgtgacgg aagcgcgcct ggcaattgcc    180
ctggcccagg aaggcggcat tggttttatc cacaaaaaca tgtctattga gcgccaggcg    240
gaagaagttc gccgcgtgaa gaaacacgag tccggcgtag tgaccgaccc gcagaccgtc    300
ctgccaacca ccacgttgca tgaagtgaaa gccctgaccg agcgtaacgg ttttgcgggc    360
tatccggtgg tgactgaaga taacgagctg gtgggtatca tcaccggtcg tgacgtgcgt    420
tttgtgactg acctgaacca gccggtgagt gtctacatga caccgaaaga gcgtctggtg    480
accgttcgtg aaggcgaagc ccgtgaagtc gtgctggcaa aaatgcacga aaaacgcgta    540
gaaaaagcgc tggtcgttga tgataacttc catctgcttg gcatgattac cgtaaaagat    600
ttccagaaag cggaacgtaa accaaactcc tgtaaagatg agcagggccg tttacgtgtc    660
ggcgcggcgg tcgcgcaggc gcgggcaac gaagagcgcg ttgacgcgct ggtggcggca    720
ggcgttgacg tactgctgat cgactcctct cacggtcact ctgaaggcgt gttgcaacgt    780
atccgtgaga cgcgtgctaa atatcctgac ctgcaaatca tcggcggcaa cgttgcgacg    840
ggcgcaggcg ctcgcgcact ggcggaagcc ggttgcagcg cggtgaaagt gggtatcggc    900 ccggggttcca tctgtacgac tcgtatcgtg actggtgtgg gcgttccgca gatcaccgct    960
gtttctgacg cggtggaagc gctggaaggc accgggattc cggttatcgc tgacggcggt   1020 atccgttttct ccggcgacat cgccaaagcc atcgccgcag gcgcgagcgc ggtaatggtg   1080
```

```
ggttctatgc tggccggtac cgaagaatcc ccgggcgaaa tcgaactcta ccagggccgt    1140
tcttacaaat cttatcgcgg tatgggttct ctgggcgcga tgtccaaagg ttcctccgac    1200
cgttacttcc agagcgacaa cgccgccgac aaactggtgc cggaaggtat cgaaggccgc    1260
gtagcctata aaggtcgcct gaaagagatc attcaccagc agatgggcgg cctgcgctcc    1320
tgtatggggc tgaccggttg tgctaccatc gacgaactgc gtactaaagc ggagtttgtg    1380
cgtatcagcg gtgcgggtat ccaggaaagc cacgttcacg acgtgaccat caccaaagag    1440
tccccgaact accgtctggg ctcctga                                       1467
```

```
<210> SEQ ID NO 16
<211> LENGTH: 1467
<212> TYPE: DNA
<213> ORGANISM: Salmonella enterica

<400> SEQUENCE: 16
```

```
atgctacgta tcgctaaaga agccctgacg tttgacgacg tcctccttgt tcccgctcac      60
tccaccgttt tgccgaatac tgccgatctc agcacgcagt tgacgaaaac tattcgtctg     120
aatattccta tgctttctgc ggcgatggac accgtgacgg aagcgcgcct ggcaattgcc     180
ctggcccagg aaggcggcat tggttttatc cacaaaaaca tgtccattga cgccaggcg      240 gaagaagttc gccgcgtgaa gaaacacgag tccggcgtag tgaccgaccc gcagaccgtc     300
ctgccaacca ccacgttgca tgaagtgaaa gccctgaccg agcgtaacgg ttttgcgggc     360
tatccggtgg tgactgaaga taacgagctg gtgggtatca tcaccggtcg tgacgtgcgt     420
tttgtgactg acctgaacca gccggttagc gtttacatga cgccgaaaga gcgtctggtg     480
accgttcgtg aaggcgaagc ccgtgaagtc gtgctggcaa aaatgcacga aaaacgcgta     540
gaaaaagcgc tggtcgttga tgataacttc catctgcttg gcatgattac cgtaaaagat     600
ttccagaaag cggaacgtaa accaaactcc tgcaaagatg agcagggccg tttacgtgtc     660
ggcgcggcgg tcggcgcagg cgcgggcaac gaagagcgcg ttgacgcgct ggtggcggca     720
ggcgttgacg tactgctgat cgactcctct cacggtcatt cagaaggcgt gttgcaacgt     780
atccgtgaaa cccgtgctaa atatcctgac ctgcaaatca tcggcggcaa cgtcgcgaca     840
ggcgcaggcg ctcgcgcact ggcggaagcc ggttgcagcg cggtgaaagt cggtattggc     900
ccgggttcca tctgtaccac tcgtatcgtg actggcgtgg cgttccgca gatcaccgct     960 gtttctgacg cagttgaagc gctggaaggt accggtattc cggttatcgc tgacggcggt     1020
atccgtttct ccggcgacat agccaaagcg attgccgcag gtgcaagcgc ggtaatggtg     1080
ggttccatgc tggcgggtac ggaagaatcc ccgggcgaaa tcgaactcta ccagggccgt     1140
tcttacaaat cttaccgcgg catgggctcg ctgggtgcga tgtccaaagg ttcctccgac     1200
cgttacttcc agagcgacaa cgccgctgac aaactggtgc cggaaggtat cgaaggtcgc     1260
gtagcctata aggtcgcct gaaagagatc attcaccagc agatgggcgg cctgcgctcc     1320
tgtatggggc tgaccggttg tgctaccatc gacgaactgc gtactaaagc ggagtttgtg     1380
cgtatcagcg gtgcgggcat tcaggaaagc cacgttcacg acgtgaccat caccaaagag     1440
tccccgaact accgtctggg ctcctga                                        1467
```

```
<210> SEQ ID NO 17
<211> LENGTH: 1467
<212> TYPE: DNA
<213> ORGANISM: Salmonella enterica
```

<400> SEQUENCE: 17

```
atgctacgta tcgctaaaga agccctgacg tttgacgacg tcctccttgt tcccgctcac      60
tccaccgttt tgccgaatac tgccgatctc agcacgcagt tgacgaaaac tattcgtctg     120
aatattccta tgctttctgc ggcgatggac accgtgacgg aagcgcgcct ggcaattgcc     180
ctggcccagg aaggcggcat tggttttatc acaaaaaaca tgtccattga cgccaggcg      240
gaagaagttc gccgcgtgaa gaaacacgag tccggcgtag tgaccgaccc gcagaccgtc     300
ctgccaacca ccacgttgca tgaagtgaaa gccctgaccg agcgtaacgg ttttgcgggc     360
tatccggtgg tgactgaaga taacgagctg gtggggatca tcaccggtcg tgacgtgcgt     420
tttgtgactg acctgaacca gccggtaagt gtctacatga cgccgaaaga gcgtctggtg     480
accgttcgtg aaggcgaagc ccgtgaagtc gtgctggcaa aaatgcacga aaaacgcgta     540
gaaaagcgc tggtcgttga tgataacttc catctgcttg gcatgattac cgtaaaagat      600
ttccagaaag cggaacgtaa accaaactcc tgtaaagatg agcagggccg tttacgtgtc     660
ggcgcggcgg tcgcgcagg cgcgggcaac gaagagcgcg ttgacgcgct ggtggcggca     720
ggcgttgacg tactgctgat cgactcctct cacggtcact ctgaaggcgt gttgcaacgt     780
atccgtgaga cgcgtgctaa atatcctgac ctgcaaatca tcggcggcaa cgttgcgacg     840
ggcgcaggcg ctcgcgcact ggcggaagcc ggttgcagcg cggtgaaagt gggtatcggc     900
ccgggctcca tctgtaccac tcgtatcgtg actggtgtgg cgttccgca gatcaccgct      960
gtttccgacg cggtagaagc gctggaaggc accggaattc cggttatcgc tgacggcggt    1020
atccgttct ccggcgacat cgccaaagcc atcgccgcag cgcgagcgc cgtgatggtg      1080
ggctctatgc tggccggtac cgaagaatcc ccggcgaaa tcgaactcta ccagggccgt     1140
tcgtacaaat cttaccgcgg catgggctcg ctggcgcga tgtccaaagg ttcctccgac     1200
cgttacttcc agagcgacaa cgccgctgac aaactggtgc cggaaggtat cgaaggccgc    1260
gtagcctata aggtcgcct gaaagagatc attcaccagc agatgggcgg cctgcgctcc     1320
tgtatggggc tgaccggttg tgctaccatc gacgaactgc gtactaaagc ggagtttgtg    1380
cgtatcagcg gtgcgggtat ccaggaaagc cacgttcacg acgtgaccat caccaaagag    1440
tccccgaact accgtctggg ctcctga                                         1467
```

<210> SEQ ID NO 18
<211> LENGTH: 624
<212> TYPE: DNA
<213> ORGANISM: Salmonella enterica

<400> SEQUENCE: 18

```
atgtcataca gcggagaacg agataatttg gcccctcata tggcgctggt gccgatggtc      60
attgaacaga cctcacgcgg tgagcgctct tttgatatct attctcgtct acttaaggaa     120
cgcgtcatat ttctgaccgg ccaggtcgaa gaccatatgg ctaacctgat cgtgcgcag      180
atgctgttcc tggaagcgga aaacccggaa aaagatatct atctgtacat taattctcct     240
ggcggcgtaa ttactgcggg gatgtccatc tatgacacca tgcagtttat taagccagac     300
gtcagcacca tttgtatggg acaggcggcc tctatggggg cgtttctgct gactgccggg     360
gcgaaaggca aacgtttctg cttgccgaac tctcgcgtca tgatccacca gccgctgggc     420
ggctaccagg ccaggcgac ggatattgaa attcacgccc gcgaaatttt gaaagtaaaa      480
gggcgcatga atgaacttat ggcgcatcat acgggtcaat ctcttgagca gattgaacgt     540
gatactgagc gcgatcgctt cctctccgcg cctgaagcgg tagagtacgg tttggttgac     600
```
tcaattttga cccatcgtaa ttga                                            624

<210> SEQ ID NO 19
<211> LENGTH: 624
<212> TYPE: DNA
<213> ORGANISM: Salmonella enterica

<400> SEQUENCE: 19
atgtcataca gcggagaacg agataaattg gccctcata tggcgctggt gccgatggtc        60
attgaacaga cctcacgcgg tgagcgctct tttgatatct attctcgtct acttaaggaa      120
cgcgtcatat ttctgaccgg ccaggtcgaa gaccatatgg ctaacctgat cgtggcgcag      180
atgctgttcc tggaagcgga aaacccggaa aaagatatct atctgtacat taattctcct      240
ggcggcgtaa ttactgcggg gatgtccatc tatgacacca tgcagtttat taagccagac      300
gtcagcacca tttgtatggg acaggcggcc tctatggggg cgtttctgct gactgccggg      360
gcgaaaggca aacgtttctg cttgccgaac tctcgcgtca tgatccacca gccgctgggc      420
ggctaccagg gccaggcgac ggatattgaa attcacgccc gcgaaatttt gaaagtaaaa      480
gggcgcatga atgaacttat ggcgcatcat acgggtcaat ctcttgagca gattgaacgt      540
gatactgagc gcgatcgctt cctctccgcg cctgaagcgg tagagtacgg tttggttgac      600
tcaattttga cccatcgtaa ttga                                            624

<210> SEQ ID NO 20
<211> LENGTH: 624
<212> TYPE: DNA
<213> ORGANISM: Salmonella enterica

<400> SEQUENCE: 20
atgtcataca gcggagaacg agataaattg gccctcata tggcgctggt gccgatggtc        60
attgaacaga cctcacgcgg tgagcgctct tttgatatct attctcgtct acttaaggaa      120
cgcgtcatat ttctgaccgg ccaggtcgaa gaccatatgg ctaacctgat cgtggcgcag      180
atgctgttcc tggaagcgga aaacccggaa aaagatatct atctgtacat taattctcct      240
ggcggcgtaa ttactgcggg gatctccatc tatgacacca tgcagtttat taagccagac      300
gtcagcacca tttgtatggg acaggcggcc tctatggggg cgtttctgct gactgccggg      360
gcgaaaggca aacgtttctg cttgccgaac tctcgcgtca tgatccacca gccgctgggc      420
ggctaccagg gccaggcgac ggatattgaa attcacgccc gcgaaatttt gaaagtaaaa      480
gggcgcatga atgaacttat ggcgcatcat acgggtcaat ctcttgagca gattgaacgt      540
gatactgagc gcgatcgctt cctctccgcg cctgaagcgg tagagtacgg tttggttgac      600
tcaattttga cccatcgtaa ttga                                            624

<210> SEQ ID NO 21
<211> LENGTH: 1272
<212> TYPE: DNA
<213> ORGANISM: Salmonella enterica

<400> SEQUENCE: 21
atgacagata aacgcaaaga tggctcgggc aaattgttgt actgctcttt ttgcggcaaa        60
agccagcatg aagtgcgcaa gctgattgcc ggtccatccg tgtatatctg cgacgaatgc      120
gtcgatttat gtaacgacat tattcgcgaa gaaattaaag aagttgctcc gcaccgtgaa      180
cgtagtgcgc tgccgacgcc gcatgaaatt cgtacccacc tggacgatta cgttatcggc      240

| | |
|---|---|
| caggagcagg cgaaaaaagt gctggcgctg gcggtctata accactacaa gcgtctgcgt | 300 |
| aacggcgata ccagcaatgg cgtcgagtta ggtaaaagca acattctgct gattggaccg | 360 |
| accggttccg gtaaaacgct gctggcggaa acgctggcgc gcttgctgga tgtgccgttc | 420 |
| actatggcgg atgcgaccac gctaaccgaa gcgggttacg ttggtgaaga cgtcgagaat | 480 |
| atcattcaga aactgttgca gaaatgcgac tacgacgtgc aaaaagcgca gcgtgggatt | 540 |
| gtctacattg atgaaatcga taagatttcg cgtaaatcag acaatccgtc cattacccgc | 600 |
| gatgtttccg gcgaaggcgt acagcaggcg ttgctgaaac tgatcgaagg caccgtcgcc | 660 |
| gcggttccac cgcagggcgg tcgcaaacat ccgcagcagg agttcttaca ggtagatacc | 720 |
| tctaagattc tgtttatctg cggcggcgcg tttgccggtc tggataaagt gatcgctaac | 780 |
| cgtgttgaaa ccggctccgg cattggtttt ggcgcgacgg tgaaagcgaa gtccgacaaa | 840 |
| gccagcgaag gcgagctgtt gtcgcaggtt gaaccggaag atttgatcaa atttggtctg | 900 |
| attcctgagt ttatcggtcg tctgccagtg gtagcgacgc tgaatgaact cagcgaagaa | 960 |
| gcgctgattc aaatcctgaa agagccgaaa aatgcgctga ccaagcagta tcaggcgctg | 1020 |
| tttaacctgg aaggcgtcga tctggaattc cgtgacgaag cgctggacgc tatcgccagg | 1080 |
| aaagcaatgg cgcgtaaaac cggcgcccgt ggcctgcgtt ctatcgtcga agcggcgctg | 1140 |
| ctggatacca tgtacgattt gccatctatg gaagacgtcg aaaaagtggt gatcgacgag | 1200 |
| tccgttattg ccggtcagag taagccgttg ctgatttacg gcaaaccgga agcgcaggct | 1260 |
| tctggcgaat aa | 1272 |

<210> SEQ ID NO 22
<211> LENGTH: 1272
<212> TYPE: DNA
<213> ORGANISM: Salmonella enterica

<400> SEQUENCE: 22

| | |
|---|---|
| atgacagata aacgcaaaga tggctcgggc aaattgttgt actgctcttt ttgcggcaaa | 60 |
| agccagcatg aagtgcgcaa gctgattgcc ggtccatccg tgtatatctg cgacgaatgc | 120 |
| gtcgatttat gtaacgacat tattcgcgaa gaaattaaag aagttgctcc gcaccgtgaa | 180 |
| cgtagtgcgc tgccgacgcc gcatgaaatt cgtacccacc tggacgatta cgttatcggc | 240 |
| caggagcagg cgaaaaaagt gctggcggtg gcggtctata accactacaa gcgtctgcgt | 300 |
| aacggcgata ccagcaatgg cgtcgagtta ggtaaaagca acattctgct gattggaccg | 360 |
| accggttccg gtaaaacgct gctggcggaa acgctggcgc gcttgctgga tgtgccgttc | 420 |
| actatggcgg atgcgaccac gctaaccgaa gcgggttacg ttggtgaaga cgtcgagaat | 480 |
| atcattcaga aactgttgca gaaatgcgac tacgacgtgc aaaaagcgca gcgtgggatt | 540 |
| gtctacattg atgaaatcga taagatttcg cgtaaatcag acaatccgtc cattacccgc | 600 |
| gatgtttccg gcgaaggcgt acagcaggcg ttgctgaaac tgatcgaagg caccgtcgcc | 660 |
| gcggttccac cgcagggcgg tcgcaaacat ccgcagcagg agttcttaca ggtagatacc | 720 |
| tctaagattc tgtttatctg cggcggcgcg tttgccggtc tggataaagt gatcgctaac | 780 |
| cgtgttgaaa ccggctccgg cattggtttt ggcgcgacgg tgaaagcgaa gtccgacaaa | 840 |
| gccagcgaag gcgagctgtt gtcgcaggtt gaaccggaag atttgatcaa atttggtctg | 900 |
| attcctgagt ttatcggtcg tctgccagtg gtagcgacgc tgaatgaact cagcgaagaa | 960 |
| gcgctgattc aaatcctgaa agagccgaaa aatgcgctga ccaagcagta tcaggcgctg | 1020 |
| tttaacctgg aaggcgtcga tctggaattc cgtgacgaag cgctggacgc tatcgccagg | 1080 |

```
aaagcaatgg cgcgtaaaac cggcgcccgt ggcctgcgtt ctatcgtcga agcggcgctg    1140
ctggatacca tgtacgattt gccatctatg aagacgtcg aaaaagtggt gatcgacgag    1200
tccgttattg ccggtcagag taagccgttg ctgatttacg gcaaaccgga agcgcaggct    1260
tctggcgaat aa                                                       1272

<210> SEQ ID NO 23
<211> LENGTH: 1272
<212> TYPE: DNA
<213> ORGANISM: Salmonella enterica

<400> SEQUENCE: 23
atgacagata aacgcaaaga tggctcgggc aaattgttgt actgctcttt ttgcggcaaa      60
agccagcatg aagtgcgcaa gctgattgcc ggtccatccg tgtatatctg cgacgaatgc    120
gtcgatttat gtaacgacat tattcgcgaa gaaattaaag aagttgctcc gcaccgtgaa    180
cgtagtgcgc tgccgacgcc gcatgaaatt cgtacccacc tggacgatta cgttatcggc    240
caggagcagg cgaaaaaagt gctggcggtg gcggtctata ccactacaa gcgtctgcgt     300 aacggtgata ccagcaatgg cgtcgagtta ggcaaaagca acattctgct gattggaccg    360
accggttccg gtaaaacgct gctggcggaa acgctggcgc gcttgctgga tgtgccgttc    420
actatggcgg atgcgaccac gctgaccgaa gcgggttacg tgggtgaaga cgtcgagaat    480
atcattcaga aactgttgca gaaatgcgac tacgacgtgc aaaaagcgca gcgtgggatt    540
gtctacattg atgaaatcga taagatttcg cgtaaatcag acaatccgtc cattacccgc    600
gatgtttccg gcgaaggcgt acagcaggcg ttgctgaaac tgatcgaagg caccgtcgcc    660
gcggttccac cgcagggcgg tcgcaaacat ccgcagcagg agttcttaca ggtagatacc    720
tctaagattc tgtttatctg cggcggcgcg tttgctggtc tggataaagt gatcgctaac    780
cgtgttgaaa ccggctccgg cattggtttt ggcgcgacgg tgaaagcgaa gtccgacaaa    840
gccagcgaag gcgagctgtt gtcgcaggtt gaaccggaag atttgatcaa atttggtctg    900
attcctgagt ttatcggtcg tctgccagtg gtggcgacgc tgaacgaact cagcgaagaa    960
gcgctgattc aaatcctgaa agagccgaaa aatgcgctga ccaagcagta tcaggcgctg    1020
tttaacctgg aaggcgtcga tctggaattc cgtgacgaag cgctggacgc tatcgccagg    1080
aaagcaatgg cgcgtaaaac cggtgcccgt ggtctgcgtt ctatcgtcga agcggcgctg    1140
ctggatacca tgtacgattt gccatctatg aagacgtcg aaaaagtggt gatcgacgag    1200
tccgttattg ccggtcagag taagccgttg ctgatttacg gcaaaccgga agcgcaggct    1260
tctggcgaat aa                                                       1272

<210> SEQ ID NO 24
<211> LENGTH: 1518
<212> TYPE: DNA
<213> ORGANISM: Salmonella enterica

<400> SEQUENCE: 24
atggcacaag tcattaatac aaacagcctg tcgctgttga cccagaataa cctgaacaaa     60
tctcagtcct cactgagttc cgctattgag cgtctgtcct ctggtctgcg tatcaacagc    120
gcgaaagacg atgcggcagg ccaggcgatt gctaaccgct tcacttctaa tatcaaaggt    180
ctgactcagg cttcccgtaa cgctaacgac ggcatttcta ttgcgcagac cactgaaggt    240
gcgctgaatg aaatcaacaa caacctgcag cgtgtgcgtg agttgtctgt tcaggccact    300
```

```
aacgggacta actctgattc cgatctgaaa tctatccagg atgaaattca gcaacgtctg    360
gaagaaatcg atcgcgtttc taatcagact caatttaacg gtgttaaagt cctgtctcag    420
gacaaccaga tgaaaatcca ggttggtgct aacgatggtg aaaccattac catcgatctg    480
caaaaaattg atgtgaaaag ccttggcctt gatgggttca atgttaatgg ccaaaagaa     540 gcgacagtgg gtgatctgaa atccagcttc aagaatgtta cgggttacga cacctatgca    600
gcgggtgccg ataaatatcg tgtagatatt aattccggtg ctgtagtgac tgatgcagca    660
gcaccggata agtatatgt aaatgcagca aacggtcagt taacaactga cgatgcggaa     720
aataacactg cggttgatct ctttaagacc actaaatcta ctgctggtac cgctgaagcc    780
aaagcgatag ctggtgccat aaaggtggt aaggaaggag ataccttga ttataaaggc      840 gtgacttta ctattgatac aaaaaactgg gatgacggta atggtaaggt ttctactacc     900
atcaatggtg aaaaagttac gttaactgtc gctgatattg ccactggcgc gacggatgtt    960
aatgctgcta ccttacaatc aagcaaaaat gtttatacat ctgtagtgaa cggtcagttt   1020
acttttgatg ataaaaccaa aacgagagt gcgaaacttt ctgatttgga agcaaacaat    1080
gctgttaagg gcgaaagtaa aattacagta aatgggctg aatatactgc taacgccacg    1140
ggtgataaga tcaccttagc tggcaaaacc atgtttattg ataaaacagc ttctggcgta   1200
agtacattaa tcaatgaaga cgctgccgca gccaagaaaa gtaccgctaa cccactggct   1260
tcaattgatt ctgcattgtc aaaagtggac gcagttcgtt cttctctggg ggcaattcaa   1320
aaccgttttg attcagccat taccaacctt ggcaatacgg taaccaatct gaactccgcg   1380
cgtagccgta tcgaagatgc tgactatgca acggaagttt ctaatatgtc taaagcgcag   1440
attctgcagc aggctggtac ttccgttctg gcgcaggcta accaggttcc gcaaaacgtc   1500
ctctctttac tgcgttaa                                                 1518

<210> SEQ ID NO 25
<211> LENGTH: 1488
<212> TYPE: DNA
<213> ORGANISM: Salmonella enterica

<400> SEQUENCE: 25
atggcacaag tcattaatac aaacagcctg tcgctgttga cccagaataa cctgaacaaa     60
tcccagtccg ctctgggcac cgctatcgag cgtctgtctt ccggtctgcg tatcaacagc    120
gcgaaagacg atgcggcagg tcaggcgatt gctaaccgtt ttaccgcgaa catcaaaggt    180
ctgactcagg cttcccgtaa cgctaacgac ggtatctcca ttgcgcagac cactgaaggc    240
gcgctgaacg aaatcaacaa caacctgcag cgtgtgcgtg aactggcggt tcagtctgct    300
aacagcacca actcccagtc tgacctcgac tccatccagg ctgaaatcac ccagcgcctg    360
aacgaaatcg accgtgtatc cggccagact cagttcaacg gcgtgaaagt cctggcgcag    420
gacaacaccc tgaccatcca ggttggtgcc aacgacggtg aaactatcga tatcgatctg    480
aagcagatca actctcagac cctgggtctg gatacgctga atgtgcaaca aaaatataag    540
gtcagcgata cggctgcaac tgttacagga tatgccgata ctacgattgc tttagacaat    600 agtacttta aagcctcggc tactggtctt ggtggtactg accagaaaat tgatggcgat    660
ttaaaatttg atgatacgac tggaaaatat tacgccaaag ttaccgttac gggggaact    720 ggtaaagatg ctattatga gtttccgtt gataagacga acggtgaggt gactcttgct    780
ggcggtgcga cttccccgct tacaggtgga ctacctgcga cagcaactga ggatgtgaaa   840
aatgtacaag ttgcaaatgc tgatttgaca gaggctaaag ccgcattgac agcagcaggt   900
```

```
gttaccggca cagcatctgt tgttaagatg tcttatactg ataataacgg taaaactatt        960
gatggtggtt tagcagttaa ggtaggcgat gattactatt ctgcaactca aaataaagat       1020
ggttccataa gtattaatac tacgaaatac actgcagatg acggtacatc caaaactgca       1080
ctaaacaaac tgggtggcgc agacggcaaa accgaagttg tttctattgg tggtaaaact       1140
tacgctgcaa gtaaagccga aggtcacaac tttaaagcac agcctgatct ggcggaagcg       1200
gctgctacaa ccaccgaaaa cccgctgcag aaaattgatg ctgctttggc acaggttgac       1260
acgttacgtt ctgacctggg tgcggtacag aaccgtttca actccgctat taccaacctg       1320
ggcaacaccg taaacaacct gacttctgcc cgtagccgta tcgaagattc cgactacgcg       1380
accgaagttt ccaacatgtc tcgcgcgcag attctgcagc aggccggtac ctccgttctg       1440
gcgcaggcga accaggttcc gcaaaacgtc ctctctttac tgcgttaa                    1488

<210> SEQ ID NO 26
<211> LENGTH: 1488
<212> TYPE: DNA
<213> ORGANISM: Salmonella enterica

<400> SEQUENCE: 26
atggcacaag tcattaatac aaacagcctg tcgctgttga cccagaataa cctgaacaaa        60
tcccagtccg ctctgggcac cgctatcgag cgtctgtctt ccggtctgcg tatcaacagc       120
gcgaaagacg atgcggcagg tcaggcaatt gctaaccgtt tcaccgcgaa catcaaaggt       180
ctgactcagg cttcccgtaa cgctaacgac ggtatctcca ttgcgcagac cactgaaggc       240
gcgctgaacg aaatcaacaa caacctgcag cgtgtgcgtg aactggcggt tcagtctgct       300
aacagcacca actcccagtc tgacctcgac tccatccagg ctgaaatcac ccagcgcctg       360
aacgaaatcg accgtgtatc cggtcagact cagttcaacg gcgtgaaagt cctggcgcag       420
gacaacaccc tgaccatcca ggttggtgcc aacaacggtg aaaccattga tatcgatctg       480
aaacagatca actctcagac cctgggtctg gatacgctga atgtgcagaa aaaatatgat       540
gtgaagagcg aagcggtcac gccttcggct acattaagca ctactgcact tgatggtgct       600
ggcctcaaaa ccggaaccgg ttctacaact gatactggtt caattaagga tggtaaggtt       660
tactataaca gcacctctaa aaattattat gttgaagtag aatttaccga tgcgaccgat       720
caaaccaaca aaggcggatt ctataaagtt aatgttgctg atgatggtgc agtcacaatg       780
actgcggcta ccaccaaaga ggctacaact cctacaggta ttactgaagt tactcaagtc       840
caaaaacctg tggctgctcc agctgctatc caggctcagt tgactgctgc ccatgtgacc       900
ggcgctgata ctgctgaaat ggttaagatg tcttatacgg ataaaaacgg taagactatt       960
gatgccggtt tcggtgttaa agttgggggct gatatttatg ctgcaacaaa aaataaagat      1020
ggatcgttca gcattaacac cactgaatat accgataaag acggcaacac taaaactgca      1080
ctaaaccaac tgggtggcgc agacggtaaa actgaagttg tttctatcga cggtaaaacc      1140
tacaatgcca gcaaagccgc tggtcacaac tttaaagcac agccagagct ggctgaagcg      1200
gctgctgcaa ccaccgaaaa cccgctggct aaaattgatg ccgcgctggc gcaggttgat      1260
gcgctgcgtt ctgacttggg tgcggttcag aaccgtttca actccgctat caccaacctg      1320
ggcaataccg taaataacct gtcttctgcc cgtagccgta tcgaagattc cgactacgcg      1380
accgaagttt ccaacatgtc tcgcgcgcag atcctgcagc aggccggtac ctccgttctg      1440
gcgcaggcga accaggttcc gcaaaacgtc ctctctttac tgcgttaa                    1488
```

```
<210> SEQ ID NO 27
<211> LENGTH: 20
<212> TYPE: DNA
<213> ORGANISM: Artificial Sequence
<220> FEATURE:
<223> OTHER INFORMATION: synthetic construct- primer

<400> SEQUENCE: 27
gggtagatga tcaccggcag                                               20

<210> SEQ ID NO 28
<211> LENGTH: 20
<212> TYPE: DNA
<213> ORGANISM: Artificial Sequence
<220> FEATURE:
<223> OTHER INFORMATION: synthetic construct- primer

<400> SEQUENCE: 28
tgattggtct gactggacgc                                               20

<210> SEQ ID NO 29
<211> LENGTH: 20
<212> TYPE: DNA
<213> ORGANISM: Artificial Sequence
<220> FEATURE:
<223> OTHER INFORMATION: synthetic construct- primer

<400> SEQUENCE: 29
ggaagccagt gggatctgac                                               20

<210> SEQ ID NO 30
<211> LENGTH: 20
<212> TYPE: DNA
<213> ORGANISM: Artificial Sequence
<220> FEATURE:
<223> OTHER INFORMATION: synthetic construct- primer

<400> SEQUENCE: 30
ctgatccaaa cctggcccat                                               20

<210> SEQ ID NO 31
<211> LENGTH: 40
<212> TYPE: DNA
<213> ORGANISM: Artificial Sequence
<220> FEATURE:
<223> OTHER INFORMATION: synthetic construct- primer

<400> SEQUENCE: 31
ggtcgacgga tccccggaat ggagtaatcc ccggcgttag                         40

<210> SEQ ID NO 32
<211> LENGTH: 40
<212> TYPE: DNA
<213> ORGANISM: Artificial Sequence
<220> FEATURE:
<223> OTHER INFORMATION: synthetic construct- primer

<400> SEQUENCE: 32
gaagcagctc cagcctacac gggcaatatc tcgaccaggg                         40

<210> SEQ ID NO 33
<211> LENGTH: 20
<212> TYPE: DNA
<213> ORGANISM: Artificial Sequence
<220> FEATURE:
<223> OTHER INFORMATION: synthetic construct- primer
```

```
<400> SEQUENCE: 33
catacaccac gcgggagata                                               20

<210> SEQ ID NO 34
<211> LENGTH: 44
<212> TYPE: DNA
<213> ORGANISM: Artificial Sequence
<220> FEATURE:
<223> OTHER INFORMATION: synthetic construct- primer

<400> SEQUENCE: 34
ggtcgacgga tccccggaat gctagccgcg ttttcgtgga agtg                    44

<210> SEQ ID NO 35
<211> LENGTH: 18
<212> TYPE: DNA
<213> ORGANISM: Artificial Sequence
<220> FEATURE:
<223> OTHER INFORMATION: synthetic construct- primer

<400> SEQUENCE: 35
gtcctcctcg ttcccgct                                                 18

<210> SEQ ID NO 36
<211> LENGTH: 46
<212> TYPE: DNA
<213> ORGANISM: Artificial Sequence
<220> FEATURE:
<223> OTHER INFORMATION: synthetic construct- primer

<400> SEQUENCE: 36
gaagcagctc cagcctacac gaattccatc tttacaggcg ttcggt                  46

<210> SEQ ID NO 37
<211> LENGTH: 19
<212> TYPE: DNA
<213> ORGANISM: Artificial Sequence
<220> FEATURE:
<223> OTHER INFORMATION: synthetic construct- primer

<400> SEQUENCE: 37
gagccgactc tagggtggc                                                19

<210> SEQ ID NO 38
<211> LENGTH: 51
<212> TYPE: DNA
<213> ORGANISM: Artificial Sequence
<220> FEATURE:
<223> OTHER INFORMATION: synthetic construct- primer

<400> SEQUENCE: 38
gaagcagctc cagcctacac taatgtcaca tcatcagtaa atcaaaattt g            51

<210> SEQ ID NO 39
<211> LENGTH: 52
<212> TYPE: DNA
<213> ORGANISM: Artificial Sequence
<220> FEATURE:
<223> OTHER INFORMATION: synthetic construct- primer

<400> SEQUENCE: 39
gaagcagctc cagcctacac gtaatagata tgttatagag tttggagggg ag           52

<210> SEQ ID NO 40
```

```
<211> LENGTH: 32
<212> TYPE: DNA
<213> ORGANISM: Artificial Sequence
<220> FEATURE:
<223> OTHER INFORMATION: synthetic construct- primer

<400> SEQUENCE: 40
tatttaattt ccctctttca tcctgtaatg tt                          32

<210> SEQ ID NO 41
<211> LENGTH: 52
<212> TYPE: DNA
<213> ORGANISM: Artificial Sequence
<220> FEATURE:
<223> OTHER INFORMATION: synthetic construct- primer

<400> SEQUENCE: 41
ggtcgacgga tccccggaat tgtttcaaga ttatatattt cgatgcctaa tg    52

<210> SEQ ID NO 42
<211> LENGTH: 32
<212> TYPE: DNA
<213> ORGANISM: Artificial Sequence
<220> FEATURE:
<223> OTHER INFORMATION: synthetic construct- primer

<400> SEQUENCE: 42
tccttagtat aaagttgaga gatttctgat tc                          32

<210> SEQ ID NO 43
<211> LENGTH: 52
<212> TYPE: DNA
<213> ORGANISM: Artificial Sequence
<220> FEATURE:
<223> OTHER INFORMATION: synthetic construct- primer

<400> SEQUENCE: 43
ggtcgacgga tccccggaat gaatcggatg atatcgattt aggtaaaatt gt    52

<210> SEQ ID NO 44
<211> LENGTH: 32
<212> TYPE: DNA
<213> ORGANISM: Artificial Sequence
<220> FEATURE:
<223> OTHER INFORMATION: synthetic construct- primer

<400> SEQUENCE: 44
gctaatagct ttcaaacgac ttatataggt ta                          32

<210> SEQ ID NO 45
<211> LENGTH: 20
<212> TYPE: DNA
<213> ORGANISM: Artificial Sequence
<220> FEATURE:
<223> OTHER INFORMATION: synthetic construct- primer

<400> SEQUENCE: 45
gtgtaggctg gagctgcttc                                        20

<210> SEQ ID NO 46
<211> LENGTH: 20
<212> TYPE: DNA
<213> ORGANISM: Artificial Sequence
<220> FEATURE:
<223> OTHER INFORMATION: synthetic construct- primer

<400> SEQUENCE: 46
```

```
attccgggga tccgtcgacc                                              20

<210> SEQ ID NO 47
<211> LENGTH: 32
<212> TYPE: DNA
<213> ORGANISM: Artificial Sequence
<220> FEATURE:
<223> OTHER INFORMATION: synthetic construct- primer

<400> SEQUENCE: 47
tatctaggat ccatggcctt gaccgtcaac ac                                32

<210> SEQ ID NO 48
<211> LENGTH: 31
<212> TYPE: DNA
<213> ORGANISM: Artificial Sequence
<220> FEATURE:
<223> OTHER INFORMATION: synthetic construct- primer

<400> SEQUENCE: 48
ctaagtgcta gcaagcttag cgcagcaggc t                                 31

<210> SEQ ID NO 49
<211> LENGTH: 33
<212> TYPE: DNA
<213> ORGANISM: Artificial Sequence
<220> FEATURE:
<223> OTHER INFORMATION: synthetic construct- primer

<400> SEQUENCE: 49
acttgcggat ccatggccct tacagtcaac acg                               33

<210> SEQ ID NO 50
<211> LENGTH: 30
<212> TYPE: DNA
<213> ORGANISM: Artificial Sequence
<220> FEATURE:
<223> OTHER INFORMATION: synthetic construct- primer

<400> SEQUENCE: 50
attagcgcta gccgtgagtg accgttcccg                                   30

<210> SEQ ID NO 51
<211> LENGTH: 20
<212> TYPE: DNA
<213> ORGANISM: Artificial Sequence
<220> FEATURE:
<223> OTHER INFORMATION: synthetic construct- primer

<400> SEQUENCE: 51
gtgtaggctg gagctgcttc                                              20

<210> SEQ ID NO 52
<211> LENGTH: 19
<212> TYPE: DNA
<213> ORGANISM: Artificial Sequence
<220> FEATURE:
<223> OTHER INFORMATION: synthetic construct- primer

<400> SEQUENCE: 52
catatgaata tcctcctta                                               19

<210> SEQ ID NO 53
<211> LENGTH: 19
<212> TYPE: DNA
```

```
<213> ORGANISM: Artificial Sequence
<220> FEATURE:
<223> OTHER INFORMATION: synthetic construct- primer

<400> SEQUENCE: 53
ccatgccatc ttcctttcg                                                19

<210> SEQ ID NO 54
<211> LENGTH: 47
<212> TYPE: DNA
<213> ORGANISM: Artificial Sequence
<220> FEATURE:
<223> OTHER INFORMATION: synthetic construct- primer

<400> SEQUENCE: 54
gaagcagctc cagcctacac gatcttttcc ttatcaatta caacttg                 47

<210> SEQ ID NO 55
<211> LENGTH: 37
<212> TYPE: DNA
<213> ORGANISM: Artificial Sequence
<220> FEATURE:
<223> OTHER INFORMATION: synthetic construct- primer

<400> SEQUENCE: 55
taaggaggat attcatatga tccggcgatt gattcac                            37

<210> SEQ ID NO 56
<211> LENGTH: 21
<212> TYPE: DNA
<213> ORGANISM: Artificial Sequence
<220> FEATURE:
<223> OTHER INFORMATION: synthetic construct- primer

<400> SEQUENCE: 56
tggtaattta atctccccc a                                              21
```

BROAD SPECTRUM CONJUGATE VACCINE TO PREVENT KLEBSIELLA PNEUMONIAE AND PSEUDOMONAS AERUGINOSA INFECTIONS

CROSS-REFERENCE TO RELATED APPLICATIONS

This application claims the benefit of U.S. Provisional Appl. No. 61/052,256, filed Sep. 18, 2014. The content of the aforementioned application is relied upon and is incorporated by reference in its entirety.

INCORPORATION-BY-REFERENCE OF MATERIAL SUBMITTED ELECTRONICALLY

Incorporated by reference in its entirety herein is a computer-readable sequence listing submitted concurrently herewith and identified as follows: One 58,497 Byte ASCII (Text) file named "seq listing ST25.txt," created on Sep. 18, 2015.

STATEMENT OF FEDERALLY SPONSORED RESEARCH AND DEVELOPMENT

This invention was made with government support under Grant Number W81XWH-15-2-0028 awarded by United States Army Medical Research and Material Command (USAMRMC). The government has certain rights in the invention.

FIELD OF THE INVENTION

The present invention generally relates at least to the fields of medicine, immunology, molecular biology and infectious diseases. In particular, the invention relates to novel conjugate vaccines for treating or preventing invasive blood infections, urinary tract infections, respiratory infections (including cystic fibrosis), wound infections, central nervous system infections and burn infections as well as nosocomial and community acquired infections caused by Klebsiella and Pseudomonas bacteria and septic shock.

BACKGROUND OF THE INVENTION

Klebsiella pneumoniae (KP) and Pseudomonas aeruginosa (PA) are Gram Negative Bacteria (GNB) that are among the most prevalent and virulent pathogens associated with wound infections in combat personnel. They can cause serious clinical syndromes including abscess formation, cellulitis, disseminated infection, and bacteremia leading to progressive amputation, permanent impairment and death by septic shock. The growing proportion of Klebsiella pneumoniae and PA that are multi-drug resistant (MDR) complicates treatment. Immunoprophylactic measures against PA and Klebsiella pneumoniae can be effective irrespective of the antibiotic resistance phenotypes.

Klebsiella pneumoniae can express two virulence-associated polysaccharides (PS): a secreted cell-associated capsular polysaccharide (CPS) that coats the bacterium and a lipopolysaccharide (LPS) that forms the outer leaflet of the outer-membrane. The polysaccharide portion of Klebsiella pneumoniae LPS is comprised of a genus-specific conserved core and a serotype specific polymer of O polysaccharide (OPS; FIG. 1) for which there are ~9 recognized serotypes (Vinogradov E, J Biol Chem. 2002; 277(28):25070-25081; Vinogradov E, Carbohydr Res. 2001; 335(4):291-296).

Importantly, the prevalence of OPS types among clinical isolates is highly restricted. Hospital based surveys of invasive infections have revealed that four OPS serotypes (O1, O2a, O3 and O5) account for 60-80% strains causing infections in the USA and worldwide. By comparison, there are at least 80 identified CPS serotypes of which greater than 25 are associated with invasive infections in humans in the USA (Podschun R, Clin Microbiol Rev. 1998; 11(4):589-603; Hansen D S, J Clin Microbiol. 1999; 37(1):56-62); Trautmann M, Vaccine. 2004; 22(7):818-821; Cryz S J, Jr., J Clin Microbiol. 1986; 23(4):687-690). Furthermore, the incidence and prevalence of invasive infections attributed to various CPS serotypes varies dramatically worldwide; CPS types that are prevalent in one region, can be absent entirely in others (Cryz S J, Jr., J Clin Microbiol. 1986; 23(4):687-690), including potential areas of military deployment.

Despite envelopment by CPS, evidence has accumulated that Klebsiella pneumoniae LPS is accessible to antibody. LPS expression is required for protection against the alternative pathway of the complement system (Merino S, Infect Immun. 1992; 60(6):2529-2535). Long-chain OPS polymers extend beyond the capsule surface and activate the alternative complement pathway at their distal ends, too far from the cell-surface to be functional (Tomas J M, Infect Immun. 1991; 59(6):2006-2011; Williams P, J Gen Microbiol. 1983; 129(7):2181-2191; Tomas J M, Microb Pathog. 1988; 5(2): 141-147). Selective pressure for OPS expression has been documented when KP is grown in human serum and absent when serum complement is heat-inactivated or KP is grown in broth culture (Camprubi S, Microb Pathog. 1992; 13(2): 145-155). LPS expression has also been associated with establishment of invasive infections in animal models (Lawlor M S, Mol Microbiol. 2005; 58(4):1054-1073; Hsieh P F, PLoS One. 2012; 7(3):e33155). Short-chain LPS is also likely to be antibody accessible, as several capsule types have been documented as permeable to antibody (Meno Y, Infect Immun. 1990; 58(5):1421-1428; Williams P, J Med Microbiol. 1988; 26(1):29-35); and LPS can become further exposed by thin and incomplete encapsulation.

Klebsiella pneumoniae CPS are important virulence factors that antagonize non-specific opsonophagocytic uptake and capsule-deficient Klebsiella pneumoniae are highly attenuated (Williams P, J Gen Microbiol. 1983; 129(7): 2181-2191; Domenico P, Infect Immun. 1994; 62(10):4495-4499). However, expression of CPS inhibits binding interactions by Klebsiella pneumoniae adhesins with epithelial cells, an important early step in infection; thus it is likely that CPS expression is down-regulated in the early stages of infection (Favre-Bonte S, Infect Immun. 1999; 67(2):554-561; Hennequin C, Res Microbiol. 2007; 158(4):339-347; Schembri M A, Infect Immun. 2005; 73(8):4626-4633). Numerous studies have supported the role of antibodies towards Klebsiella pneumoniae LPS in protection against invasive KP infection with encapsulated strains. Antibodies to OPS antigen induced by active immunization with purified LPS (Tomas J M, Infect Immun. 1991; 59(6):2006-2011; Clements A, Vaccine. 2008; 26(44):5649-5653; Chhibber S, Jpn J Infect Dis. 2004; 57(4):150-155), OPS:protein conjugates (Chhibber S, Indian J Exp Biol. 2005; 43(1):40-45; Chhibber S, Vaccine. 1995; 13(2):179-184), killed whole-cells (Shimoguchi K., Kansenshogaku Zasshi. 1990; 64(12): 1482-1492), acapsular mutants (Lawlor M S, Infect Immun. 2006; 74(9):5402-5407), or passive transfer with polyclonal (Clements A, Vaccine. 2008; 26(44):5649-5653) or monoclonal (Held T K, Infect Immun. 2000; 68(5):2402-2409) anti-LPS antibodies have protected against fatal Klebsiella pneumoniae pneumonic and intraperitoneal infections in rodents. Parenteral immunization with formalin inactivated whole-cell encapsulated *Klebsiella pneumoniae* has protected against infection with the homologous encapsulated strain, and remarkably negligible anti-CPS but robust anti-LPS antibody was detected, for which the level correlated well with protection (Shimoguchi K., *Kansenshogaku Zasshi*. 1990; 64(12):1482-1492). Immunization with purified O1 LPS has also elicited protection against O1 strains expressing different capsule types (Tomas J M, *Infect Immun*. 1991; 59(6):2006-2011) Anti-*Klebsiella pneumoniae* O1 OPS monoclonal antibodies have demonstrated enhanced opsonophagocytosis of encapsulated strains (Held T K, *Infect Immun*. 2000; 68(5):2402-2409), and protected against encapsulated *Klebsiella pneumoniae* when given by passive transfer (Rukavina T, *Infect Immun*. 1997; 65(5): 1754-1760). Partial protection has also been obtained by antibodies directed towards the core polysaccharide that is conserved among *Klebsiella pneumoniae*, the diminished protection relative to anti-OPS is likely due however to steric hindrance for accessibility of the core polysaccharide to antibody in the context of long-chain OPS (Chen W H, *Innate Immun*. 2008; 14(5):269-278; Mandine E, *Infect Immun*. 1990; 58(9):2828-2833).

Immune responses to *Klebsiella pneumoniae* outer membrane proteins (e.g., iron regulated proteins, porins) have also protected (Chhibber S, *Vaccine*. 1995; 13(2):179-184; Serushago B A, *J Gen Microbiol*. 1989; 135(8):2259-2268; Kurupati P, *Clin Vaccine Immunol*. January 2011; 18(1):82-88). However, evidence suggests that LPS is the superior vaccine target, as antibodies to purified OMP proteins did not protect as well as antibodies to non-encapsulated whole cell preparations that included LPS (Serushago B A, *J Gen Microbiol*. 1989; 135(8):2259-2268). Immunization with *Klebsiella pneumoniae* capsular polysaccharides have protected against burn-wound *Klebsiella pneumoniae* infections in animal models (Cryz S J, Jr., *J Infect Dis*. 1984; 150(6): 817-822), and passive transfer with anti-capsule antibodies recapitulated the protection seen with active vaccination (Cryz S J, Jr., *Infect Immun*. 1984; 45(1):139-142). As anti-LPS antibodies are protective against intraperitoneal (IP) and pneumonic *Klebsiella pneumoniae* infections in mice, they are also presumed to be protective against wound infections caused by *Klebsiella pneumoniae*.

Generating a CPS-based vaccine that would be effective against pathogenic *Klebsiella pneumoniae* strains worldwide is not easily accomplished as the manufacture and establishment of acceptable immunogenicity for all components of a ≥25 valent vaccine is a major challenge. A 24-valent *Klebsiella pneumoniae* CPS vaccine was shown to be immunogenic in human trials (Edelman R, *Vaccine*. 1994; 12(14):1288-1294). However, the levels varied dramatically among serotypes, with some inducing only poor antibody levels. Importantly, antibody levels for most *Klebsiella pneumoniae* CPS types plunged within the 18 months of follow-up to pre-immune levels (Edelman R, *Vaccine*. 1994; 12(14):1288-1294; Granstrom M, *J Clin Microbiol*. 1988; 26(11):2257-2261). Similar responses have been seen in humans to the capsular polysaccharides of other pathogens, and in certain instances (Pace D, *Vaccine*. 2009; 27 Suppl 2:B30-41; Gonzalez-Fernandez A, *Vaccine*. 17 2008; 26(3): 292-300) progressively diminished boost responses have been noted after sequential re-immunizations due to depletion of pre-committed naïve B-cells (Richmond P, *J Infect Dis*. 2000; 181(2):761-764). Polysaccharides are thymus-independent antigens that do not activate T-cells and hence generally generate only moderate antibody titers without immunologic memory, class-switching, or affinity maturation (Pollard A J, *Nat Rev Immunol*. 2009; 9(3):213-220). Furthermore, whereas some polysaccharides elicit acceptable antibody levels, other polysaccharides are not immunogenic as purified antigens. Covalent chemical linkage of bacterial polysaccharides with proteins has enhanced the magnitude, quality and duration of the induced antibody, through activation of polysaccharide-specific B-cells by protein carrier specific helper T-cells, and importantly, has generated anamnestic and booster responses. Glycoconjugate vaccines are among the most costly of all vaccine types to manufacture, however, and development of multivalent conjugate formulations with >7 components (e.g., pneumococcal CPS conjugates) have been hampered by issues of epitopic suppression and interference among individual components (Dagan R, *Vaccine*. 2010; 28(34):5513-5523).

Since antibodies to the OPS of *Klebsiella pneumoniae* are protective, and the overall number and predominance of OPS types is relatively limited, it raises the possibility that a *Klebsiella pneumoniae* OPS vaccine approach might be a more straightforward and feasible vaccine strategy for KP. Accordingly, there has been extensive investigation over the previous decades towards vaccine strategies targeting KP LPS. Vaccine formulations utilizing whole-cell killed organisms and purified LPS, however, are unacceptably reactogenic for humans, as they elicit severe adverse reactions including high fever and malaise.

The lipid A endotoxin portion of LPS is readily cleaved by chemical means, yielding isolated O polysaccharide (OPS) or a core oligosaccharide and an O polysaccharide (COPS) (Wang X, *Subcell Biochem*. 2010; 53:27-51; Simon R, *Infect Immun*. 2011; 79(10):4240-4249). As purified polysaccharide antigens, COPS molecules have generally proven entirely refractory to antibody production in animal models (Simon R, *Infect Immun*. 2011; 79(10):4240-4249; Konadu E, *Infect Immun*. 1996; 64(7):2709-2715; Watson D C, *Infect Immun*. 1992; 60(11):4679-4686). However, conjugation with carrier proteins (e.g., $CRM_{197}$, flagellins, porins, tetanus toxoid [TT]) has enhanced immunogenicity (Knuf M, *Vaccine*. 2011; 29(31):4881-4890). COPS-based conjugate vaccines have proven efficacious in animal models for several GNB pathogens (e.g., *E. coli* (Cryz S J, Jr., *Infect Immun*. 1990; 58(2):373-377; Konadu E, *Infect Immun*. 1994; 62(11):5048-5054), *V. cholerae*, P A (Cryz S J, Jr., *Infect Immun*. 1986; 52(1):161-165), *Salmonella* (Simon R, *Infect Immun*. 2011; 79(10):4240-4249; Konadu E, *Infect Immun*. 1996; 64(7):2709-2715; Watson D C, *Infect Immun*. 1992; 60(11):4679-4686; Svenson S B, *Infect Immun*. 1979; 25(3):863-872; Micoli F, *PLoS One*. 2012; 7(11):e47039), *Shigella* (Kubler-Kielb J, *Carbohydr Res*. 2010; 345(11): 1600-1608; Robbins J B, *Proc Natl Acad Sci USA*. 2009; 106(19):7974-7978; Chu C Y, *Infect Immun*. 1991; 59(12): 4450-4458)). Importantly, COPS conjugates have been well-tolerated and immunogenic in human clinical trials (Passwell J H, *Infect Immun*. 2001; 69(3):1351-1357; Cohen D, *Infect Immun*. 1996; 64(10):4074-4077; Konadu E Y, *Infect Immun*. 2000; 68(3):1529-1534; Konadu E Y, *J Infect Dis*. 1998; 177(2):383-387; Cryz S J, Jr., *J Clin Invest*. 1987; 80(1):51-56; Cryz S J, Jr., *J Infect Dis*. 1986; 154(4):682-688) and have induced functional bactericidal antibodies (Konadu E Y, *Infect Immun*. 2000; 68(3):1529-1534). Some COPS conjugates have demonstrated efficacy in controlled field trials. In a large randomized double-blind efficacy trial of a *Shigella sonnei* COPS conjugate among military recruits in Israel, significant protection was observed, for which levels of anti-*S. sonnei* LPS correlated with protection (Cohen D, *Lancet*. 1997; 349(9046):155-159). A *Pseudomonas aeruginosa* COPS-based conjugate vaccine was immunogenic when administered to acute trauma patients within 72 hours of hospitalization (Campbell W N, *Clin Infect Dis.* 1996; 23(1):179-181).

All pathogenic *Pseudomonas aeruginosa* express a single polar flagellum that extends from the cell surface (FIG. 2; adapted from Dasgupta N, *J Bacteriol.* 2000; 182(2):357-364) to enable motility, that is comprised chiefly by polymers of either type A or B flagellin proteins (Stanislaysky E S, *FEMS Microbiol Rev.* 1997; 21(3):243-277). There is a single B-type flagellin form (FlaB)(Verma A et al., *J Bacteriol.* 1998; 180(12):3209-3217), and two A-type flagellin sub-forms (FlaA) that differ in sequence by only a few amino acids and are similarly reactive with A-type specific antibodies (Brimer C D, Montie T C, *J Bacteriol.* 1998; 180(12):3209-3217; Arora S K et al., *J Bacteriol.* 2004; 186(7):2115-2122). While there have been no rigorous surveys conducted to determine the precise prevalence of strains expressing A and B type flagellin, the distribution of A and B type flagella expressing clinical isolates reported in the literature suggests that the prevalence of the two flagella types does not differ greatly (Rosok M J et al., *Infect Immun.* 1990; 58(12):3819-3828; Shanks K K et al., *Clin Vaccine Immunol.* 2010; 17(8):1196-1202).

*Pseudomonas aeruginosa* flagella are well established as virulence factors and protective antigens against *Pseudomonas aeruginosa* infections. The requirement of flagella for *Pseudomonas aeruginosa* pathogenicity is underscored by the dramatically reduced virulence observed for strains lacking flagella in mouse models of fatal *Pseudomonas aeruginosa* wound and respiratory infections (Montie T C et al., *Infect Immun.* 1982; 38(3):1296-1298; Feldman M et al., *Infect Immun.* 1998; 66(1):43-51). Several roles have been noted for flagella in *Pseudomonas aeruginosa* pathogenesis. Flagellar mediated motility is important for biofilm development, and strains lacking functional motile flagella do not establish robust biofilms in vitro and are attenuated in vivo (Klausen M et al., *Mol Microbiol.* 2003; 48(6):1511-1524; O'Toole G A et al., *Mol Microbiol.* 1998; 30(2):295-304; Arora S K et al., *Infect Immun.* 2005; 73(7):4395-4398). Accordingly, highly motile strains are extremely pathogenic in a mouse model of *Pseudomonas aeruginosa* burn infection (Craven R C et al., *Can J Microbiol.* 1981; 27(4):458-460). Flagella have also been found as attachment and colonization factors binding to mammalian epithelial cell glycans (Arora S K et al., *Infect Immun.* 1998; 66(3):1000-1007; Arora S K et al., *Infect Immun.* 1996; 64(6):2130-2136; Lu W et al., *J Immunol.* 2006; 176(7):3890-3894). Binding to mammalian Toll-like receptor 5 (TLR5) protein by *Pseudomonas* flagellin activates putative protective proinflammatory signaling pathways, however, overt inflammation due to flagellin is likely to be detrimental to the host (Balloy V et al., *J Infect Dis.* 2007; 196(2):289-296; Ben Mohamed F et al., *PLoS One.* 2012; 7(7):e39888).

Antibodies specific for *Pseudomonas aeruginosa* flagellins elicited by active immunization, or supplied by passive transfer have conferred robust protection in animal models against respiratory (Campodonico V L et al., *Infect Immun.* 2011; 79(8):3455-3464; Campodonico V L et al., *Infect Immun.* 2010; 78(2):746-755), peritonitis (Neville L F et al., *Int J Mol Med.* 2005; 16(1):165-171) or burn wound (Faezi S et al., *APMIS.* 2013; Barnea Y et al., *Burns.* 2009; 35(3):390-396; Barnea Y et al., *Plast Reconstr Surg.* 2006; 117(7):2284-2291; Holder I A et al., *J Trauma.* 1986; 26(2):118-122; Holder I A et al., *Am J Med.* 1984; 76(3A):161-167; Holder I A et al., *Infect Immun.* 1982; 35(1):276-280) *Pseudomonas aeruginosa* infections. The presumed mechanism of protection by anti-Fla antibodies is arrest of motility and enhancement of opsonophagocytic killing (Stanislaysky E S, *FEMS Microbiol Rev.* 1997; 21(3):243-277; Doring G et al., *Vaccine.* 2008; 26(8):1011-1024; Faezi S et al., *Burns.* 2011; 37(5):865-872). Protection, including for burn wound infections, has been found as specific for either A or B type flagellins (Holder I A et al., *Infect Immun.* 1982; 35(1):276-280; Montie T C et al., *Infect Immun.* 1982; 35(1):281-288). Mice immunized with bivalent preparations of type A and B flagellins purified from *Pseudomonas aeruginosa* were protected against fatal infection in the burn-sepsis model of *Pseudomonas aeruginosa* infection with both subtypes of flagellin expressing strains, indicating that a broadly protective bivalent *Pseudomonas aeruginosa* flagellin vaccine is feasible (Holder I A et al., *J Trauma.* 1986; 26(2):118-122; Holder I A et al., *Infect Immun.* 1982; 35(1):276-280). Several groups have reported robust protection against wound infections including for MDR-*Pseudomonas aeruginosa* by passive transfer of anti-flagellin polyclonal sera (Faezi S et al., *Burns.* 2011; 37(5):865-872; Drake D et al., *Can J Microbiol.* 1987; 33(9):755-763), as well as monoclonal antibodies directed against type specific FlaA and FlaB epitopes (Rosok M J et al., *Infect Immun.* 1990; 58(12):3819-3828; Barnea Y et al., *Burns.* 2009; 35(3):390-396; Barnea Y et al., *Plast Reconstr Surg.* 2006; 117(7):2284-2291; Adawi A et al., *Int J Mol Med.* 2012; 30(3):455-464). In one study, passive transfer of a monoclonal anti-FlaA produced equivalent survival against PA infection in burned mice as antibiotic (imipenem) treatment (Barnea Y et al., *Burns.* 2009; 35(3):390-396). *Pseudomonas aeruginosa* flagellin vaccines have also been investigated in human clinical trials, and were found to be well tolerated and immunogenic (Doring G et al., *Proc Natl Acad Sci USA.* 26 2007; 104(26):11020-11025; Doring G, Dorner F., *Behring Inst Mitt.* 1997; (98):338-344; Doring G et al., *Am J Respir Crit Care Med.* 1995; 151(4):983-985). A double-blind randomized Phase 3 trial in cystic fibrosis patients with a bivalent *Pseudomonas aeruginosa* A/B flagellin vaccine revealed robust and durable antibody titers, and statistically significant protection (Doring G et al., *Proc Natl Acad Sci USA.* 26 2007; 104(26): 11020-11025).

*Pseudomonas aeruginosa* flagellins are not expressed at high levels natively, and hence high yield expression systems are required to establish feasibility for large-scale production. *Pseudomonas aeruginosa* flagellins are readily expressed and purified from heterologous Gram Negative Bacteria (GNB) expression systems, including *Salmonella* and *Escherichia coli* (Campodonico V L et al., *Infect Immun.* 2011; 79(8):3455-3464; Kelly-Wintenberg K et al., *J Bacteriol.* 1989; 171(11):6357-6362; Inaba S et al., *Biopolymers.* 2013; 99(1):63-72). The FliD capping protein is an essential factor for polymerization of secreted flagellin monomers into flagella polymers, and in the absence of effective FliD function, flagellin monomers are secreted into the extracellular space in an unpolymerized form. The FliD protein of *E. coli* is an effective substitute for *Pseudomonas aeruginosa* FliD, and expression of PA flagellins in *E. coli* leads to fully formed and functional flagella. By comparison, *Salmonella* FliD does not mediate functional polymerization of *Pseudomonas aeruginosa* flagellins into flagella, and expression of *Pseudomonas aeruginosa* flagellins in *Salmonella* causes secretion into the cell supernatant (Inaba S et al., *Biopolymers.* 2013; 99(1):63-72). It has also been shown that *Pseudomonas aeruginosa* flagellin expressed in a heterologous GNB system is protective, as immunization with recombinant A-type flagellin produced in *E. coli* provided robust protection against burn wound infection with flagellin type A expressing *Pseudomonas aeruginosa*, including clinical isolates (Faezi S et al., *APMIS*. 2013). Monoclonal antibodies towards FlaA or FlaB, that have protected against burn wounds with the homologous Fla expressing *Pseudomonas aeruginosa*, recognize equivalently the cell-associated flagellin on *Pseudomonas aeruginosa* and the recombinant soluble *Pseudomonas aeruginosa* flagellin expressed in *E. coli* (Barnea Y et al., *Burns*. 2009; 35(3): 390-396; Adawi A et al., *Int J Mol Med*. 2012; 30(3):455-464).

Immune responses towards the flagellins of several bacterial pathogens (e.g., *Salmonella* (Simon R, *Infect Immun*. 2011; 79(10):4240-4249; McSorley S J et al., *J Immunol*. 2000; 164(2):986-993), *Pseudomonas aeruginosa* (Doring G et al., *Vaccine*. 2008; 26(8):1011-1024), *Burkholderia* (Brett P J et al., *Infect Immun*. 1996; 64(7):2824-2828)) have provided protection in animal models against infection. Flagellins have also been explored as carrier proteins for homologous pathogen bacterial surface polysaccharides. A conjugate vaccine comprised of *Burkholderia pseudomallei* COPS with the homologous strain flagellin (FliC) enhanced the anti-polysaccharide immune response, and antibodies induced by this vaccine imparted robust protection against *B. pseudomallei* infection (Brett P J et al., *Infect Immun*. 1996; 64(7):2824-2828). The inventors have found that conjugation of *Salmonella enterica* serovar Enteritidis COPS with *S. Enteritidis* flagellin enhances the anti-polysaccharide immune response and protects against fatal *S. Enteritidis* infection in mice (Simon R, *Infect Immun*. 2011; 79(10):4240-4249; Raphael Simon J Y W et al., *PLOS ONE*. 2013; 8(5):e64680). Conjugation of *Pseudomonas aeruginosa* alginate polysaccharide with a recombinant A-type *Pseudomonas aeruginosa* flagellin was also found to increase anti-alginate antibody levels, and elicit antibodies that protected by passive transfer against pneumonic PA infection with both mucoid and non-mucoid strains (Campodonico V L et al., *Infect Immun*. 2011; 79(8):3455-3464). Importantly, in all cases, antibody levels to polysaccharide conjugated flagellin were robust and equivalent to unconjugated flagellin, indicating that conjugation does not interfere with anti-flagellin immunity.

There remains a need for a broad spectrum vaccine that is effective against *Klebsiella pneumoniae* and *Pseudomonas aeruginosa*. The present invention provides multivalent conjugates directed against various *Klebsiella pneumoniae* serovars as well as *Pseudomonas aeruginosa* for use in vaccines.

This background information is provided for informational purposes only. No admission is necessarily intended, nor should it be construed, that any of the preceding information constitutes prior art against the present invention.

SUMMARY OF THE INVENTION

It is to be understood that both the foregoing general description of the embodiments and the following detailed description are exemplary, and thus do not restrict the scope of the embodiments.

According to non-limiting example embodiments, in one aspect, the invention is directed to a single conjugate vaccine for preventing bacterial infections in a human subject caused by *Klebsiella* and *Pseudomonas* bacteria wherein the conjugate vaccine is comprised of flagellin proteins of *Pseudomonas* and surface polysaccharide antigens and/or the core oligosaccharides of *Klebsiella*.

In one embodiment the present invention relates to a single conjugate vaccine for preventing bacterial infections in a human subject caused by *Klebsiella* and *Pseudomonas* bacteria wherein the conjugate vaccine is comprised of flagellin proteins or fragments or derivatives thereof of *Pseudomonas* and O polysaccharide antigens and/or the core oligosaccharides derived from *Klebsiella*.

In another embodiment the present invention relates to a conjugate vaccine composition comprising six individual antigens selected from two flagellin proteins or fragments or derivatives thereof derived from *Pseudomonas* species and nine O polysaccharide (OPS) antigens selected from *Klebsiella* species.

In another embodiment the present invention relates to a single quadrivalent conjugate vaccine comprising two *Pseudomonas* species flagellins or fragments or derivatives thereof as carriers for four *Klebsiella* species O polysaccharide antigens.

In another embodiment the present invention relates to a method for preparing a conjugate vaccine for preventing *Pseudomonas* and *Klebsiella* bacterial infections comprising linking OPS antigens and flagellin proteins or fragments or derivatives thereof using a variety of chemical crosslinking agents.

In another embodiment the present invention relates to a method for preparing a conjugate vaccine for preventing *Pseudomonas* and *Klebsiella* bacterial infections comprising expressing the bacterial flagellin proteins of *Pseudomonas* in a variety of suitable bacterial expression vectors and purifying the OPS from *Klebsiella* using a variety of commonly used methods followed by crosslinking of the OPS antigens with the flagellin proteins.

In another embodiment the present invention relates to a passive immunization method for treating a human subject with a *Pseudomonas* or *Klebsiella* bacterial infection with immunologically effective amount of an intravenous immunoglobulin preparation (IVIG) prepared from a human host which has been vaccinated with a conjugate vaccine comprising O polysaccharides or core oligosaccharides from *Klebsiella* with flagellin proteins or fragments or derivatives thereof.

In another embodiment the present invention relates to a method for eliciting a passive immune response in a subject comprising administering to the subject in need thereof an immunologically effective amount of an intravenous immunoglobulin preparation prepared by administering to animals a conjugate vaccine comprising an O polysaccharide (OPS) from a *Klebsiella* species covalently linked to a flagellin protein or fragment or a derivative thereof from a *Pseudomonas* species.

In another embodiment the present invention relates to a method for constructing a conjugate vaccine for eliciting an immune response in a subject in need thereof comprising producing recombinant microorganisms which produce large amounts of *Pseudomonas aeruginosa* flagellin or fragments or derivatives thereof and *Klebsiella pneumoniae* O polysaccharides.

In another embodiment the present invention relates to a method for producing a conjugate vaccine for *Klebsiella* and/or *Pseudomonas* infections comprising producing recombinant microorganisms which produce large amounts of *Pseudomonas* bacterial flagellins or fragments or derivatives thereof which are then conjugated (linked) with O polysaccharides or core oligosaccharides from recombinant *Klebsiella* bacterial strains wherein capsule removal from the *Klebsiella* strain is not required.

In another embodiment the present invention relates to a method for producing a conjugate vaccine for *Klebsiella* and/or *Pseudomonas* infections comprising producing recombinant bacterial expression systems using *E. coli, Salmonella*, or *Pseudomonas* which are engineered to produce large amounts of bacterial flagellins or fragments or derivatives thereof into culture supernatant which are then conjugated (linked) with O polysaccharides or core oligosaccharides produced from recombinant attenuated *Klebsiella* bacterial strains.

In another embodiment the present invention relates to a method for eliciting an active immune response and antibody production in a subject comprising administering to the subject in need thereof an immunologically effective amount of a conjugate vaccine comprising an O polysaccharide (OPS) from a *Klebsiella* species covalently linked to a flagellin protein or fragment or a derivative thereof from a *Pseudomonas* species wherein the flagellin protein acts as a carrier protein(s) in the conjugate vaccine.

In another embodiment the present invention relates to a method for inducing an immune response in a mammal comprising administering to the subject in need thereof a conjugate vaccine comprising an O polysaccharide (OPS) from a *Klebsiella* species covalently linked to a flagellin protein or fragment or a derivative thereof from a *Pseudomonas* species wherein the dosage of vaccine is about 5 to about 50 micrograms.

In another embodiment the present invention relates to a method for inducing an immune response in a mammal comprising administering to the subject in need thereof a conjugate vaccine comprising an O polysaccharide (OPS) from a *Klebsiella* species covalently linked to a flagellin protein or fragment or a derivative thereof from a *Pseudomonas* species wherein the wherein the route of administration is subcutaneous, intravenous, intradermal, intramuscular or intranasal.

In another embodiment the present invention relates to a method for inducing an immune response in a mammal comprising administering to the subject in need thereof a conjugate vaccine comprising an O polysaccharide (OPS) from a *Klebsiella* species covalently linked to a flagellin protein or fragment or a derivative thereof from a *Pseudomonas* species along with an adjuvant selected from the group comprising or consisting of alum, a PRR ligand, TLR3 ligand, TLR4 ligand, TLR5 ligand, TLR6 ligand, TLR7/8 ligand, TLR9 ligand, NOD2 ligand, and lipid A and analogues thereof.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The skilled artisan will understand that the drawings, described below, are for illustration purposes only. The drawings are not intended to limit the scope of the present teachings in any way.

ΔguaBA. Primer pairs used for the amplification: lanes 1 and 2, guaBA_256_F+guaBA_155_R; lanes 3 to 6, guaB_F2+guaA_R2.

Figure 13:
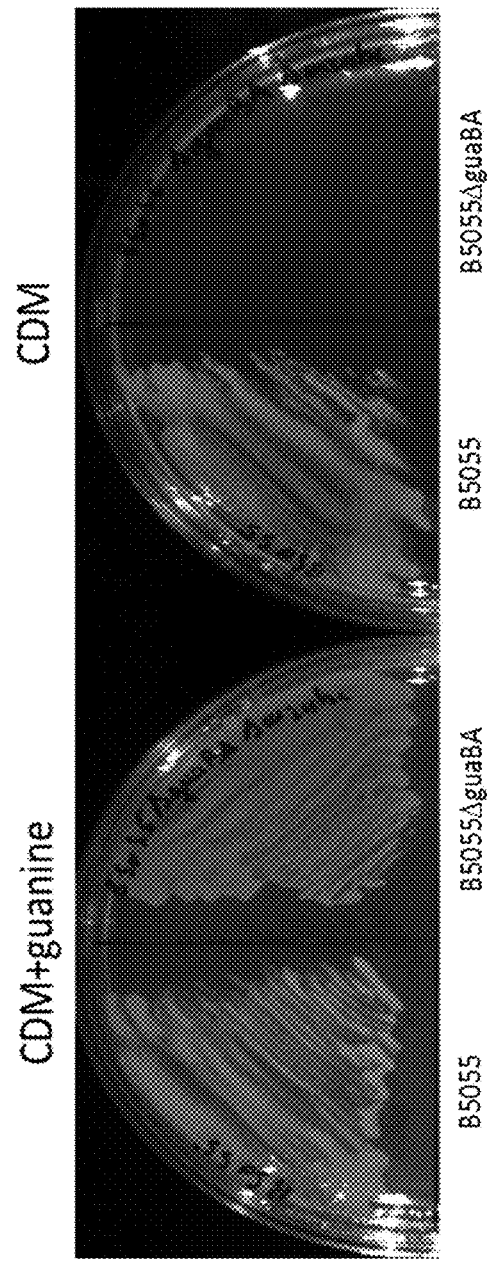

FIG. 13. Test for guanine auxotrophy of *K. pneumoniae* ΔguaBA reagent strains. CDM=chemically defined medium; CDM+guanine=CDM supplemented with 0.1% guanine.

Figure 14:
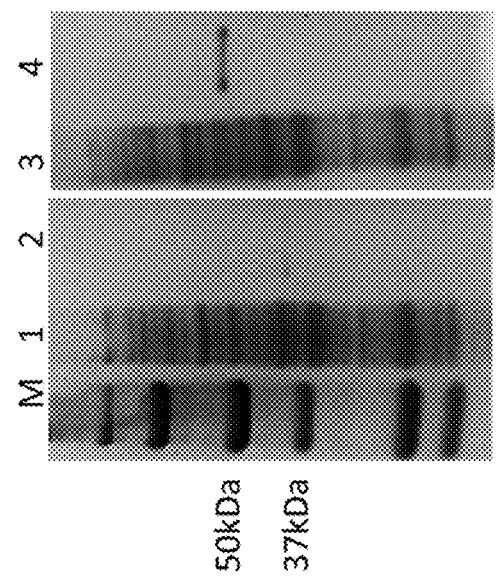

FIG. 14. Expression and secretion of rFlaA and rFlaB in CVD 1947. SDS-PAGE and coomassie analysis of cell pellets (lanes 1, 3) and supernatants (lanes 2, 4) from liquid cultures of CVD1947-pSEC10_flaA (lanes 1, 2) and CVD 1947-pSEC10 flaB (lanes 3, 4) grown in Hy-Soy. Lane: M, molecular weight standards.

Figure 15:
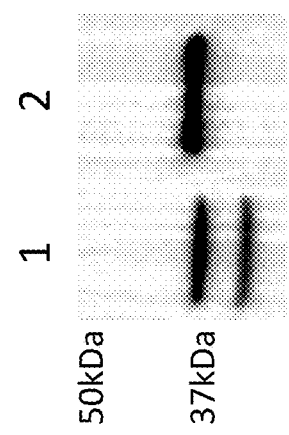

FIG. 15. Reactivity of recombinant *P. aeruginosa* flagellin FlaA secreted from *S. Enteritidis* CVD 1947 by sera raised against native FlaA. Cells (lane 1) and supernatants (lane 2) from liquid growth cultures of CVD1947-pSEC10_flaA were assessed by Western blot with polyclonal sera from mice immunized with FlaA purified from PAK FIG. 16. Purification of *P. aeruginosa* flagellin produced in CVD1947. Purified fraction (lane 1) was assessed for size and purity by SDS-PAGE with coomassie staining. Lane: M, molecular weight standards; 2, purified rFlaA.

FIG. 17. HPLC-SEC analysis of conjugated and unconjugated KP-O1 OPS and rPA-FlaA. Chromatogram for Purified KP-O1 OPS (Black line), rPA-FlaA (grey line), and CDAP linked KP-O1:rPA-FlaA conjugate (blue line) analyzed by HPLC-SEC through a Biosep SEC4000 column at lml/min in PBS with detection by Refractive index.

FIG. 18. SDS-PAGE analysis of rFlaA and KP-O1:rPA-FlaA conjugate. Coomassie staining (A) and Western blot with polyclonal mouse anti-FlaA sera (B). Sample and protein amount run are detailed in the figure for each lane.

FIG. 19. Dot blot analysis for KP-O1 OPS and KP-O1:rPA-FlaA with anti-KP-O1 sera. Equivalent amounts of polysaccharide either as conjugate with rFlaA or alone were blotted onto a PVDF membrane and probed with polyclonal mouse sera raised against CVD 3001 (KP-O1 OPS).

FIG. 20. Diagram of challenge study. Sun-type KP-O1-OPS:PA-FlaA conjugate (oxime), lattice type conjugate (CDAP), O1 OPS alone or admixed with FlaA will be used to immunize mice (black arrow). PBS is control. Levels of vaccine induced IgG antibodies in sera before immunization and 21 days after each vaccine dose will be measured by ELISA, motility inhibition and OPA assays (red arrow). Mice will be challenged with IP with KP or in burn wound infections with PA. For challenge, we will use PA PAK (type A flagellin-expressing isolate) or (KP B5055).

FIG. 21. Diagram of challenge study. The most effective KP-O1-OPS:PA-FlaA conjugate and O1 OPS admixed with FlaA will be used to immunize mice (black arrow). PBS is control. Levels of vaccine induced IgG antibodies in sera before immunization and 21 days after each vaccine dose will be measured by ELISA, motility inhibition and OPA assays (red arrow). Mice will be challenged with burn, myositis, punch wound, or IP septicemia PA infection routes. We will use PA PAK (type A flagellin-expressing isolate) or (KP B5055).

FIG. 22. Diagram of challenge study. Screen for functional efficacy of vaccine-elicited antibodies in vivo by measuring protection against IP infection with the homologous KP O type expressing strain (O1: B5055; O2, O3 and O5: recombinant mouse virulent strains), and burn wounds with the homologous flagellin expressing PA strain. Black arrow is introduction of immunogen. Red arrow is blood sampling to measure levels of vaccine induced IgG antibodies in sera before immunization and 21 days after each vaccine dose by ELISA, motility inhibition and OPA assays.

FIG. 23. Diagram of challenge study. To confirm that the specific immune responses to FlaA and FlaB are maintained when co-formulated, mice will be immunized 3 times at 28 day intervals with monovalent and bivalent flagellin preparations (black arrow). Levels of IgG and functional titers for the homologous Fla types will be determined in pre-immune sera and sera taken 21 days after the final dose (red arrow). Protection will be assessed against burn infection with homologous Fla expressing PA strains.

FIG. 24. Diagram of challenge study. An assay will be conducted to confirm that the humoral responses and protective efficacy of the 4 down-selected monovalent COPS and flagellin conjugate vaccine components are maintained when administered as a multivalent vaccine formulation. Mice will be immunized 3 times at 28 day intervals with PBS or the quadrivalent formulation, or 2 individual monovalent conjugates (black arrow). Sera obtained prior to immunization and 21 days after the final dose will be assessed for anti-LPS and anti-flagellin antibodies (red arrow). The protective efficacy of quadrivalent-relative to monovalent-vaccines to prevent invasive and wound infections will be determined using the IP, myositis, burn wound or punch-biopsy models and homologous KP O-type pathogens or the homologous flagellin type expressing PA (PAK or PA:O1).

FIG. 25. Diagram of challenge study. We will assess the utility of the quadrivalent conjugate formulation to generate antibody preparations. Rabbits will be hyper-immunized with quadrivalent vaccine and pooled sera will be prepared for use in passive transfer studies in mice. The level of anti-LPS and anti-flagellin IgG in rabbit sera will be determined by ELISA, OPA and motility inhibition assays. Dosage levels will be approximated to the antibody titer induced by active immunization in mice. Naïve mice will be intravenously administered immune sera, normal (unimmunized) rabbit sera (N. S.), or PBS, followed by IP or burn infection 2-4 hours later with KP B5055 or PA PAK, respectively.

FIG. 26. Diagram of challenge study. The 50% effective dose ($ED_{50}$) for various doses of KP B5055 O1:K2 and PA PAK will be determined by infecting at various doses at multiple wound sites in naïve pigs. Once a reliable infectious dose has been determined, we will immunize 4 pigs 3 times with PBS or quadrivalent conjugate containing 25 μg of total polysaccharide (black arrow). As controls, 2 pigs will be mock immunized with PBS alone. Twenty-one days after the final dose, immunized or control pigs will be infected at multiple sites with moderate or high levels of KP B5055 of PA PAK. Red arrows indicate blood sampling for antibody assays.

DETAILED DESCRIPTION OF THE INVENTION

The present invention provides a conjugate vaccine for *Klebsiella* and *Pseudomonas* bacterial infections. These bacteria are known to cause a wide variety of infections in human subjects including but not limited to wound infections, burn infections, urinary tract infections, respiratory infections, central nervous system infections, abscess formations, cystic fibrosis, in-dwelling catheter infections, invasive bacteremia, and septic shock. There is a real need to develop vaccines which can protect against such bacterial infections. In some embodiments, the present invention relates to a vaccine product which encompasses a tetravalent formulation of four different OPS polysaccharide antigens from *Klebsiella pneumoniae* serovars conjugated with two different flagellin proteins from *Pseudomonas aeruginosa*.

The vaccine can have efficacy for therapeutic use to mitigate against multiple drug resistant *Pseudomonas* and *Klebsiella* bacterial infections.

At present, there is no simple and broadly effective vaccine which is effective against both *Klebsiella* and *Pseudomonas*. In some aspects, the invention described herein is a novel conjugate vaccine which comprises antigens from both bacterial types and can be manufactured in a large scalable fashion. Moreover, in some embodiments, the vaccine could also be used to generate therapeutic immunoglobulin (IVIG) preparations for passive protection against acute infections.

Unless otherwise noted, technical terms are used according to conventional usage. Definitions of common terms in molecular biology may be found, for example, in Benjamin Lewin, *Genes VII*, published by Oxford University Press, 2000 (ISBN 019879276X); Kendrew et al. (eds.); *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar technical references.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of "or" means "and/or" unless stated otherwise. The use of "a" herein means "one or more" unless stated otherwise or where the use of "one or more" is clearly inappropriate. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

Conjugate

In one aspect, the present invention is directed to a conjugate comprising a *Klebsiella* surface polysaccharide antigen and a *Pseudomonas* flagellin protein or antigenic fragment or derivative thereof. In particular aspects of the invention, the surface polysaccharide antigen and the flagellin or antigenic fragment or derivative thereof are covalently linked optionally via a linker.

The *Klebsiella* surface polysaccharide antigen can be any known *Klebsiella* surface polysaccharide antigen or a derivative or antigenic fragment thereof. In some embodiments, the surface polysaccharide is from one or more *Klebsiella pneumoniae* serovars. In some aspects of the invention, the *Klebsiella* surface polysaccharide antigen can be an O polysaccharide (OPS), a core oligosaccharide and an O polysaccharide (COPS), a capsule polysaccharide or combinations thereof.

As used herein, "OPS" is a polysaccharide in which the lipid A moiety from lipopolysaccharide (LPS) and core oligosaccharide have been removed. In some embodiments of the invention, the surface polysaccharide antigen is an OPS. In some embodiments, the surface polysaccharide antigen is from epidemiologically relevant *Klebsiella* O serovars such as *Klebsiella pneumoniae* serovar O1, O2a, O3 and O5. In some embodiments, the surface polysaccharide antigen is an OPS derived from *Klebsiella pneumoniae* serovars O1, O2a, O2a,c, O3, O4, O5, O7, O8 and O12. In some embodiments, the surface polysaccharide antigen is an OPS derived from *Klebsiella pneumoniae* serovars O1, O2a, O3 and O5.

The *Pseudomonas* flagellin can be any known *Pseudomonas* flagellin. As used herein, the term "flagellin" encompasses flagellin, fragments of flagellin and derivatives thereof. In particular aspects of the invention, the *Pseudomonas* flagellin is a *Pseudomonas aeruginosa* (PA) flagellin. It is believed that all pathogenic *Pseudomonas aeruginosa* express a single polar flagellum that extends from the cell surface to enable motility, that is comprised chiefly by polymers of either type A or B flagellin proteins. In some aspects of the invention, the *Pseudomonas* flagellin is a *Pseudomonas aeruginosa* (PA) flagellin type A (FlaA) or an antigenic fragment or derivative thereof and/or a *Pseudomonas aeruginosa* flagellin type B (FlaB) or an antigenic fragment or derivative thereof. In some embodiments, the *Pseudomonas aeruginosa* flagellin type A (FlaA) comprises SEQ ID NO:1 or an antigenic fragment or derivative thereof. In some embodiments, the *Pseudomonas aeruginosa* flagellin type B (FlaB) comprises SEQ ID NO:2 or an antigenic fragment or derivative thereof. FliC and Fla (e.g., FlaA and FlaB) are used interchangeably throughout the specification but all refer to flagellin.

In some embodiments, the conjugate comprises i) *Pseudomonas aeruginosa* flagellin type A (FlaA) or an antigenic fragment or derivative thereof and/or *Pseudomonas aeruginosa* flagellin type B (FlaB) or an antigenic fragment or derivative thereof and ii) OPS from *Klebsiella pneumoniae* selected from *Klebsiella pneumoniae* serovars O1, O2a, O3, O5 or combinations thereof. In some embodiments, *Pseudomonas* flagellin or an antigenic fragment or derivative thereof can be covalently linked to one or more OPS from a single *Klebsiella pneumoniae* serovar type or may be linked to OPS from multiple *Klebsiella pneumoniae* serovar types.

The ratio or stoichiometry of surface polysaccharide to flagellin is not limiting. In some embodiments, the *Pseudomonas flagellin* or an antigenic fragment or derivative thereof can be linked to 1, 2, 3, 4, 5, 6, 7, 8, 9, 10 or more surface polysaccharides, such as OPS, from the same *Klebsiella* or from mixtures of *Klebsiella* serovar types.

In some embodiments, the *Pseudomonas* flagellin or an antigenic fragment or derivative thereof is linked to one to four OPS from the same serovar type. In another embodiment, the *Pseudomonas* flagellin or an antigenic fragment or derivative thereof is linked to one to four OPS from at least two different serovar types. In another embodiment, the flagellin or an antigenic fragment or derivative thereof is linked to one to four OPS, each from different serovar types. In some embodiments, the *Klebsiella* serovars comprise *Klebsiella pneumoniae* serovar O1, O2a, O3, and O5.

In one embodiment, the conjugate comprises SEQ ID NO:1 or an antigenic fragment or derivative thereof and a surface polysaccharide from *Klebsiella pneumoniae* serovars O1, O2a, O3, O5 or combinations thereof. In some embodiments, the surface polysaccharide is OPS.

In another embodiment, the conjugate comprises SEQ ID NO:2 or an antigenic fragment or derivative thereof and a surface polysaccharide from *Klebsiella pneumoniae* serovars O1, O2a, O3, O5 or combinations thereof. In some embodiments, the surface polysaccharide is OPS.

Examples of fragments or derivatives of *Pseudomonas* flagellin can include fragments of the natural protein, including internal sequence fragments of the protein that retain their ability to elicit protective antibodies against a desired bacteria. The derivatives are also intended to include variants of the natural protein such as proteins having changes in amino acid sequence but that retain the ability to elicit an immunogenic, biological, or antigenic property as exhibited by the natural molecule.

By derivative is further meant an amino acid sequence that is not identical to the wild type amino acid sequence, but rather contains at least one or more amino acid changes (deletion, substitutions, inversion, insertions, etc.) that do not essentially affect the immunogenicity or protective antibody responses induced by the modified protein as compared to a similar activity of the wild type amino acid sequence, when used for the desired purpose. In some embodiments, a derivative amino acid sequence contains at least 85-99% homology at the amino acid level to the specific amino acid sequence. In further embodiments, the derivative has at least 90% homology at the amino acid level. In other embodiments, the derivative has at least 95% homology.

The flagellin of the invention may be a peptide encoding the native amino acid sequence or it may be a derivative or antigenic fragment of the native amino acid sequence.

In some embodiments, the surface polysaccharide antigen of a *Klebsiella* is covalently linked to the *Pseudomonas* flagellin protein or an antigenic fragment or a derivative thereof either directly or with a linker. In some embodiments, the linker or linking chemical is selected from 1-cyano-4-dimethylaminopyridinium tetrafluoroborate (CDAP), adipic acid dihydrazide, ε-aminohexanoic acid, chlorohexanol dimethyl acetal, D-glucuronolactone or p-nitrophenylethyl amine. In a particular embodiment, the linking chemical is CDAP.

Compositions

In some embodiments, the invention provides compositions comprising the conjugates of the invention. In some embodiments, the compositions are vaccine compositions which provide protective immunity against one or more *Klebsiella* and/or *Pseudomonas* pathogens and which comprise one or more of the above-mentioned conjugates. In some embodiments, effective amounts of one or more unconjugated *Pseudomonas* flagellin can be added to the compositions of the invention. In some embodiments, adding one or more unconjugated flagellin to compositions comprising one or more conjugates can enhance the immune response to the flagellin epitopes. In some embodiments, the one or more unconjugated *Pseudomonas* flagellin is selected from flagellin comprising SEQ ID NO:1, SEQ ID NO:2, antigenic fragments and derivatives thereof and combinations thereof.

In some embodiments of the invention, the vaccine composition is a multivalent conjugate vaccine comprising one or more *Pseudomonas* flagellins linked to one or more *Klebsiella* surface polysaccharides, such as O polysaccharides (OPS). For example, the composition can be a multivalent conjugate vaccine comprising two different *Pseudomonas* flagellin proteins or antigenic fragments or derivatives thereof covalently linked to one or more *Klebsiella* O polysaccharides (OPS). In some embodiments, the multivalent conjugate vaccine comprises OPS antigens from one or more of *Klebsiella pneumoniae* serovars O1, O2a, O2a,c, O3, O4, O5, O7, O8 and O12. In some embodiments, the multivalent conjugate vaccine comprises four different OPS antigens from *Klebsiella pneumoniae* serovars O1, O2a, O3, and O5. In some embodiments, the *Pseudomonas* is *Pseudomonas aeruginosa*.

In some embodiments, the composition comprises an effective amount of one or more conjugates comprising a *Pseudomonas* flagellin protein or an antigenic fragment or derivative thereof and a surface polysaccharide from *Klebsiella*. In one embodiment, the composition comprises a *Pseudomonas aeruginosa* flagellin or an antigenic fragment or derivative thereof and an OPS from *Klebsiella pneumoniae* serovars O1, O2a, O3, O5 or combinations thereof.

In some embodiments, the composition comprises a multivalent conjugate vaccine comprising one or more *Pseudomonas aeruginosa* flagellin proteins selected from the group consisting of SEQ ID NO:1, SEQ ID NO:2 and combinations thereof, or antigenic fragments or derivative thereof and one or more OPS from *Klebsiella pneumoniae* serovars O1, O2a, O3, O5 or combinations thereof.

In some embodiments, the composition comprises:
i) a conjugate comprising a *Pseudomonas aeruginosa* flagellin protein according to SEQ ID NO:1 or an antigenic fragment or derivative thereof and one or more OPS from *Klebsiella pneumoniae* serovars O1, O2a, O3, O5 or combinations thereof; and
ii) a conjugate comprising a *Pseudomonas aeruginosa* flagellin protein according to SEQ ID NO:2 or an antigenic fragment or derivative thereof and one or more OPS from *Klebsiella pneumoniae* serovars O1, O2a, O3, O5 or combinations thereof.

In some embodiments, the composition comprises:
i) a conjugate comprising a *Pseudomonas aeruginosa* flagellin protein according to SEQ ID NO:1 or an antigenic fragment or derivative thereof and one or more OPS from *Klebsiella pneumoniae* serovar O1;
ii) a conjugate comprising a *Pseudomonas aeruginosa* flagellin protein according to SEQ ID NO:1 or an antigenic fragment or derivative thereof and one or more OPS from *Klebsiella pneumoniae* serovar O2a;
iii) a conjugate comprising a *Pseudomonas aeruginosa* flagellin protein according to SEQ ID NO:2 or an antigenic fragment or derivative thereof and one or more OPS from *Klebsiella pneumoniae* serovar O3; and
iv) a conjugate comprising a *Pseudomonas aeruginosa* flagellin protein according to SEQ ID NO:2 or an antigenic fragment or derivative thereof and one or more OPS from *Klebsiella pneumoniae* serovar O5.

In some embodiments, the composition comprises:
i) a conjugate comprising a *Pseudomonas aeruginosa* flagellin protein according to SEQ ID NO:1 or an antigenic fragment or derivative thereof and one or more OPS from *Klebsiella pneumoniae* serovar O1;
ii) a conjugate comprising a *Pseudomonas aeruginosa* flagellin protein according to SEQ ID NO:1 or an antigenic fragment or derivative thereof and one or more OPS from *Klebsiella pneumoniae* serovar O3;
iii) a conjugate comprising a *Pseudomonas aeruginosa* flagellin protein according to SEQ ID NO:2 or an antigenic fragment or derivative thereof and one or more OPS from *Klebsiella pneumoniae* serovar O2a; and
iv) a conjugate comprising a *Pseudomonas aeruginosa* flagellin protein according to SEQ ID NO:2 or an antigenic fragment or derivative thereof and one or more OPS from *Klebsiella pneumoniae* serovar O5.

In some embodiments, the composition comprises:
i) a conjugate comprising a *Pseudomonas aeruginosa* flagellin protein according to SEQ ID NO:1 or an antigenic fragment or derivative thereof and one or more OPS from *Klebsiella pneumoniae* serovar O1;
ii) a conjugate comprising a *Pseudomonas aeruginosa* flagellin protein according to SEQ ID NO:1 or an antigenic fragment or derivative thereof and one or more OPS from *Klebsiella pneumoniae* serovar O5;
iii) a conjugate comprising a *Pseudomonas aeruginosa* flagellin protein according to SEQ ID NO:2 or an antigenic fragment or derivative thereof and one or more OPS from *Klebsiella pneumoniae* serovar O2a; and
iv) a conjugate comprising a *Pseudomonas aeruginosa* flagellin protein according to SEQ ID NO:2 or an antigenic fragment or derivative thereof and one or more OPS from *Klebsiella pneumoniae* serovar O3.

In some embodiments, the composition comprises:
i) a conjugate comprising a *Pseudomonas aeruginosa* flagellin protein according to SEQ ID NO:1 or an antigenic fragment or derivative thereof and OPS from *Klebsiella pneumoniae* serovar O2a;
ii) a conjugate comprising a *Pseudomonas aeruginosa* flagellin protein according to SEQ ID NO:1 or an antigenic fragment or derivative thereof and OPS from *Klebsiella pneumoniae* serovar O5;
iii) a conjugate comprising a *Pseudomonas aeruginosa* flagellin protein according to SEQ ID NO:2 or an antigenic fragment or derivative thereof and OPS from *Klebsiella pneumoniae* serovar O1; and
iv) a conjugate comprising a *Pseudomonas aeruginosa* flagellin protein according to SEQ ID NO:2 or an antigenic fragment or derivative thereof and OPS from *Klebsiella pneumoniae* serovar O3.

In some embodiments, the composition comprises:
i) a conjugate comprising a *Pseudomonas aeruginosa* flagellin protein according to SEQ ID NO:1 or an antigenic fragment or derivative thereof and OPS from *Klebsiella pneumoniae* serovar O3;
ii) a conjugate comprising a *Pseudomonas aeruginosa* flagellin protein according to SEQ ID NO:1 or an antigenic fragment or derivative thereof and OPS from *Klebsiella pneumoniae* serovar O5;
iii) a conjugate comprising a *Pseudomonas aeruginosa* flagellin protein according to SEQ ID NO:2 or an antigenic fragment or derivative thereof and OPS from *Klebsiella pneumoniae* serovar O1; and
iv) a conjugate comprising a *Pseudomonas aeruginosa* flagellin protein according to SEQ ID NO:2 or an antigenic fragment or derivative thereof and OPS from *Klebsiella pneumoniae* serovar O2a.

In some embodiments, the composition comprises:
i) a conjugate comprising a *Pseudomonas aeruginosa* flagellin protein according to SEQ ID NO:1 or an antigenic fragment or derivative thereof and OPS from *Klebsiella pneumoniae* serovar O2a;
ii) a conjugate comprising a *Pseudomonas aeruginosa* flagellin protein according to SEQ ID NO:1 or an antigenic fragment or derivative thereof and OPS from *Klebsiella pneumoniae* serovar O3;
iii) a conjugate comprising a *Pseudomonas aeruginosa* flagellin protein according to SEQ ID NO:2 or an antigenic fragment or derivative thereof and OPS from *Klebsiella pneumoniae* serovar O1; and
iv) a conjugate comprising a *Pseudomonas aeruginosa* flagellin protein according to SEQ ID NO:2 or an antigenic fragment or derivative thereof and OPS from *Klebsiella pneumoniae* serovar O5.

In some embodiments, the invention provides a composition comprising an effective amount of sera from a subject administered one or more conjugates of the invention. In some embodiments, the invention provides a composition comprising an effective amount of purified or enriched immunoglobulins from a subject administered one or more conjugates of the invention. In some embodiments, the composition comprising sera or the immunoglobulins can be administered to a subject in immunotherapy applications.

In some embodiments, the compositions are pharmaceutical compositions comprising one or more conjugates of the invention and a pharmaceutically acceptable carrier. In some embodiments, the pharmaceutical composition can contain salts, buffers, adjuvants, or other substances which are desirable for improving the efficacy of the composition. Adjuvants are substances that can be used to specifically augment a specific immune response. Normally, the adjuvant and the composition are mixed prior to presentation to the immune system, or presented separately, but into the same site of the animal being immunized. Adjuvants can be loosely divided into several groups based upon their composition. These groups include oil adjuvants (for example, Freund's complete and incomplete), mineral salts (for example, $AlK(SO_4)_2$, $AlNa(SO_4)_2$, $AlNH_4$ $(SO_4)$, silica, kaolin, and carbon), polynucleotides (for example, poly IC and poly AU acids), and certain natural substances (for example, wax D from *Mycobacterium tuberculosis*, as well as substances found in *Corynebacterium parvum*, or *Bordetella pertussis*, and members of the genus *Brucella*. Adjuvants are described by Warren et al. (*Ann. Rev. Biochem.*, 4:369-388, 1986), the entire disclosure of which is hereby incorporated by reference. Further adjuvants suitable for use in the present invention include alum, a PRR ligand, TLR3 ligand, TLR4 ligand, TLR5 ligand, TLR6 ligand, TLR7/8 ligand, TLR9 ligand, NOD2 ligand, and lipid A and analogues thereof.

In some embodiments of the invention the use of a flagellin protein or antigenic fragment or derivative thereof as a carrier for a conjugate provides an inherent adjuvant boost, and stimulates a robust immune response without the addition of further adjuvant. Thus, in some embodiments, the flagellin protein antigenic fragment or derivative thereof acts an adjuvant which stimulates innate immunity through TLR5 to improve the immunogenicity of surface polysaccharide antigen (e.g., OPS) within the composition. In some embodiments, the carrier is a mutant flagellin antigenic fragment or derivative thereof which has a diminished capability to stimulate innate immunity through TLR5. In some embodiments, an adjuvant is added to the compositions while in other embodiments, no adjuvant is added.

In some embodiments, conventional adjuvants can be administered. Among those substances that can be included are the saponins such as, for example, Quil A. (Superfos A/S, Denmark). In some embodiments, immunogenicity of the conjugates in both mice and rabbits is enhanced by the use of monophosphoryl lipid A plus trehalose dimycolate (Ribi-700; Ribi Immunochemical Research, Hamilton, Mont.) as an adjuvant. Alum, a PRR ligand, TLR3 ligand, TLR 4 ligand, TLR5 ligand, TLR6 ligand, TLR7/8 ligand, TLR9 ligand, NOD2 ligand, and lipid A and analogues thereof may separately or in combination may also be used as adjuvants. Examples of materials suitable for use in vaccine compositions are provided in *Remington's Pharmaceutical Sciences*

(Osol, A, Ed, Mack Publishing Co, Easton, Pa., pp. 1324-1341 (1980), which disclosure is incorporated herein by reference).

In some embodiments, the vaccine composition can be formulated into liquid preparations for, e.g., nasal, rectal, buccal, vaginal, peroral, intragastric, mucosal, perlinqual, alveolar, gingival, olfactory, or respiratory mucosa administration. Suitable forms for such administration include solutions, suspensions, emulsions, syrups, and elixirs. The vaccine composition can also be formulated for parenteral, subcutaneous, intradermal, intramuscular, intraperitoneal or intravenous administration, injectable administration, sustained release from implants, or administration by eye drops. Suitable forms for such administration include sterile suspensions and emulsions. Such vaccine composition can be in admixture with a suitable carrier, diluent, or excipient such as sterile water, physiological saline, glucose, and the like. The vaccine composition can also be lyophilized. The vaccine composition can contain auxiliary substances such as wetting or emulsifying agents, pH buffering agents, gelling or viscosity enhancing additives, preservatives, flavoring agents, colors, and the like, depending upon the route of administration and the preparation desired. Texts, such as *Remington: The Science and Practice of Pharmacy*, Lippincott Williams & Wilkins; 20th edition (Jun. 1, 2003) and *Remington's Pharmaceutical Sciences*, Mack Pub. Co.; $18^{th}$ and $19^{th}$ editions (December 1985, and June 1990, respectively), incorporated herein by reference in their entirety, can be consulted to prepare suitable preparations. Such preparations can include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. The presence of such additional components can influence the physical state, solubility, stability, rate of in vivo release, and rate of in vivo clearance, and are thus chosen according to the intended application, such that the characteristics of the carrier are tailored to the selected route of administration.

In some embodiments, the vaccine composition of the invention is administered parenterally. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. In some embodiments, the vaccine composition for parenteral administration may be in the form of a sterile injectable preparation, such as a sterile injectable aqueous or nonaqueous solutions, suspensions, and emulsions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Suspensions may be formulated according to methods well known in the art using suitable dispersing or wetting agents and suspending agents. The sterile injectable preparation may also be a sterile injectable solution or suspension in a parenterally acceptable diluent or solvent, such as a solution in 1,3-butanediol. Suitable diluents include, for example, water, Ringer's solution and isotonic sodium chloride solution. In addition, sterile fixed oils may be employed conventionally as a solvent or suspending medium. For this purpose, any bland fixed oil may be employed including synthetic mono- or diglycerides. In addition, fatty acids such as oleic acid may likewise be used in the preparation of injectable preparations.

Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

In some embodiments, the vaccine composition is provided as a liquid suspension or as a freeze-dried product (or freeze-dried hyperimmune globulin for oral administration). Suitable liquid preparations include, e.g., isotonic aqueous solutions, suspensions, emulsions, or viscous compositions that are buffered to a selected pH. Transdermal preparations include lotions, gels, sprays, ointments or other suitable techniques. If nasal or respiratory (mucosal) administration is desired (e.g., aerosol inhalation or insufflation), compositions can be in a form and dispensed by a squeeze spray dispenser, pump dispenser or aerosol dispenser. Aerosols are usually under pressure by means of a hydrocarbon. Pump dispensers can preferably dispense a metered dose or a dose having a particular particle size, as discussed below.

In some embodiments, when in the form of solutions, suspensions and gels, in some embodiments, the composition contains a major amount of water (preferably purified endotoxin-free water) in addition to the active ingredient. Minor amounts of other ingredients such as pH adjusters, emulsifiers, dispersing agents, buffering agents, preservatives, wetting agents, jelling agents, colors, and the like can also be present.

In some embodiments, the compositions are preferably isotonic with the blood or other body fluid of the recipient. The isotonicity of the compositions can be attained using sodium tartrate, propylene glycol or other inorganic or organic solutes. Sodium chloride is particularly preferred. Buffering agents can be employed, such as acetic acid and salts, citric acid and salts, boric acid and salts, and phosphoric acid and salts. In some embodiments of the invention, phosphate buffered saline is used for suspension.

In some embodiments, the viscosity of the compositions can be maintained at the selected level using a pharmaceutically acceptable thickening agent. In some embodiments, methylcellulose is used because it is readily and economically available and is easy to work with. Other suitable thickening agents include, for example, xanthan gum, carboxymethyl cellulose, hydroxypropyl cellulose, carbomer, and the like. The concentration of the thickener can depend upon the agent selected. In some embodiments, viscous compositions are prepared from solutions by the addition of such thickening agents.

In some embodiments, a pharmaceutically acceptable preservative can be employed to increase the shelf life of the compositions. Benzyl alcohol can be suitable, although a variety of preservatives including, for example, parabens, thimerosal, chlorobutanol, or benzalkonium chloride can also be employed. A suitable concentration of the preservative can be from 0.02% to 2% based on the total weight although there can be appreciable variation depending upon the agent selected.

In some embodiments, pulmonary delivery of the composition can also be employed. In some embodiments, the composition is delivered to the lungs of a mammal while inhaling and traverses across the lung epithelial lining to the blood stream. A wide range of mechanical devices designed for pulmonary delivery of therapeutic products can be employed, including but not limited to nebulizers, metered dose inhalers, and powder inhalers, all of which are familiar to those skilled in the art. These devices employ formulations suitable for the dispensing of the conjugate. Typically, each formulation is specific to the type of device employed and can involve the use of an appropriate propellant material, in addition to diluents, adjuvants and/or carriers useful in therapy.

In embodiments where the compositions are prepared for pulmonary delivery in particulate form, it has an average particle size of from 0.1 μm or less to 10 μm or more. In some embodiments, it has an average particle size of from about 0.2, 0.3, 0.4, 0.5, 0.6, 0.7, 0.8, or 0.9 μm to about 1.0, 1.5, 2.0, 2.5, 3.0, 3.5, 4.0, 4.5, 5.0, 5.5, 6.0, 6.5, 7.0, 7.5, 8.0, 8.5, 9.0, or 9.5 μm for pulmonary delivery. Pharmaceutically acceptable carriers for pulmonary delivery of the insufflation include carbohydrates such as trehalose, mannitol, xylitol, sucrose, lactose, and sorbitol. Other ingredients for use in formulations can include DPPC, DOPE, DSPC and DOPC. Natural or synthetic surfactants can be used, including polyethylene glycol and dextrans, such as cyclodextran and other related enhancers, as well as cellulose and cellulose derivatives, and amino acids can also be used. Liposomes, microcapsules, microspheres, inclusion complexes, and other types of carriers can also be employed.

Formulations suitable for use with a nebulizer, either jet or ultrasonic, typically comprise the composition dissolved or suspended in water at a concentration of about 0.01 or less to 100 mg or more of conjugate per mL of solution, preferably from about 0.1, 1, 2, 3, 4, 5, 6, 7, 8, 9, or 10 mg to about 15, 20, 25, 30, 35, 40, 45, 50, 55, 60, 65, 70, 75, 80, 85, or 90 mg of conjugate per mL of solution. The formulation can also include a buffer and a simple sugar (e.g., for protein stabilization and regulation of osmotic pressure). The nebulizer formulation can also contain a surfactant, to reduce or prevent surface induced aggregation of the conjugate or composition caused by atomization of the solution in forming the aerosol.

Formulations for use with a metered-dose inhaler device generally comprise a finely divided powder containing the vaccine composition suspended in a propellant with the aid of a surfactant. The propellant can include conventional propellants, such chlorofluorocarbon, a hydrochlorofluorocarbons, hydrofluorocarbons, and hydrocarbons, such as trichlorofluoromethane, dichlorodifluoromethane, dichlorotetrafluoroethanol, and 1,1,1,2-tetrafluoroethane, and combinations thereof. Suitable surfactants include sorbitan trioleate, soya lecithin, and oleic acid.

Formulations for dispensing from a powder inhaler device typically comprise a finely divided dry powder containing the vaccine composition, optionally including a bulking agent, such as lactose, sorbitol, sucrose, mannitol, trehalose, or xylitol in an amount that facilitates dispersal of the powder from the device, typically from about 1 wt. % or less to 99 wt. % or more of the formulation, preferably from about 5, 10, 15, 20, 25, 30, 35, 40, 45, or 50 wt. % to about 55, 60, 65, 70, 75, 80, 85, or 90 wt. % of the formulation.

In some embodiments, the invention is directed to kits comprising one or more vaccine compositions of the invention. Such kits can be provided to an administering physician or other health care professional.

In some embodiments, the kit is a package that houses one or more containers which comprises one or more vaccine compositions and instructions for administering the vaccine composition to a subject. In some embodiments, the kit can also comprise one or more other therapeutic agents. The kit can optionally contain one or more diagnostic tools and instructions for use.

In some embodiments, the kit comprises an immunization schedule. In some embodiments, a vaccine cocktail containing two or more vaccine compositions can be included, or separate pharmaceutical compositions containing different vaccines or therapeutic agents. The kit can also contain separate doses of the vaccine composition for serial or sequential administration.

In some embodiments, the kit further comprises suitable delivery devices, e.g., syringes, inhalation devices, and the like, along with instructions for administrating the therapeutic agents. The kit can optionally contain instructions for storage, reconstitution (if applicable), and administration of any or all therapeutic agents included. The kits can include a plurality of containers reflecting the number of administrations to be given to a subject. If the kit contains a first and second container, then a plurality of these can be present.

Methods of Treatment

Another aspect of the invention is directed to a method of inducing an immune response, comprising administering to a subject in need thereof an immunologically-effective amount of the above-mentioned conjugate or composition. In some embodiments, the surface polysaccharide antigen is an O polysaccharide (OPS), a core oligosaccharide and an O polysaccharide (COPS), a capsule polysaccharide, or combinations thereof. In some embodiments of the invention, the surface polysaccharide antigen is an O polysaccharide antigen (OPS). The surface polysaccharide antigen and the flagellin can be covalently linked.

In some embodiments, methods of the claimed invention include administering multiple conjugates comprising one or more *Pseudomonas* flagellins or antigenic fragments or derivatives thereof covalently linked to one or more *Klebsiella* O polysaccharides (OPS) to induce an immune response. The multiple conjugates can comprise two different *Pseudomonas flagellin* covalently linked to one or more *Klebsiella* O polysaccharides (OPS). The two different *Pseudomonas* flagellins can be a *Pseudomonas aeruginosa* flagellin type A (FlaA) and a *Pseudomonas aeruginosa* flagellin type B (FlaB).

In further embodiments of the method, the multiple conjugates can comprise four different OPS antigens from *Klebsiella pneumoniae*. For example, the four different OPS can be derived from *Klebsiella pneumoniae* serovars O1, O2a, O3 and O5. Further, the two different *Pseudomonas* flagellins can be *Pseudomonas aeruginosa* flagellin type A (FlaA) and *Pseudomonas aeruginosa* flagellin type B (FlaB) and/or the four *Klebsiella* OPS can be from *Klebsiella pneumoniae* serovars O1, O2a, O3 and O5. The *Pseudomonas flagellin* can be covalently linked to one or more OPS from a single *Klebsiella pneumoniae* serovar type or can be covalently linked to OPS from multiple *Klebsiella pneumoniae* serovar types. The *Pseudomonas aeruginosa* flagellin type A (FlaA) can comprise SEQ ID NO:1 and/or the *Pseudomonas aeruginosa* flagellin type B (FlaB) can comprise SEQ ID NO:2.

In some embodiments, the conjugate or composition is administered multiple times to the subject. The conjugate or composition may also be administered a single time to the subject. The term "subject" as used herein, refers to animals, such as mammals. For example, mammals contemplated include humans, primates, dogs, cats, sheep, cattle, goats, pigs, horses, chickens, mice, rats, rabbits, guinea pigs, and the like. The terms "subject", "patient", and "host" are used interchangeably.

Human subjects are not limiting and can include deployed soldiers, hospital workers, patients and residents of chronic care facilities. In some embodiments, the patient is in a hospital or in a skilled nursing facility. In some embodiments, the subject is administered the conjugate or composition prior to, during, or after a surgery. The surgery is not limiting and can be, for example, colon surgery, hip arthroplasty, or small-bowel surgery. Further, the conjugate or composition can be administered prior to, during, or after a procedure selected from central venous catheterization, urinary tract catheterization, and intubation with a ventilator tube.

As used herein, an "immune response" is the physiological response of the subject's immune system to an immunizing composition. An immune response may include an innate immune response, an adaptive immune response, or both. In some embodiments of the present invention, the immune response is a protective immune response. A protective immune response confers immunological cellular memory upon the subject, with the effect that a secondary exposure to the same or a similar antigen is characterized by one or more of the following characteristics: shorter lag phase than the lag phase resulting from exposure to the selected antigen in the absence of prior exposure to the immunizing composition; production of antibody which continues for a longer period than production of antibody resulting from exposure to the selected antigen in the absence of prior exposure to the immunizing composition; a change in the type and quality of antibody produced in comparison to the type and quality of antibody produced upon exposure to the selected antigen in the absence of prior exposure to the immunizing composition; a shift in class response, with IgG antibodies appearing in higher concentrations and with greater persistence than IgM, than occurs in response to exposure to the selected antigen in the absence of prior exposure to the immunizing composition; an increased average affinity (binding constant) of the antibodies for the antigen in comparison with the average affinity of antibodies for the antigen resulting from exposure to the selected antigen in the absence of prior exposure to the immunizing composition; and/or other characteristics known in the art to characterize a secondary immune response.

In some embodiments, the immunogenicity of the conjugates and compositions of the invention are greater than the immunogenicity of at least one of the surface polysaccharide antigen or flagellin protein or an antigenic fragment or a derivative thereof alone. Methods of measuring immunogenicity are well known to those in the art and primarily include measurement of serum antibody including measurement of amount, avidity, and isotype distribution at various times after injection of the conjugate vaccine. Greater immunogenicity may be reflected by a higher titer and/or increased life span of the antibodies. Immunogenicity may also be measured by the ability to induce protection to challenge with noxious substances or virulent organisms. Immunogenicity may also be measured by the ability to immunize neonatal and/or immune deficient mice. Immunogenicity may be measured in the patient population to be treated or in a population that mimics the immune response of the patient population.

In some embodiments, the immune response that is generated by the conjugates and compositions of the invention is a protective immune response against infection by one or more *Klebsiella* and/or *Pseudomonas* serovars, including those serovars described herein.

In some embodiments, the conjugates and compositions of the invention are administered alone in a single dose or administered in sequential doses. In other aspects of the invention, the conjugates and compositions of the invention are administered as a component of a homologous or heterologous prime/boost regimen in conjunction with one or more vaccines. In some embodiments of the invention, a single boost is used. In some embodiments of the invention, multiple boost immunizations are performed. In particular aspects of the invention drawn to a heterologous prime/boost, a mucosal bacterial prime/parenteral conjugate boost immunization strategy is used. In some embodiments, one or more (or all) of the live (or killed) attenuated *Salmonella enterica* serovars used as a reagent strain to express *Pseudomonas* flagellin as taught herein can be administered orally to a subject and the subject can be subsequently boosted parenterally with a conjugates and compositions of the invention as described herein. In some embodiments, one or more (or all) of the live (or killed) attenuated *Klebsiella* used as a reagent strain to isolate surface polysaccharide as taught herein can be administered orally to a subject and the subject can be subsequently boosted parenterally with a conjugates and compositions of the invention as described herein.

In practicing immunization protocols for treatment and/or prevention, an immunologically-effective amount of conjugates and compositions of the invention are administered to a subject. As used herein, the term "immunologically-effective amount" means the total amount of therapeutic agent (e.g., conjugate or composition) or other active component that is sufficient to show an enhanced immune response in the subject. When "immunologically-effective amount" is applied to an individual therapeutic agent administered alone, the term refers to that therapeutic agent alone. When applied to a combination, the term refers to combined amounts of the ingredients that result in the therapeutic effect, whether administered in combination, serially or simultaneously, and regardless of order of administration.

The particular dosage depends upon the age, weight, sex and medical condition of the subject to be treated, as well as on the method of administration. Suitable doses can be readily determined by those of skill in the art.

The conjugates and compositions of the invention can be administered by either single or multiple dosages of an effective amount. In some embodiments, an effective amount of the compositions of the invention can vary from 0.01-5,000 µg/ml per dose. In other embodiments, an effective amount of the conjugate or composition of the invention can vary from 0.1-500 µg/ml per dose, and in other embodiments, it can vary from 10-300 µg/ml per dose. In one embodiment, the dosage of the conjugate or composition administered will range from about 10 µg to about 1000 µg. In another embodiment, the amount administered will be between about 20 µg and about 500 µg. In some embodiments, the amount administered will be between about 75 µg and 250 µg. Greater doses may be administered on the basis of body weight. The exact dosage can be determined by routine dose/response protocols known to one of ordinary skill in the art.

In some embodiments, the amount of conjugates and compositions of the invention that provide an immunologically-effective amount for vaccination against *Klebsiella* and/or *Pseudomonas* infections is from about 1 µg or less to about 100 µg or more. In some embodiments, it is from about 2, 3, 4, 5, 6, 7, 8, 9, 10, 15, 20, 25, 30, 35, 40, 45 or 50 µg to about 55, 60, 65, 70, 75, 80, 85, 90, or 95 µg per kg body weight. In some embodiments, the immunologically-effective amount for vaccination against *Klebsiella* and/or *Pseudomonas* infection is from 0.01 µg to 10 µg.

The conjugates and compositions of the invention may confer resistance to *Klebsiella* and/or *Pseudomonas* infections by either passive immunization or active immunization. In one embodiment of passive immunization, the conjugate or composition is provided to a subject (i.e. a human or mammal), and the elicited antisera is recovered and directly provided to a recipient suspected of having an infection caused by *Klebsiella* and/or *Pseudomonas*.

In some embodiments, the present invention provides a means for preventing or attenuating infection by *Klebsiella* and/or *Pseudomonas* or by organisms which have antigens that can be recognized and bound by antisera to the polysaccharide and/or protein of the conjugate or composition.

The administration of the conjugate or composition (or the antisera which it elicits) may be for either a "prophylactic" or "therapeutic" purpose. When provided prophylactically, the conjugate or composition is provided in advance of any symptom of *Klebsiella* and/or *Pseudomonas* infection. The prophylactic administration of the conjugate or composition serves to prevent or attenuate any subsequent infection. When provided therapeutically, the conjugate or composition is provided upon the detection of a symptom of actual infection. The therapeutic administration of the conjugate or composition serves to attenuate any actual infection.

The conjugate or composition of the invention may, thus, be provided either prior to the onset of infection (so as to prevent or attenuate an anticipated infection) or after the initiation of an actual infection.

The conjugate or composition of the invention may be administered to warm-blooded mammals of any age. The conjugate or composition can be administered as a single dose or in a series including one or more boosters. In some embodiments, the immunization schedule would involve a primary series of three immunizations with a spacing of 1-2 months between the doses. In some settings a booster dose could be administered ~6-12 months later. For example, an infant can receive three doses at 6, 10 and 14 weeks of age (schedule for infants in sub-Saharan Africa) or at 2, 4, and 6 months of life (schedule for U.S. infants). In some embodiments, U.S. infants might receive a booster at 12-18 months of age. Another target population would be U.S. elderly who would likely receive 2-3 doses spaced 1-2 months apart. A further target population would be patients upon admission to a hospital.

Methods of Making the Conjugate

The methods that can be used to make the conjugates of the invention are not limiting. Methods useful for producing conjugate vaccines have been previously described and disclosed in U.S. Pat. Nos. 4,673,574, 4,789,735, 4,619,828, 4,284,537, 5,370,872, 5,302,386, 5,576,002, and U.S. Patent Application Pub. No. 2011/0274714, all of which disclosures are incorporated herein by reference.

In one embodiment, the invention is directed towards a method of making the conjugates described herein comprising binding a *Klebsiella* surface polysaccharide antigen and a *Pseudomonas* flagellin protein or an antigenic fragment or a derivative thereof. In some embodiments, the binding is covalent. In some embodiments, the surface polysaccharide antigen is an O polysaccharide (OPS). Further embodiments include covalently bonding *Pseudomonas aeruginosa* flagellin type A (FlaA) and/or *Pseudomonas aeruginosa* flagellin type B (FlaB) to at least one OPS from *Klebsiella pneumoniae* serovars O1, O2a, O3 and O5 to arrive at the conjugates described herein.

In some embodiments, the surface polysaccharide antigen is isolated from a *Klebsiella pneumoniae* serovar having one or more mutations. For example, the *Klebsiella pneumoniae* may have an attenuating mutation in the guaBA locus and/or a mutation in the wza-wzc locus.

In some embodiments, the *Pseudomonas flagellin* protein is isolated from a heterologous Gram-negative bacteria (GNB) expression system, including *Salmonella* and *Escherichia coli*. In some embodiments, the flagellin protein is isolated from a *Salmonella enterica* serovar strain engineered to express *Pseudomonas aeruginosa* flagellin protein. In some embodiments, the *Salmonella enterica* serovar is *Enteritidis*. In some embodiments, the *Salmonella enterica* serovar strain may have an attenuating mutation, for example, in the guaBA locus. In some embodiments, the flagellin is purified from the bacterial supernatant of the *Salmonella enterica* serovar reagent strains described herein by chromatographic methods.

The *Pseudomonas aeruginosa* flagellin can be purified and isolated using conventional techniques and methods. Such methods can include mechanical shearing, removal at low pH, heating or purification from bacterial supernatants. Methods of purification of a flagellin protein from whole flagella are known in the art or can be readily modified by one of ordinary skill in the art using methods known in the art. For example, by modifying the method of Ibrahim et al., purification of flagella is achieved; below pH 3.0, flagella dissociate into flagellin subunits (Ibrahim et al. *J. Clin. Microbiol.* 1985; 22:1040-4). Further methods for purification include adaptation of the mechanical shearing, and sequential centrifugation steps for purification of flagellin in flagella from bacterial cells.

In some embodiments, COPS and OPS can be isolated by methods including, but not limited to mild acid hydrolysis removal of lipid A from LPS. Other embodiments may include use of hydrazine as an agent for COPS or OPS preparation. Preparation of LPS can be accomplished by known methods in the art. In some embodiments, LPS is prepared according to methods of Darveau et al. *J. Bacteriol.*, 155(2):831-838 (1983), or Westphal et al. *Methods in Carbohydrate Chemistry.* 5:83-91 (1965) which are incorporated by reference herein.

In some embodiments, the LPS is purified by a modification of the methods of Darveau et al., supra, followed by mild acid hydrolysis.

The surface polysaccharide antigen and flagellin can be conjugated using known techniques and methods. For example, techniques to conjugate surface polysaccharide antigen and flagellin can include, in part, coupling through available functional groups (such as amino, carboxyl, thiol and aldehyde groups). See, e.g., Hermanson, Bioconjugate Techniques (Academic Press; 1992); Aslam and Dent, eds. Bioconjugation: Protein coupling Techniques for the Biomedical Sciences (MacMillan: 1998); S. S. Wong, *Chemistry of Protein Conjugate and Crosslinking* CRC Press (1991), and Brenkeley et al., Brief Survey of Methods for Preparing Protein Conjugates With Dyes, Haptens and Cross-Linking Agents, *Bioconjugate Chemistry* 3 #1 (January 1992).

In some embodiments of the present invention, the surface polysaccharide antigen and flagellin or fragments or derivatives thereof, can include functional groups or, alternatively, can be chemically manipulated to bear functional groups. In some embodiments, the presence of functional groups can facilitate covalent conjugation. Such functional groups can include amino groups, carboxyl groups, aldehydes, hydrazides, epoxides, and thiols, for example. Functional amino and sulfhydryl groups can be incorporated therein by conventional chemistry. Primary amino groups can be incorporated by reaction with ethylenediamine in the presence of sodium cyanoborohydride and sulfhydryls may be introduced by reaction of cysteamine dihydrochloride followed by reduction with a standard disulfide reducing agent.

Flagellin may contain amino acid side chains such as amino, carbonyl, hydroxyl, or sulfhydryl groups or aromatic rings that can serve as sites for conjugation. Residues that have such functional groups can be added to either the surface polysaccharide antigen or flagellin. Such residues may be incorporated by solid phase synthesis techniques or recombinant techniques, for example.

Surface polysaccharide antigen and flagellin can be chemically conjugated using conventional crosslinking agents such as carbodiimides. Examples of carbodiimides are 1-cyclohexyl-3-(2-morpholinyl-(4-ethyl) carbodiimide (CMC), 1-ethyl-3-(3-dimethyaminopropyl) carbodiimide (EDC), and 1-ethyl-3-(4-azonia-44-dimethylpentyl) carbodiimide.

Examples of other crosslinking agents are cyanogen bromide, glutaraldehyde and succinic anhydride. In general, any of a number of homobifunctional agents including a homobifunctional aldehyde, a homobifunctional epoxide, a homobifunctional imidoester, a homobifunctional N-hydroxysuccinimide ester, a homobifunctional maleimide, a homobifunctional alkyl halide, a homobifunctional pyridyl disulfide, a homobifunctional aryl halide, a homobifunctional hydrazide, a homobifunctional diazonium derivative or a homobifunctional photoreactive compound can be used. Also included are heterobifunctional compounds, for example, compounds having an amine-reactive and a sulfhydryl-reactive group, compounds with an amine-reactive and a photoreactive group, and compounds with a carbonyl-reactive and a sulfhydryl-reactive group.

Specific examples of homobifunctional crosslinking agents include the bifunctional N-hydroxysuccinimide esters dithiobis (succinimidylpropionate), disuccinimidyl suberate, and disuccinimidyl tartarate; the bifunctional imidoesters dimethyl adipimidate, dimethyl pimelimidate, and dimethyl suberimidate; the bifunctional sulfhydryl-reactive crosslinkers 1,4-di-[3'-(2'-pyridyldithio) propion-amido]butane, bismaleimidohexane, and bis-N-maleimido-1,8-octane; the bifunctional aryl halides 1,5-difluoro-2,4-dinitrobenzene and 4,4'-difluoro-3,3'-dinitrophenylsulfone; bifunctional photoreactive agents such as bis-[b-(4-azidosalicylamide)ethyl]disulfide; the bifunctional aldehydes formaldehyde, malondialdehyde, succinaldehyde, glutaraldehyde, and adiphaldehyde; a bifunctional epoxied such as 1,4-butaneodiol diglycidyl ether; the bifunctional hydrazides adipic acid dihydrazide, carbohydrazide, and succinic acid dihydrazide; the bifunctional diazoniums o-tolidine, diazotized and bis-diazotized benzidine; the bifunctional alkylhalides N1N'-ethylene-bis(iodoacetamide), N1N'-hexamethylene-bis(iodoacetamide), N1N'-undecamethylene-bis(iodoacetamide), as well as benzylhalides and halomustards, such as ala'-diiodo-p-xylene sulfonic acid and tri(2-chloroethyl)amine, respectively.

Examples of other common heterobifunctional crosslinking agents that may be used include, but are not limited to, SMCC (succinimidyl-4-(N-maleimidomethyl)cyclohexane-1-carboxylate), MBS (m-maleimidobenzoyl-N-hydroxysuccinimide ester), STAB (N-succinimidyl(4-iodacteyl) aminobenzoate), SMPB (succinimidyl-4-(p-maleimidophenyl) butyrate), GMBS (N-(-maleimidobutyryloxy)succinimide ester), MPHB (4-(4-N-maleimidopohenyl) butyric acid hydrazide), M2C2H (4-(N-maleimidomethyl)cyclohexane-1-carboxyl-hydrazide), SMPT (succinimidyloxycarbonyl-a-methyl-a-(2-pyridyldithio)toluene), and SPDP (N-succinimidyl 3-(2-pyridyldithio) propionate). For example, crosslinking may be accomplished by coupling a carbonyl group to an amine group or to a hydrazide group by reductive amination.

In another aspect of the invention, the surface polysaccharide antigen and flagellin can be conjugated through polymers, such as PEG, poly-D-lysine, polyvinyl alcohol, polyvinylpyrollidone, immunoglobulins, and copolymers of D-lysine and D-glutamic acid. Conjugation of the surface polysaccharide antigen and flagellin may be achieved in any number of ways, including involving one or more crosslinking agents and functional groups on the surface polysaccharide antigen and/or flagellin. The polymer can be derivatized to contain functional groups if it does not already possess appropriate functional groups.

In some embodiments, 1-cyano-4-dimethylaminopyridinium tetrafluoroborate (CDAP) conjugation chemistry is used to achieve efficient synthesis of the surface polysaccharide antigen and flagellin conjugates. In some embodiments, 1-cyano-4-dimethylaminopyridinium tetrafluoroborate (CDAP) is used to conjugate OPS-FlaA conjugates and OPS-FlaB conjugates.

In some embodiments, the surface polysaccharide antigen or flagellin is conjugated to a linker prior to conjugation. In some embodiments, the linker is adipic acid dihydrazide (ADH). The present invention contemplates the use of any linker capable of conjugating the surface polysaccharide antigen to flagellin. In some embodiments, the presence of a linker promotes optimum immunogenicity of the conjugate and composition and more efficient coupling. In some embodiments, the linkers separate the two or more antigenic components by chains whose length and flexibility can be adjusted as desired. Between the bifunctional sites, the chains can contain a variety of structural features, including heteroatoms and cleavage sites. In some embodiments, linkers also permit corresponding increases in translational and rotational characteristics of the antigens, increasing access of the binding sites to soluble antibodies. Besides ADH, suitable linkers include, for example, heterodifunctional linkers such as ε-aminohexanoic acid, chlorohexanol dimethyl acetal, D-glucuronolactone and p-nitrophenyl amine. Coupling reagents contemplated for use in the present invention include hydroxysuccinimides and carbodiimides. Many other linkers and coupling reagents known to those of ordinary skill in the art are also suitable for use in the invention. Such compounds are discussed in detail by Dick et al., *Conjugate Vaccines*, J. M. Cruse and R. E. Lewis, Jr., eds., Karger, N.Y., pp. 48-114, hereby incorporated by reference.

In some embodiments, ADH is used as the linker. In some embodiments, the molar ratio of ADH to surface polysaccharide antigen such as OPS in the reaction mixture is typically between about 10:1 and about 250:1. In some embodiments, a molar excess of ADH is used to ensure more efficient coupling and to limit OPS-OPS coupling. In some embodiments, the molar ratio is between about 50:1 and about 150:1. In other embodiments, the molar ratio is about 100:1. Similar ratios of AH-OPS to the flagellin in the reaction mixture are also contemplated. In some embodiments, one ADH per OPS is present in the AH-OPS conjugate.

Other linkers are available and can be used to link two aldehyde moieties, two carboxylic acid moieties, or mixtures thereof. Such linkers include ($C_1$-$C_6$) alkylene dihydrazides, ($C_1$-$C_6$) alkylene or arylene diamines, -aminoalkanoic acids, alkylene diols or oxyalkene diols or dithiols, cyclic amides and anhydrides and the like. For examples, see U.S. Pat. No. 5,739,313, incorporated herein in its entirety.

In some embodiments, conjugation is conducted at a temperature of from about 0° C. to about 5° C. for about 36 to about 48 hours. In one embodiment, conjugation is conducted at about 4° C. for about 36 hours, followed by about an additional 18 to 24 hours at a temperature of from about 20° C. to about 25° C. In another embodiment, conjugation is conducted for about 18 hours at about 20 to 24° C., such that the residual cyanate groups react with water and decompose. Longer or shorter conjugation times and/or higher or lower conjugation temperatures can be employed, as desired. In some embodiments, it is desirable, however, to conduct the conjugation reaction, at least initially, at low temperatures, for example, from about 0° C. to about 5° C., such as about 4° C., so as to reduce the degree of precipitation of the conjugate.

In some embodiments of the invention, conjugation of the surface polysaccharide antigen and flagellin protein is on the terminal amino group of lysine residues. In some embodiments of the invention, conjugation is to cysteine groups. In some embodiments of the invention, conjugation of the surface polysaccharide antigen is to N-terminal serine groups. In some embodiments of the invention, conjugation of the surface polysaccharide antigen to the flagellin is directed towards the C-terminal carboxylic acid group. In some embodiments of the invention, conjugation is to naturally occurring amino acid groups. In other embodiments of the invention, conjugation is to engineered amino acid sequences and residues within the flagellin protein.

In some embodiments of the invention, conjugation of the surface polysaccharide antigen and flagellin is on random free hydroxyl groups on the OPS polysaccharide chain. In some embodiments of the invention, conjugation of the flagellin to the surface polysaccharide antigen and is at the terminal end of the polysaccharide chain.

In some embodiments of the invention, the surface polysaccharide antigen and flagellin reactants contain multiple reactive groups per molecule. In some embodiments, an activated surface polysaccharide antigen molecule can react with and form more than one linkage to more than one flagellin. Likewise, an activated flagellin can react with and form more than one linkage to more than one activated surface polysaccharide antigen. Therefore, in some embodiments, the conjugate product is a mixture of various cross-linked matrix-type lattice structures. For example, a single linkage can be present, or 2, 3, 4, 5, 6, 7, 8, 9, 10, 11, 12, 13, 14, 15, 16, 17, 18, 19, 20, 21, 22, 23, 24, 25, 26, 27, 28, 29, or 30 or more linkages can be present. The average number of linkages between a surface polysaccharide and flagellin antigen can be adjusted, as desired. In some embodiments, the average number of linkages can depend upon the type of OPS polysaccharide, the type of flagellin protein, the conjugation method, the reaction conditions, and the like.

In some embodiments, purification processes such as column chromatography and/or ammonium sulfate precipitation of the conjugate from unconjugated polysaccharide may not be necessary. However, in certain embodiments it can be desirable to conduct one or more purification steps. In some embodiments, after conjugation, the conjugate can be purified by any suitable method. Purification can be employed to remove unreacted polysaccharide, protein, or small molecule reaction byproducts. Purification methods include ultrafiltration, size exclusion chromatography, density gradient centrifugation, hydrophobic interaction chromatography, ammonium sulfate fractionation, ion exchange chromatography, ligand exchange chromatography, immuno-affinity chromatography, polymyxin-b chromatography, and the like, as are known in the art. In some embodiments, the conjugation reactions proceed with higher yield, and generate fewer undesirable small molecule reaction byproducts. Accordingly, in some embodiments no purification may be necessary, or only a minor degree of purification can be desirable. The conjugate or composition of the invention can be concentrated or diluted, or processed into any suitable form for use in pharmaceutical compositions, as desired.

Genetically Engineered Strains

In another embodiment, the invention provides a modified *Klebsiella* that is useful for isolating the surface polysaccharide antigen for use in making the conjugates of the invention. In some embodiments, the modified *Klebsiella* is a modified *Klebsiella pneumonia*. In some embodiments, the modified *Klebsiella* comprises one or more attenuating mutations. In some embodiments, the modified *Klebsiella* has an attenuating mutation in the guaBA locus. In some embodiments, the *Klebsiella* comprises one or more mutations in the wza-wzc locus. In some embodiments, the *Klebsiella pneumoniae* serovar can be O1, O2a, O3, and/or O5. In some embodiments, the *Klebsiella* is *Klebsiella pneumoniae* serovar O1, O2a, O3, or O5 having an attenuating mutation in the guaBA locus and a mutation in the wza-wzc locus.

In some embodiments the guaA gene (NCBI-ProteinID: ABR78243 NCBI-GI: 152971364 NCBI-GeneID: 5339904 UniProt: A6TCC2) of *Klebsiella pneumoniae* comprises SEQ ID NO:5, and encodes guanosine monophosphate synthase.

In some embodiments the guaB gene (NCBI-ProteinID: ABR78244 NCBI-GI: 152971365 NCBI-GeneID: 5339905 UniProt: A6TCC3) of *Klebsiella pneumoniae* comprises SEQ ID NO:6, and encodes inosine 5'-monophosphate dehydrogenase.

In some embodiments the wza gene (NCBI-ProteinID: ABR77930 NCBI-GI: 152971051 NCBI-GeneID: 5340218 UniProt: A6TBF9) of *Klebsiella pneumoniae* comprises SEQ ID NO:7, and encodes capsule export-outer membrane protein.

In some embodiments the wzb gene (NCBI-ProteinID: ABR77929 NCBI-GI: 152971050 NCBI-GeneID: 5340217 UniProt: A6TBF8) of *Klebsiella pneumoniae* comprises SEQ ID NO:8, and encodes protein tyrosine phosphatase.

In some embodiments the K2-wzc gene (NCBI-ProteinID: ABR77928 NCBI-GI: 152971049 NCBI-GeneID: 5340932 UniProt: A6TBF7) of *Klebsiella pneumoniae* comprises SEQ ID NO:9, and encodes tyrosine autokinase.

In another embodiment, the invention provides a modified Gram-negative bacteria (GNB) engineered to express *Pseudomonas* flagellin which can be isolated for use in preparation of the conjugates of the invention. In some embodiments, the Gram-negative bacteria is *Escherichia coli*. In some embodiments, the Gram-negative bacteria is a *Salmonella* such as a *Salmonella enterica* serovar strain. In some embodiments, the *Salmonella enterica* serovar is selected from *Enteritidis, Typhimurium*, and *Paratyphi* A. In some embodiments, the Salmonella *enterica* serovar is *Enteritidis*.

In some embodiments, the Gram-negative bacteria expressing *Pseudomonas* flagellin has one or more mutations. In some embodiments, the Gram-negative bacteria has one or more mutations in the guaBA locus, the guaB gene, the guaA gene, the clpP gene, the clpX gene and/or the clpPX locus. In some embodiments, the Gram-negative bacteria expressing *Pseudomonas* flagellin has one or more codon optimized *Pseudomonas* fliC genes. In some embodiments, the Gram-negative bacteria expressing *Pseudomonas* flagellin encodes a excretion signal for flagellin.

In some embodiments, the Gram-negative bacteria, such as *Salmonella enterica*, has at least one attenuating mutation in the guaBA locus and/or the clpPX locus. In some embodiments, one or more of guaBA, clpPX and fliD are mutated to create highly attenuated strains that hyper-secrete flagellin monomers into the supernatant. A guaBA mutation (involved in guanosine nucleotide synthesis (Samant S et al., *PLoS Pathog.* 2008; 4(2):e37)) is highly attenuating in several Gram negative pathogens (e.g., *Shigella* (Kotloff K L et al., *Hum Vaccin.* 2007; 3(6):268-275), *Salmonella* (Tennant S M et al., *Infect Immun.* 2011; 79(10):4175-4185; Gat O et al., *PLoS Negl Trop Dis.* 2011; 5(11):e1373), *Francisella* (Santiago A E et al., *Vaccine.* 2009; 27(18): 2426-2436)). When either clpP or clpX (that form the ClpPX protease) is deleted, the master flagella regulator complex FlhD/FlhC is not degraded and large amounts of flagella are produced. Deletion of clpPX is also independently attenuating (Tennant S M et al., *Infect Immun.* 2011; 79(10):4175-4185; Tomoyasu T et al., *J Bacteriol.* 2002; 184(3):645-653). Deletion of the gene for the flagella capping protein FliD causes flagellin monomers to be exported into the supernatant, and engineered *Salmonella* mutants deficient in clpPX and fliD produce and export large amounts of flagellin into the culture supernatant. These recombinant strains are considered as safe from an occupational health and safety perspective and enable conjugate vaccine carrier proteins to be expressed at high levels, thus lowering the overall cost of manufacture.

Growth conditions in fully chemically defined minimal media for attenuated *S. Enteritidis* and *S. Typhimurium* strains have been established, whereby an optical density at 600 nm ($OD_{600}$) of 15-18 is consistently attained at 20 L fermentation scale. Prototype attenuated *S. Enteritidis* reagent strain CVD 1943 ΔguaBA ΔclpP ΔfliD was constructed from wild-type strain *S. Enteritidis* R11 (a Malian clinical isolate) (Richmond P, *J Infect Dis.* 2000; 181(2): 761-764).

In some embodiments, the Gram negative bacteria has an inactivating mutation in fliC such as a deletion in fliC. Such strain may further have an inserted (either in the chromosome or on a plasmid) heterologous fliC such as fliC from *Pseudomonas aeruginosa* or a bacteria producing flagellin with cross-reactivity to fliC from *Pseudomonas aeruginosa.*

In some embodiments, the Gram negative bacteria is *Salmonella enterica* having a mutation in fliC and having a plasmid encoding *Pseudomonas aeruginosa* Type A flagellin (FlaA) and/or *Pseudomonas aeruginosa* Type B flagellin (FlaB). In some embodiments, the amino acid sequence of FlaA comprises SEQ ID NO:1 and the nucleotide sequence of FlaA comprises SEQ ID NO:3. In some embodiments, the amino acid sequence of FlaB comprises SEQ ID NO:2 and the nucleotide sequence comprises SEQ ID NO:4. In some embodiments, the *Salmonella enterica* expressing *Pseudomonas* flagellin has one or more codon optimized *Pseudomonas* fliC genes. In some embodiments, the *Salmonella enterica* expressing *Pseudomonas* flagellin encodes a *Salmonella enterica Enteritidis* fliC excretion signal.

In some embodiments, the Gram negative bacteria hyper-secretes *Pseudomonas* flagellin. In some embodiments, the Gram negative bacteria comprises a clpP or clpX (that form the ClpPX protease) mutation causing the master flagella regulator complex FlhD/FlhC to not be degraded, thereby causing the production of large amounts of flagella.

In some embodiments, using modified strains with attenuating mutations can simplify purification. Attenuated *Salmonella* strains are considered as safe from an occupational health and safety perspective. As used herein, attenuated strains are those that have a reduced, decreased, or suppressed ability to cause disease in a subject, or those completely lacking in the ability to cause disease in a subject. Attenuated strains may exhibit reduced or no expression of one or more genes, may express one or more proteins with reduced or no activity, may exhibit a reduced ability to grow and divide, or a combination of two or more of these characteristics.

In some embodiments, the attenuated strains producing *Pseudomonas* flagellin of the invention have a mutation in one or more of the guaBA locus, the guaB gene, the guaA gene, the clpP gene, the clpX gene and the clpPX locus. For example, the attenuated strains can have a mutation (i) in the guaB gene and the clpP gene, (ii) in the guaA gene and the clpP gene, (iii) in the guaBA locus, and the clpP gene, (iv) in the guaB gene and the clpX gene, (v) in the guaA gene and the clpX gene, (vi) in the guaBA locus, and the clpX gene, (vii) in the guaB gene and the clpPX locus, (viii) in the guaA gene and the clpPX locus, or (ix) in both the guaBA locus and the clpPX locus.

In some embodiments, attenuated strains are prepared having inactivating mutations (such as chromosomal deletions) in both the guaBA locus (encoding enzymes involved in guanine nucleotide biosynthesis) and the clpPX locus (encoding an important metabolic ATPase) genes. In some embodiments, one or more of the attenuated strains also have fliD and fliC mutations.

The mutations of the loci and genes described herein can be any mutation, such as one or more nucleic acid deletions, insertions or substitutions. The mutations can be any deletion, insertion or substitution of the loci or genes that results in a reduction or absence of expression from the loci or genes, or a reduction or absence of activity of a polypeptide encoded by the loci or genes. The mutations may be in the coding or non-coding regions of the loci or genes.

In some embodiments, the chromosomal genome of the Gram negative bacteria or *Klebsiella* is modified by removing or otherwise modifying the guaBA locus, and thus blocking the de novo biosynthesis of guanine nucleotides. In some embodiments, a mutation in the guaBA locus inactivates the purine metabolic pathway enzymes IMP dehydrogenase (encoded by guaB) and GMP synthetase (encoded by guaA). In some embodiments, the strains are unable to de novo synthesize GMP, and consequently GDP and GTP nucleotides, which severely limits bacterial growth in mammalian tissues. The AguaBA mutants of the present invention are unable to grow in minimal medium unless supplemented with guanine.

In some embodiments, the guaA gene of *S. Enteritidis*, which encodes GMP synthetase, is 1578 bp in size (GenBank Accession Number NC_011294.1 (2623838-2625415) (SEQ ID NO:10). In some embodiments, the guaA gene of *S. Typhimurium*, is 1578 bp in size (GenBank Accession Number NC_003197.1 (2622805..2624382, complement) (SEQ ID NO:11). In some embodiments, the guaA gene of *S. Typhi*, is 1578 bp in size (GenBank Accession Number NC_004631.1 (415601..417178) (SEQ ID NO:12). In some embodiments, the guaA gene of *S. Paratyphi* A, is 1578 bp in size (GenBank Accession Number NC_006511.1 (421828..423405) (SEQ ID NO:13). In some embodiments, the guaA gene of *S. Paratyphi* B is 1578 bp in size (GenBank Accession Number NC_010102.1 (418694..420271) (SEQ ID NO:14).

Deletion mutants can be produced by eliminating portions of the coding region of the guaA gene so that proper folding or activity of GuaA is prevented. For example, about 25 to about 1500 bp, about 75 to about 1400 bp, about 100 to about 1300 bp, or all of the coding region can be deleted. Alternatively, the deletion mutants can be produced by eliminating, for example, a 1 to 100 bp fragment of the guaA gene so that the proper reading frame of the gene is shifted. In the latter instance, a nonsense polypeptide may be produced or polypeptide synthesis may be aborted due to a frame-shift-induced stop codon. The preferred size of the deletion removes both guaB and guaA, from the ATG start codon of guaB to the stop codon of guaA.

In some embodiments, the guaB gene of *S. Enteritidis* which encodes IMP dehydrogenase, is 1467 bp in size (GenBank Accession Number NC_011294.1 (2625485-2626951, complement) (SEQ ID NO:15). In some embodiments, the guaB gene of *S. Typhimurium* is 1467 bp in size (GenBank Accession Number NC_003197.1 (2624452..2625918, complement) (SEQ ID NO:16). In some embodiments, the guaB gene of *S. Paratyphi* A is 1467 bp in size (GenBank Accession Number NC_006511.1 (420292..421758) (SEQ ID NO:17). Deletion mutants can be produced by eliminating portions of the coding region of the guaB gene so that proper folding or activity of GuaB is prevented. For example, about 25 to about 1400 bp, about 75 to about 1300 bp, about 100 to about 1200 bp, or all of the coding region can be deleted. Alternatively, the deletion mutants can be produced by eliminating, for example, a 1 to 100 bp fragment of the guaB gene so that the proper reading frame of the gene is shifted. In the latter instance, a nonsense polypeptide may be produced or polypeptide synthesis may be aborted due to a frame-shift-induced stop codon. The preferred size of the deletion removes both guaB and guaA, from the ATG start codon of guaB to the stop codon of guaA.

In some embodiments, the clpP gene of *S. Enteritidis*, which encodes a serine-protease, is 624 bp in size (GenBank Accession Number NC_011294.1 (482580-483203) (SEQ ID NO:18). In some embodiments, the clpP gene of *S. Typhimurium* is 624 bp in size (GenBank Accession Number NC_003197.1 (503210..503833) (SEQ ID NO:19). In some embodiments, the clpP gene of *S. Paratyphi* A is 624 bp in size (GenBank Accession Number NC_006511.1 (2369275.2369898, complement) (SEQ ID NO:20).

Deletion mutants can be produced by eliminating portions of the coding region of the clpP gene so that proper folding or activity of ClpP is prevented. For example, about 25 to about 600 bp, about 75 to about 500 bp, about 100 to about 400 bp, or all of the coding region can be deleted. Alternatively, the deletion mutants can be produced by eliminating, for example, a 1 to 100 bp fragment of the clpP gene so that the proper reading frame of the gene is shifted. In the latter instance, a nonsense polypeptide may be produced or polypeptide synthesis may be aborted due to a frame-shift-induced stop codon. clpP forms an operon with clpX; the preferred size of the deletion encompasses only the downstream clpX gene and extends from the ATG start codon to the stop codon, inclusive.

In some embodiments, the clpX gene of *S. Enteritidis*, which encodes a chaperone ATPase, is 1272 bp in size (GenBank Accession Number NC_011294.1 (483455-484726) (SEQ ID NO:21). In some embodiments, the clpX gene of *S. Typhimurium* is 1272 bp in size (GenBank Accession Number NC_003197.1 (504085..505356) (SEQ ID NO:22). In some embodiments, the clpX gene of *S. Paratyphi* A is 1272 bp in size (GenBank Accession Number NC_006511.1 (2367752..2369023, complement) (SEQ ID NO:23).

Deletion mutants can be produced by eliminating portions of the coding region of the clpX gene so that proper folding or activity of ClpX is prevented. For example, about 25 to about 1200 bp, about 75 to about 1100 bp, about 100 to about 1000 bp, or all of the coding region can be deleted. Alternatively, the deletion mutants can be produced by eliminating, for example, a 1 to 100 bp fragment of the clpX gene so that the proper reading frame of the gene is shifted. In the latter instance, a nonsense polypeptide may be produced or polypeptide synthesis may be aborted due to a frame-shift-induced stop codon. clpP forms an operon with clpX; the preferred size of the deletion encompasses only the downstream clpX gene and extends from the ATG start codon to the stop codon, inclusive.

The fliC gene can be mutated using conventional techniques known in the art. The fliC gene encodes a flagellin protein. In some embodiments, the fliC gene from *S. Enteritidis* is 1518 bp in size (GenBank Accession Number NC_011294.1 (1146600..1148117) (SEQ ID NO:24). In some embodiments, the fliC gene of *S. Typhimurium* is 1488 bp in size (GenBank Accession Number NC_003197.1 (2047658..2049145, complement) (SEQ ID NO:25). In some embodiments, the fliC gene of *S. Paratyphi* A, is 1488 bp in size (GenBank Accession Number NC_006511.1 (989787..991274) (SEQ ID NO:26).

In some embodiments, deletions can be made in any of the loci or genes included herein by using convenient restriction sites located within the loci or genes, or by site-directed mutagenesis with oligonucleotides (Sambrook et al., *Molecular Cloning, A Laboratory Manual*, Eds., Cold Spring Harbor Publications (1989)).

In some embodiments, inactivation of the loci or genes can also be carried out by an insertion of foreign DNA using any convenient restriction site, or by site-directed mutagenesis with oligonucleotides (Sambrook et al., supra) so as to interrupt the correct transcription of the loci or genes. The typical size of an insertion that can inactivate the loci or genes is from 1 base pair to 100 kbp, although insertions smaller than 100 kbp are preferable. In some embodiments, the insertion can be made anywhere inside the loci or gene coding regions or between the coding regions and the promoters. In some embodiments, the bacterial loci and genes are mutated using Lambda Red-mediated mutagenesis (see, e.g., Datsenko and Wanner, *PNAS USA* 97:6640-6645 (2000)).

While the invention has been described with reference to certain particular examples and embodiments herein, those skilled in the art will appreciate that various examples and embodiments can be combined for the purpose of complying with all relevant patent laws (e.g., methods described in specific examples can be used to describe particular aspects of the invention and its operation even though such are not explicitly set forth in reference thereto).

EXAMPLES

Example 1

Preparation and Testing of Conjugates Comprising Surface Polysaccharides and Flagellin Proteins Reagent Strain to Purify Heterologous Flagellins—

We have created a recombinant reagent strain that can be used to purify large amounts of heterologous flagellin by deleting fliC from the *S. Enteritidis* reagent strain CVD 1943. The new reagent strain *S. Enteritidis* R11 ΔguaBA ΔclpP ΔfliD ΔfliC is designated CVD 1947. Heterologous fliC genes can subsequently be cloned into pGEN206 (Stokes M G et al., *Infection and Immunity,* 2007; 75(4): 1827-1834), a low copy number highly stable plasmid and introduced into CVD 1947.

Development of Scalable Upstream and Downstream Bioprocesses for Obtaining Purified Flagellins and OPS—

Robust, scalable, high yield and generalized purification methods have been developed to purify OPS and flagellins. We have developed and confirmed broadly applicable and scalable downstream manufacturing processes to purify secreted flagellins from culture supernatants, and OPS from bacterial cells using common bioprocess methods and equipment. We have also confirmed performance at 20 L scale for two different *Salmonella* serovar (*Typhimurium* and *Enteritidis*) where we can reliably purify to near homogeneity >150 mg of flagellin/L of supernatant, and ~3 mg of COPS/g wet cell paste. By using fully chemically defined medium that does not contain any exogenous biological material (e.g., peptides, proteins), all biological components originate from the bacterial strain, thus further simplifying flagellin purification. Notably, we have found that secreted flagellin represents the major (>90%) detectable protein species in fermentation culture supernatant (FIG. 4). For flagellin purification, protein can be purified by an initial capture directly from fermentation supernatants onto cation exchange membranes. A secondary anion exchange purification step, coupled with a final tangential flow filtration step for buffer exchange and size selection, are sufficient to yield highly pure FliC (>500 mg/L from fermentation culture) with very low endotoxin levels (<0.1 EU/μg), and no detectable residual nucleic acid. COPS extraction can be accomplished by a series of organic extraction steps coupled with ion exchange chromatography, TFF and ammonium sulfate precipitation steps, and purified to near homogeneity at a yield of ~3 mg COPS/g wet cell paste (FIG. 4). We have successfully used these bioprocess schemes to purify FliC flagellins from *Salmonella* serovars *Typhimurium, Enteritidis* and *Typhi*, and COPS from *S. Typhimurium* and *S. Enteritidis.* fication with hydrazides, at random COPS hydroxyl groups along the polysaccharide chain using 1-Cyano-4-dimethylaminopyridinium tetrafluoroborate (CDAP), generating a lattice-type conjugate (FIG. 5, lane 4). End-linked sun-type conjugates have also been generated by conjugating at the carbonyl group present in the COPS ketocidic terminus with amino-oxime thioether chemistry to Sulfo-GMBS (N-[γ-maleimidobutyryloxy]sulfosuccinimide ester) modified protein lysines (FIG. 5, lane 5). Removal of unconjugated components and conjugation reagents can be accomplished by a 2-step purification approach developed at the Center for Vaccine Development (CVD), separating first by size with size-exclusion chromatography (SEC) and then by charge using ion-exchange chromatography membranes. These conjugation methods have all been used successfully for the homologous COPS and flagellins from *S. Enteritidis* and *S. Typhimurium.*

Immunogenicity of *Salmonella* COPS:Flagellin Conjugates in Mice—

BALB/c mice immunized intramuscularly at days 0, 28 and 56 with 2.5 μg of *S. Enteritidis* COPS polysaccharide conjugated to *S. Enteritidis* FliC produced significant levels of LPS and FliC specific serum IgG antibody titers above the PBS controls. Immunization with unconjugated COPS alone or admixed with flagellin failed to produce anti-LPS IgG (FIG. 6). Importantly, mice immunized with COPS:FliC produced anti-FliC IgG titers that were similar to those of mice immunized with COPS admixed with flagellin, suggesting that conjugation does not interfere with anti-flagellin immune responses. Post-vaccination COPS:FliC sera recognized LPS and FliC (FIG. 7), and sera from mice immunized with flagellin alone bound to *Salmonella*-associated flagella (FIG. 8). We further determined that *S. Enteritidis* COPS:FliC conjugates synthesized by either coupling at random polysaccharide hydroxyls via CDAP, or end-coupling at the terminal KDO carbonyl by aminooxy (oxime) chemistry generated similar levels of anti-LPS and anti-FliC serum IgG, and comparably protected against fatal IP challenge with *S. Enteritidis* R11 (TABLE 1).

TABLE 1

Immunogenicity of COPS:FliC conjugate vaccines in CD-1 mice and protective efficacy against lethal challenge with wild-type *S. Enteritidis* R11[a]

| Vaccine | Anti-FliC GMT (EU[d]/ml) | Anti-FliC Seropositive[b] | Anti-LPS GMT (EU/ml) | Anti-LPS Seropositive[b] | Mortality[c] (dead/total) | Vaccine Efficacy |
|---|---|---|---|---|---|---|
| PBS | 101 | 0 | 82 | 0 | 12/13 | — |
| COPS:FliC CDAP | 8,735,020 | 100% | 223 | 39% | 3/13[d] | 75.0% |
| COPS:FliC Oxime | 9,548,869 | 100% | 392 | 40% | 2/13[d] | 83.3% |

[a]IP $LD_5 \times 10^5$ CFU.
[b]Defined as ≥4-fold the GMT in mice immunized with PBS
[c]Mice challenged i.p. with $1 \times 10^6$ CFU
[d]$p < 0.001$ vs. PBS control animals by Fisher's exact test.
[d]ELISA Units Development of Methods to Conjugate OPS with Flagellin—

We have developed several methods that can be used to simply and reliably conjugate OPS with carrier proteins, and generate different types of conjugates. *Salmonella* COPS was successfully conjugated directly to the ε-amino groups of flagellin lysines or to carboxylic acid groups after modi- We also examined the effect of different COPS:FliC conjugate vaccine doses on immunogenicity and efficacy (Chu C Y, *Infect Immun.* 1991; 59(12):4450-4458). Maximal levels of anti-flagellin IgG and 100% seroconversion (≥4-fold vs. PBS geometric mean titers [GMT]) were achieved at doses ≥0.25 μg of COPS:FliC. Mice immunized at the lowest dose of 0.025 μg COPS:FliC also displayed a significantly higher GMT of anti-FliC IgG compared to mice receiving PBS, but with sub-maximal levels and several animals failing to produce detectable anti-FliC IgG (75% seropositive). We further observed that anti-flagellin IgG end-point titers were significantly higher than anti-LPS IgG levels in COPS:FliC immunized mice at all doses tested. Immunization with COPS:FliC doses of 10 µg and 2.5 µg elicited GMT's of 885 EU/ml and 308 EU/ml respectively, whereas immunization with doses of 0.25 and 0.025 µg resulted in GMT's of <80 EU/ml. Notably, whereas infection with $1\times10^6$ CFU of *S. Enteritidis* caused 100% mortality in the PBS control group, mice immunized with 0.025 µg, 0.25 µg, 2.5 µg or 10 µg of COPS:FliC were all significantly protected (≥90% vaccine efficacy). We also found that conjugation can reliably reduce TLR5 stimulatory capacity, and that TLR5 activity was dispensable for immunogenicity. Our findings are in agreement with those reported for flagellin immunization experiments in TLR5-deficient mice, where anti-flagellin titers obtained were comparable to wild-type mice (Sanders C J et al., *Eur J Immunol.* 2009; 39(2):359-371). Vaxinnate Corporation has reported measurable rates of adverse events at low dosage levels for their TLR5 stimulatory flagellin-based fusion proteins with influenza antigens (Turley C B et al., *Vaccine.* 2011; 29(32): 5145-5152). Hence, we will aim to abolish TLR5 activity in our conjugates, as we have successfully done previously (Simon R, *Infect Immun.* 2011; 79(10):4240-4249).

Functional Activity of Vaccine Induced Antibodies—

I. Opsonophagocytosis.

Figure 9:
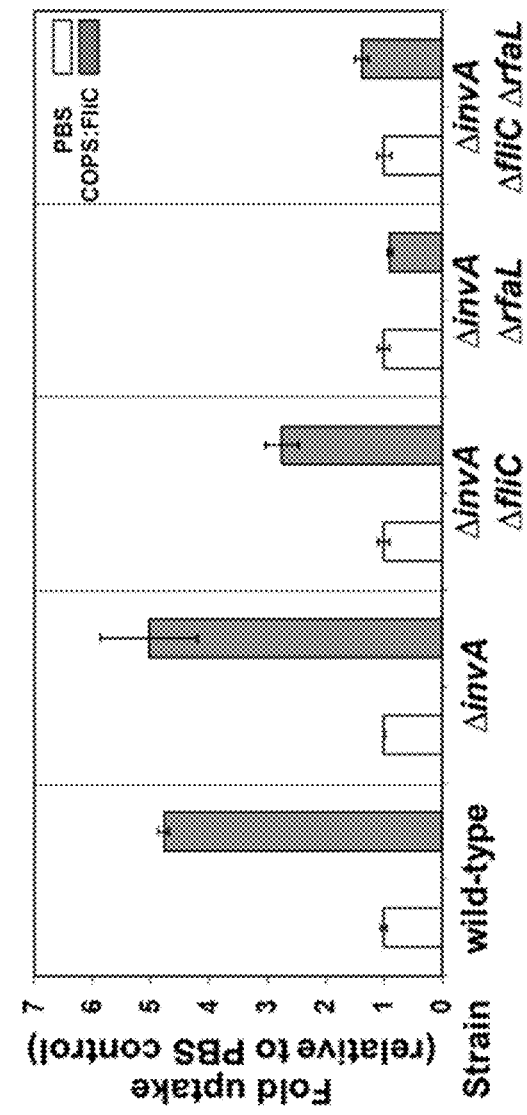
FIG. 9. Opsonophagocytic uptake of wild-type *S. Enteritidis* R11 by J774 mouse macrophages exposed to sera from mice immunized with COPS conjugates. Uptake of wild-type *S. Enteritidis* R11 and derivatives mutated in invA, fliC, and rfaL in the presence of pooled sera from mice immunized with COPS:FliC conjugate relative to sera from mice receiving PBS.

Pooled sera from mice immunized with COPS:FliC were able to cause uptake of wild-type and invA (invasion)-deficient *S. Enteritidis* R11 into J774 cultured mouse macrophage cells. Uptake was reduced in the absence of bacterial expression of either flagellin (ΔfliC) or long-chain OPS (ΔrfaL) components present in the vaccine (FIG. 9) indicating that COPS:FliC vaccines induce opsonophagocytic antibody to both components.

II. Passive Transfer.

Passive immunization of naïve mice with sera from mice immunized with 10 µg of COPS:FliC produced >80% protection against lethal *S. Enteritidis* challenge, whereas mice receiving normal sera or PBS succumbed to infection, demonstrating that protection can be mediated in vivo by vaccine induced antibodies (TABLE 2).

TABLE 2

Efficacy of passive transfer into naive mice of sera from mice immunized with COPS:FliC. Protection of mice from lethal challenge with wild-type *S. Enteritidis* R11[a]

| Treatment | Mortality (dead/total) |
|---|---|
| PBS | 5/6 |
| Normal serum | 7/7 |
| COPS:FliC serum | 1/7[b] |

[a]Mice challenged IP with $5 \times 10^5$ CFU
[b]p = 0.005 compared to normal serum by 2-tailed Fisher's exact test.

Development of Opsonophagocytic Antibody (OPA) Assays—

Figure 10:
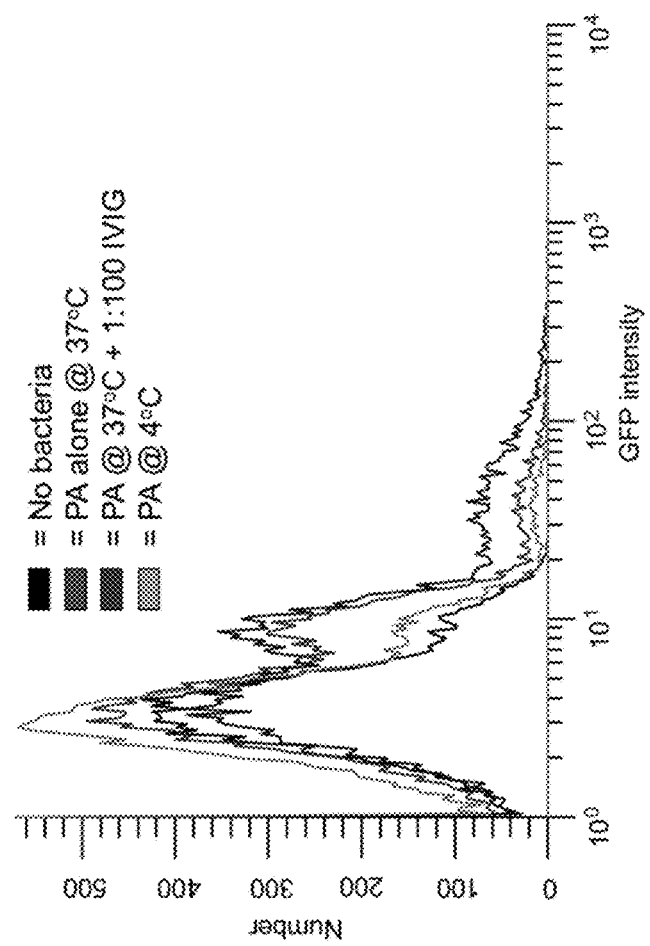
FIG. 10. Flow cytometric assay for the uptake of PA by human polymorphonuclear leukocytes (PMNs). GFP-expressing strain PAO1 was added to PMNs (MOI=5) in the presence (blue line) or absence (red line) of IVIG enriched in antibodies to PA and KP (Cryz S J et al., *J Infect Dis.* 1991; 163(5):1055-1061). PA were spun onto PMNs at 4° C., washed, and incubated for 15 min at 37° C. PMNs were then washed, incubated for 15 min in gentamicin (50 μg/ml), washed and resuspended for analysis.
Figure 11:
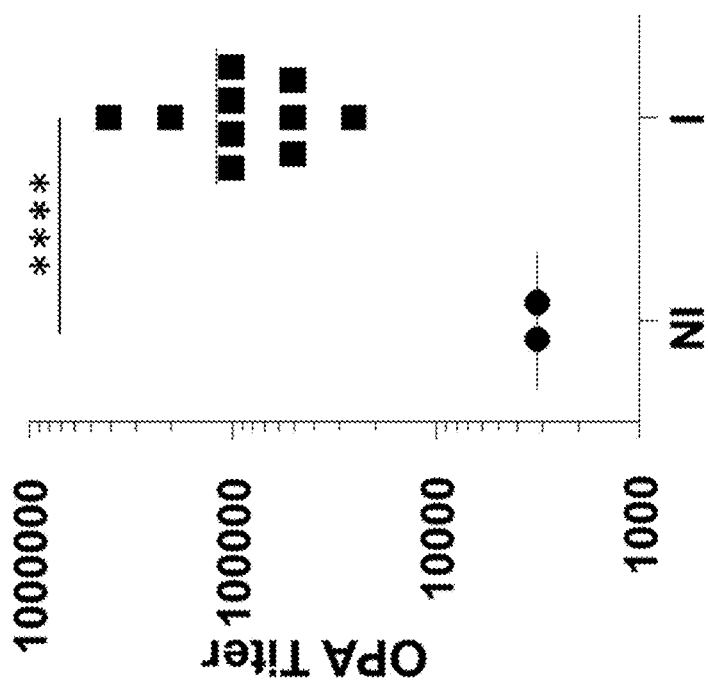
FIG. 11. Endpoint OPA titers for mice immunized with live attenuated *S. Typhimurium* CVD 1931. Line indicates mean titers. I, Immune; NI, Non-immune serum. ****, P<0.0001 by Mann-Whitney test.

We have developed and validated a high-throughput flow cytometry based OPA uptake assay using GFP-expressing PA (FIG. 10). We have also successfully adapted an opsonophagocytic assay that is widely used to evaluate pneumococcal capsular polysaccharide vaccines (Romero-Steiner S et al., *Clin Diagn Lab Immunol.* 1997; 4(4):415-422) to measure functional antibodies elicited by *S. Typh-imurium* vaccines. This assay uses baby rabbit complement as a complement source and HL-60 cells as phagocytes. The OPA titer is defined as the titer of sera that results in greater than 50% killing of bacteria following opsonophagocytosis. As shown in FIG. 11, OPA titers for sera from mice orally immunized with the live attenuated *S. Typhimurium* vaccine CVD 1931 (ΔguaBA ΔclpX) were significantly higher than for mice immunized with PBS.

Engineering Bacteria so that Large Amounts of PA Flagellin and O Polysaccharides (OPS) can be Purified Safely and Economically—

Large-scale fermentation using wild-type pathogenic KP bacteria to manufacture COPS constitutes a significant occupational health hazard. The use of attenuated and avirulent strains from which to purify polysaccharide vaccine antigens markedly decreases these risks, and such a strategy is already being implemented for new generation *S. Typhi* Vi polysaccharide based vaccines (Micoli F et al., *Vaccine.* 2012; 30(5):853-861). Precise deletions in select metabolic and virulence genes of several GNB pathogens have resulted in attenuated strains useful as live oral vaccines (Tennant S M et al., *Infect Immun.* 2011; 79(10):4175-4185; Tacket C O, Levine M M et al., *Clin Infect Dis.* 2007; 45 Suppl 1:S20-23). We have experience in constructing such attenuated vaccine strains and in demonstrating their clinical acceptability, safety and immunogenicity in animal models and in human clinical trials (Inaba S et al., *Biopolymers.* 2013; 99(1):63-72; Kotloff K L et al., *Hum Vaccin.* 2007; 3(6): 268-275). We have had success using a guaBA mutation (Samant S et al., *PLoS Pathog.* 2008; 4(2):e37) as the primary attenuating mutation in live attenuated Shigella vaccines where safety has been documented in clinical trials (Kotloff K L et al., *Hum Vaccin.* 2007; 3(6):268-275). A Phase 1 clinical trial conducted at the CVD has also shown that *S. Paratyphi* A CVD 1902 (which possesses deletions in guaBA and clpX) was safe and well-tolerated in human volunteers including at the highest dosage levels tested ($10^{10}$ CFU)(Levine M M., Paper presented at: 8th International conference on typhoid fever and other invasive Salmonelloses 2013; Dhaka, Bangladesh). Because *Pseudomonas aeruginosa* expresses a solitary unipolar flagellum, the level of flagellin expression on *Pseudomonas aeruginosa* is insufficient for large scale production. Genetically engineered attenuated strains can improve the safety of large-scale manufacture of *Klebsiella pneumoniae* OPS and can provide a means for enhanced *Pseudomonas aeruginosa* flagellin expression. Thus, we have created recombinant reagent strains that can be used to purify large amounts of *Klebsiella pneumoniae* OPS and PA flagellin.

Research Design for KP and PA Strains—

Genetically engineered *Klebsiella pneumoniae* reagent strains are created to improve occupational safety for large scale fermentation, and simplify and enhance OPS purification and yields. GuaBA from *K. pneumoniae* O1, O2, O3 and O5 strains is deleted using lambda red recombination (Datsenko K A, Wanner B L., *Proc Natl Acad Sci USA.* Jun. 6 2000; 97(12):6640-6645). Capsule synthesis (cps) gene cluster is deleted from the four guaBA mutants. CPS mutation serves two purposes: 1) It is a secondary independently attenuating mutation that safeguards against the possibility of reversion to virulence; and 2) purification of core-O polysaccharide will be simpler as there will be no contaminating capsular polysaccharide.

The genes encoding PA flagellins FlaA and FlaB are cloned into pSEC10, a highly stable low copy number plasmid, and then transform the plasmids into our *S. Enteritidis* reagent strain CVD 1947. The reagent strains grow in chemically defined minimal media and secrete large amounts of PA flagellin is confirmed by performing SDS-PAGE and western blots of culture supernatant.

Reagents strains are grown in 5 L fermentation culture, as optimization at this scale is generally translatable to larger volumes (e.g., 50 L-1,000 L). KP reagent strain fermentation is optimzed with rich media to supply an optimal environment for growth, making use of animal product free formulation to comply with FDA regulations for biologics. PA-Fla CVD 1947 expression vectors is grown in fully chemically defined minimal media to reduce the contaminant background, as the PA-Fla product will be in the supernatant. KP OPS and PA-Fla purification is conducted with previously optimized biochemical purification protocols that we developed for *Salmonella* COPS and FliC. Products are tracked through the process using standardized assays, and are verified to meet the following release parameters

TABLE 3

TABLE 3. Lot release parameters for purified KP COPS and PA flagellins

| Parameter | COPS limit (assay) | Flagellin limit (assay) |
|---|---|---|
| Residual host cell protein | <1% (BCA) | <1% (HPLC-SEC with UV, SDS-PAGE) |
| Residual nucleic acid | <1% (A260 nm) | <1% (Quant-IT) |
| Residual endotoxin | <150 EU/µg (LAL) | <150 EU/µg (LAL) |
| Identity | Conform to standards (HPAEC-PAD, ELISA) | Expected size by Western blot |
| Size/Weight | HPLC-SEC with RI | HPLC-SEC with UV, SDS-PAGE |

Construction of *K. pneumoniae* Reagent Strains—

We genetically engineered *Klebsiella pneumoniae* reagent strains to improve occupational safety for large scale fermentation, and simplify and enhance COPS purification and yields. We deleted guaBA from *K. pneumoniae* O1, O2, O3 and O5 strains using lambda red recombination. We also deleted the capsule synthesis (cps) gene cluster from the four guaBA mutants. CPS mutation will serve two purposes: 1) It is a secondary independently attenuating mutation that safeguards against the possibility of reversion to virulence; and 2) purification of core-O polysaccharide will be simpler as there will be no contaminating capsular polysaccharide.

We used lambda red recombination to delete guaBA (for attenuation) and the capsule (cps) gene cluster from the following KP strains: B5055 (O1:K2), 7380 (O2ab:K-), 390 (O3:K11) and 4425/51 (O5:K7). We have genetically engineered the B5055 (O1) and 7380 (O2ab) *Klebsiella* strains and have deleted guaBA and cps genes, as necessary. We have also created the 390 (O3) ΔguaBA mutant. See Table 4.

TABLE 4

CVD genetically engineered KP reagent strains

| Strain designation | Parent strain | O type | K type | guaBA | CPS | Notes |
|---|---|---|---|---|---|---|
| CVD 3000 | B5055 | 1 | 2 | — | + | Completed |
| CVD 3001 | B5055 | 1 | 2 | — | − | Completed |
| CVD 3010 | 7380 | 2 | — | — | Naturally Deficient | Completed |
| CVD 3020 | 4425 | 5 | 57 | — | − | In progress |
| CVD 3030 | 390 | 3 | 11 | — | − | In progress |

The primers used for the genetic engineering are shown in Table 5:

| Name | Target | Purpose | Primer sequences (5'->3') |
|---|---|---|---|
| guaBA_676_F | B5055 | ΔguaBA | GGGTAGATGATCACCGGCAG (SEQ ID NO: 27) |
| guaBA_688_R | B5055 | ΔguaBA | TGATTGGTCTGACTGGACGC (SEQ ID NO: 28) |
| guaBA_155_R | B5055 | ΔguaBA | GGAAGCCAGTGGGATCTGAC (SEQ ID NO: 29) |
| guaBA_256_F | B5055 | ΔguaBA | CTGATCCAAACCTGGCCCAT (SEQ ID NO: 30) |
| guamut_F | B5055 | ΔguaBA | GGTCGACGGATCCCCGGAATGGAGTAATCCCCGGCGTTAG (SEQ ID NO: 31) |
| guamut_R | B5055 | ΔguaBA | GAAGCAGCTCCAGCCTACACGGGCAATATCTCGACCAGGG (SEQ ID NO: 32) |
| guaA_R2 | 390-4425/51-7380 | ΔguaBA | CATACACCACGCGGGAGATA (SEQ ID NO: 33) |
| guaA_mut_F2 | 390-4425/51-7380 | ΔguaBA | GGTCGACGGATCCCCGGAATGCTAGCCGCGTTTTCGTGGAAGTG (SEQ ID NO: 34) |
| guaB_F2 | 390-4425/51-7380 | ΔguaBA | GTCCTCCTCGTTCCCGCT (SEQ ID NO: 35) |
| guaB_mut_R2 | 390-4425/51-7380 | ΔguaBA | GAAGCAGCTCCAGCCTACACGAATTCCATCTTTACAGGCGTTCGGT (SEQ ID NO: 36) |
| wza_F | B5055 4425/51 wza | Δwzabc | GAGCCGACTCTAGGGTGGC (SEQ ID NO: 37) |
| wza_R | B5055-390-4425/51 wza | Δwzabc | GAAGCAGCTCCAGCCTACACTAATGTCACATCATCAGTAAATCAAATTTG (SEQ ID NO: 38) |
| K2_wzc_F | B5055 wzc | Δwzabc | GAAGCAGCTCCAGCCTACACGTAATAGATATGTTATAGAGTTTGGAGGGGAG (SEQ ID NO: 39) |
| K2_wzc_R | B5055 wzc | Δwzabc | TATTTAATTTCCCTCTTTCATCCTGTAATGTT (SEQ ID NO: 40) |
| K11_wzc_F | 390 wzc | Δwzabc | GGTCGACGGATCCCCGGAATTGTTTCAAGATTATATATTTCGATGCCTAATG (SEQ ID NO: 41) |
| K11_wzc_R | 390 wzc | Δwzabc | TCCTTAGTATAAAGTTGAGAGATTTCTGATTC (SEQ ID NO: 42) |
| K57_wzc_F | 4425/51 wzc | Δwzabc | GGTCGACGGATCCCCGGAATGAATCGGATGATATCGATTTAGGTAAAATTGT (SEQ ID NO: 43) |
| K57_wzc_R | 4425/51 wzc | Δwzabc | GCTAATAGCTTTCAAACGACTTATATAGGTTA (SEQ ID NO: 44) |

| Name | Target | Purpose | Primer sequences (5'->3') |
|---|---|---|---|
| P1 | pKD13-kan | Kan-cassette C | GTGTAGGCTGGAGCTGCTT (SEQ ID NO: 45) |
| P4 | pKD13-kan | Kan-cassette | ATTCCGGGGATCCGTCGACC (SEQ ID NO: 46) |

Deletion of guaBA from *K. pneumoniae* B5055—

DNA was first purified from B5055 with the Qiagen DNEasy Blood and Tissue kit according to the manufacturer's protocol. DNA upstream of guaA was amplified using the following primers that produce a 688 bp DNA fragment (KP guamut F: 5'-GGTCGACGGATCCCCGGAATGGAG-TAATCCCCGGCGTTAG-3' (SEQ ID NO:31); KP guaBA_688_R: 5'-TGATTGGTCTGACTGGACGC-3' (SEQ ID NO:28)). DNA downstream of guaB was amplified using primers that produce a 676bp DNA fragment (KP guaBA_676_F: 5'-GGGTAGATGATCACCGGCAG-3' (SEQ ID NO:27); KP guamut R: 5'-GAAGCAGCTCCA-GCCTACACGGGCAATATCTCGACCAGGG-3' (SEQ ID NO:32)). PCR amplification of the guaA/guaB flanking regions was conducted using Vent polymerase. PCR products were electrophoresed on a 1% agarose gel and extracted and purified with a Qiagen Gel extraction kit according to the manufacturer's protocol. The PCR products were combined in an overlapping PCR reaction using a Kan cassette amplified from pKD13 as described by Datsenko and Wanner. The PCR product of ~2.4 kb was gel extracted and amplified with guaBA_676_F/guaBA 688 R before transformation. Electrocompetent B5055 cells were transformed by electroporation with pKD46. Electrocompetent cells of *K. pneumoniae* B5055 expressing lambda red recombinase were prepared and electroporated with the 2.4 kb PCR product. Kanamycin resistant colonies were selected and screened for integration of the Kanamycin resistance cassette. The Kanamycin resistance cassette was subsequently deleted using pCP20 that removes the cassette via the FRT sites present in the sequence. To remove pCP20, cells were grown at 42° C. and tested after each passage for loss of Carbenicillin or Chloramphenicol resistance.

Deletion of Capsule Genes from *K. pneumoniae* B5055—

The genes encoding capsule synthesis in *K. pneumoniae* B5055 were also deleted using lambda red recombination. DNA downstream of wza was amplified using the following primers that produce a 600 bp DNA fragment (wza_F: 5'-GAGCCGACTCTAGGGTGGC-3' (SEQ ID NO:37); wza_R: 5'-GAAGCAGCTCCAGCCTACA CTAATGTCA-CATCATCAGTAAAT CAAAATTTG-3' (SEQ ID NO:38)). Primers for the other flank amplify a region inside wzc itself since it is specific for the capsule type while the surrounding regions are highly variable between different capsule types. The primers (K2_wzc_F: 5'-GGTCGA CGGATCCCCG-GAATGTAATAGATATGTTATAGAGTTTG-GAGGGGAG-3' (SEQ ID NO:39); K2_wzc_R: 5'-TATT-TAATTTCCCTCTTTCATCCTGTAATGTT-3' (SEQ ID NO:40)) produced a 600 bp fragment. The same procedure as used for the guaBA mutagenesis were used.

Figure 12:
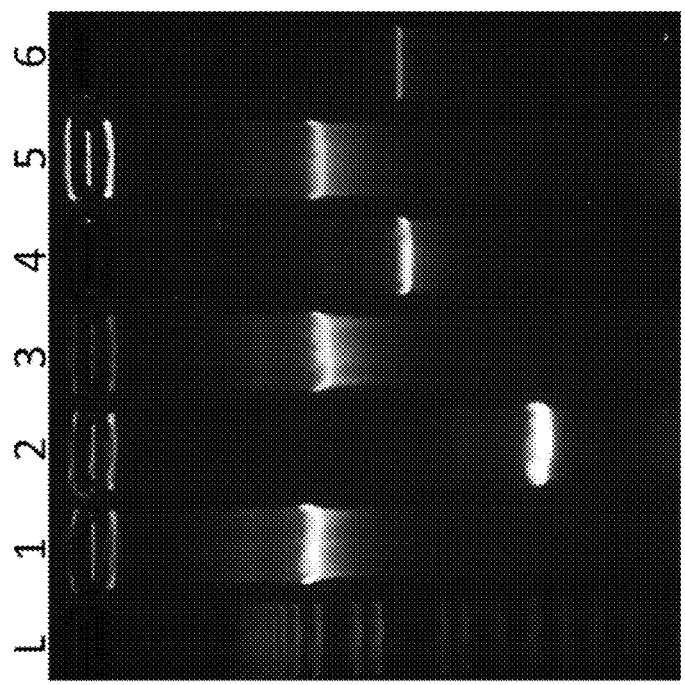
FIG. 12. Confirmation of deletion of guaBA by PCR. Lane 1, Kp B5055 (O1:K2) wild type; 2, Kp B5055 ΔguaBA; 3, Kp 390 (O3:K11) wild type; 4, Kp 390 ΔguaBA; 5, Kp 7380 (O2:K−) wild type; 6, Kp 7380

Mutagenesis was verified by PCR and sequencing upstream and downstream of the deletion is shown in FIG. 12.

The capsule deletion was assessed by India Ink staining and microscopic observation of the parental and mutant strain. The *K. pneumoniae* B5055 ΔguaBA Δwzabc strain showed no evidence of capsule whereas the wild-type strain was capsule positive.

We have confirmed the guanine auxotrophy phenotype by growing the recombinant strains on minimal media containing or lacking guanine (FIG. 13). We have shown that guanine must be supplied for growth of the KP ΔguaBA mutants.

Verification of Attenuation-KP O1:

K2 strains are highly virulent for mice but most other serotypes that are human pathogens have been found to be avirulent in mice. To confirm that the CVD 3001 reagent strain (B5055 ΔguaBA Δwzabc) is attenuated, we tested this mutant in mice and showed that the intraperitoneal 50% lethal dose is higher than the wild-type parental strain (Table 7). $LD_{50}$ analysis was conducted using 5 CD-1 mice per group injected IP with 10-fold dilutions of wild-type KP and the candidate engineered attenuated derivative.

TABLE 6

Verification of attenuation of KP reagent strain in vivo.

| Strain | 50% lethal dose |
|---|---|
| Wild-type B5055 | $5.34 \times 10^3$ CFU |
| B5055 ΔguaBA Δwzabc (CVD 3001) | $>10^8$ CFU |

Construction of Recombinant *S. Enteritidis* that Express Type A and B Flagella from *P. aeruginosa*—

We cloned flaA from *P. aeruginosa* PAK which encodes Type A flagella (40 kDa) into pSEC10, a low copy number highly stable plasmid. We also cloned flaB from *P. aeruginosa* PAO1 which encodes Type B flagella (52 kDa) into pSEC10. The recombinant plasmids were transformed separately into CVD 1947 (*S. Enteritidis* R11 ΔguaBA ΔclpP ΔfliD ΔfliC) to create reagent strains capable of expressing large amounts of Type A or B flagellin. Mutagenesis was verified by PCR and sequencing upstream and downstream of the deletion. Secretion of Type A or B flagella was verified by SDS-PAGE.

The fliC gene was amplified from *P. aeruginosa* PAK using primers PAK_fliC_F and PAK_fliC_R and cloned into pSEC10 so that it is expressed using the PompC promoter. Likewise, the fliC gene was amplified from *P. aeruginosa* PAO1 using primers PAO1_fliC_F and PAO1_fliC_R and cloned into pSEC10 so that it is expressed using the PompC promoter. Primers used for cloning are shown in Table 4.

TABLE 7

Primers used for cloning of *P. aeruginosa* fliC genes in pSEC10.

| Name | Strain | Restriction site | Sequence (5'-3') |
|---|---|---|---|
| PAK_fliC_F | PAK | BamHI | TATCTAGGATCCATGGCCTTGACCGTCAACAC (SEQ ID NO: 47) |
| PAK_fliC_R | PAK | NheI | CTAAGTGCTAGCAAGCTTAGCGCAGCAGGCT (SEQ ID NO: 48) |
| PAO1_fliC_F | PAO1 | BamHI | ACTTGCGGATCCATGGCCCTTACAGTCAACACG (SEQ ID NO: 49) |

TABLE 7-continued

Primers used for cloning of P. aeruginosa fliC genes in pSEC10.

| Name | Strain | Restriction site | Sequence (5'-3') |
|---|---|---|---|
| PAO1_fliC_R | PAO1 | NheI | ATTAGCGCTAGCCGTGAG TGACCGTTCCCG (SEQ ID NO: 50) |

Construction of the Reagent Strain *S. Enteritidis* CVD1947—

We previously used *Salmonella Enteritidis* CVD 1943 (R11 ΔguaBA ΔclpP ΔfliD) to express large amounts of flagellin into the supernatant. We genetically engineered this strain so that it no longer expresses native fliC. The objective is to use this strain to express exogenous fliC from a plasmid and which is secreted into the supernatant. We used lambda red recombination to delete the fliC gene. To ensure transcription of downstream genes after deletion of fliC in CVD 1943, the kanamycin cassette from pKD4 was used since it allows conservation of multiple promoter sites in the scar region after removing the kanamycin cassette from the genome. The primers shown in Table 5 were used to create a construct by overlapping PCR containing the Kanamycin cassette flanked by DNA upstream and downstream of fliC. Primers R11_fliC_up_F3 and R11_all_up_R3 amplify a 259 bp fragment upstream of fliC. R11_fliC_dwn_F3 and R11_fliC_dwn_R3 amplify a 301 bp fragment downstream of fliC. The fliC gene was subsequently deleted using lambda red recombination.

TABLE 8

Primers used for mutagenesis of *Salmonella Enteritidis* CVD1947.

| Name | Target | Sequence (5'-3') |
|---|---|---|
| P1 | pKD4 | GTGTAGGCTGGAGCTGCTTC (SEQ ID NO: 51) |
| P2 | pKD4 | CATATGAATATCCTCCTTA (SEQ ID NO: 52) |
| R11_fliC_up_F3 | R11 | CCATGCCATCTTCCTTTCG (SEQ ID NO: 53) |
| R11_all_up_R3 | R11 (P1 cpt) | GAAGCAGCTCCAGCCTACACG ATCTTTTCCTTATCAATTACAA CTTG (SEQ ID NO: 54) |
| R11_fliC_dwn_F3 | R11 (P2 cpt) | TAAGGAGGATATTCATATGATC CGGCGATTGATTCAC (SEQ ID NO: 55) |
| R11_fliC_dwn_R3 | R11 | TGGTAATTTAATCTCCCCCCA (SEQ ID NO: 56) |

We verified the deletion of fliC in CVD 1947 by sequencing the deletion. The entire fliC gene was deleted.

The pSEC10-flaA and pSEC10-flaB plasmids were transformed into *S. Enteritidis* CVD 1947. We confirmed that CVD1947 (pSEC10-flaA) and CVD 1947 (pSEC10-flaB) can express FlaA and FlaB in the supernatant where they demonstrated the approximate predicted molecular weight of ~45 kDa and ~50 kDa respectively by SDS-PAGE and coomassie analysis (FIG. 14). Secreted recombinant FlaA expressed in CVD 1947 was also recognized by western blot with polyclonal sera from mice immunized with purified native FlaA obtained from *P. aeruginosa* strain PAK (FIG. 15).

Purification and Characterization of *Klebsiella pneumoniae* O1 O-Polysaccharide (OPS)—

Recombinant *K. pneumoniae* strain CVD3001 was grown to stationary phase by overnight growth in shaking culture at 37° C. in fully chemically defined media supplemented with guanine. OPS was extracted from the bulk growth culture by two different methods. In the first method, OPS was released from the core PS KDO by reduction of the culture pH to ~3.7 with acetic acid and incubation at 100° C. for 4 hours. In the second method, the culture was brought to pH ~3.7 with acetic acid and incubated with 200 mg/L sodium nitrite for 6 hours at 4° C. to release the OPS by nitrous acid deamination. Following OPS release, cells and insoluble debris were removed by centrifugation and clarification through a 0.45 um filter. Extraction by either method yielded OPS molecules of similar size that could be distinguished from residual contaminants in the post-hydrolysis supernatant by high-performance liquid size-exclusion chromatography (HPLC-SEC) analysis with detection by refractive index (RI). The OPS was purified from residual soluble contaminants by sequential steps involving 30 kDa molecular weight cutoff (MWCO) tangential flow filtration (TFF), anion-exchange chromatography, and ammonium sulfate precipitation. The purified material was concentrated and diafiltered into water by 10 kDa MWCO TFF. Analysis of the final-purified and in-process material by HPLC-SEC/RI demonstrated a single major molecular weight OPS species that was retained throughout the purification process.

Figure 1:
FIG. 1. Sequence of selected KP OPS serotypes and core polysaccharide. The OPS repeat structures for the 4 vaccine serotypes proposed are shown; CP primer is the terminal attachment point to the common Core PS (adapted from Vinogradov E et al., *J Biol Chem.*; 277(28):25070-25081).
Figure 2:
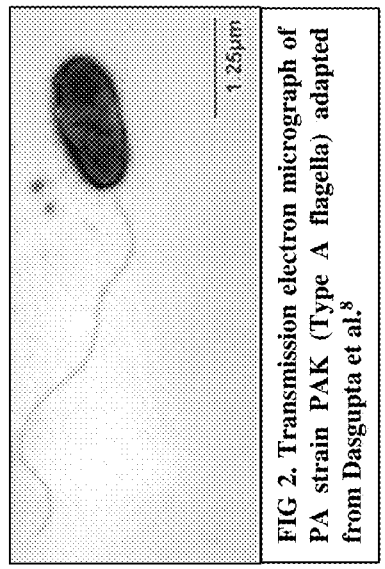
FIG. 2. Transmission electron micrograph of PA strain PAK (Type A flagella) adapted from Dasgupta et al.
Figure 3:
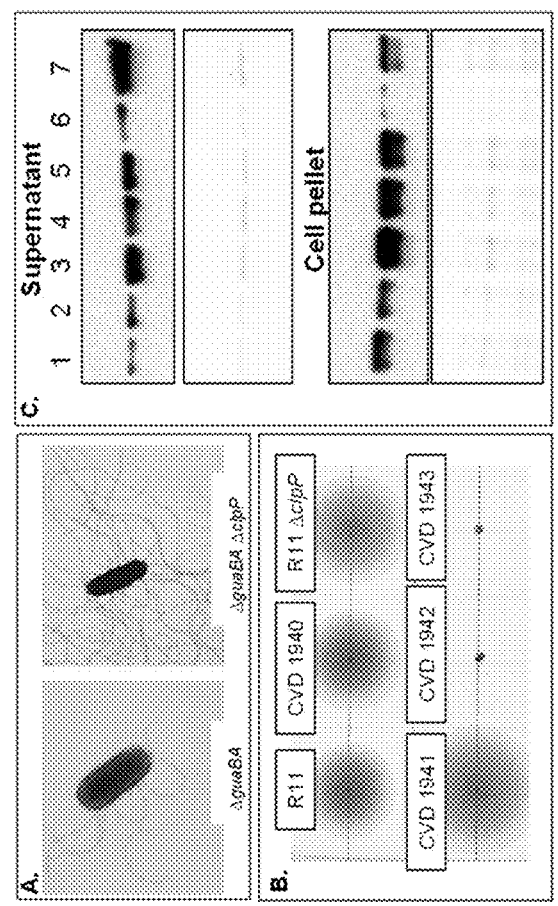
FIG. 3. *Salmonella* with deletions in clpP or clpX are hyperflagellated. A) Electron micrograph of *S. Paratyphi* A; B) Motility of recombinant *S. Enteritidis* strains and C) Coomassie-stained SDS-PAGE and western blot (anti-FliC) of recombinant *S. Enteritidis* strains. Lanes 1, *S. Enteritidis* R11; 2, CVD 1940 (R11 ΔguaBA); 3, R11 ΔclpP; 4, CVD 1941 (R11 ΔguaBA ΔclpP); 5, R11 ΔguaBA ΔclpX; 6, CVD 1942 (R11 ΔguaBA ΔfliD); 7, CVD 1943 (R11 ΔguaBA ΔclpP ΔfliD).
Figure 4A:
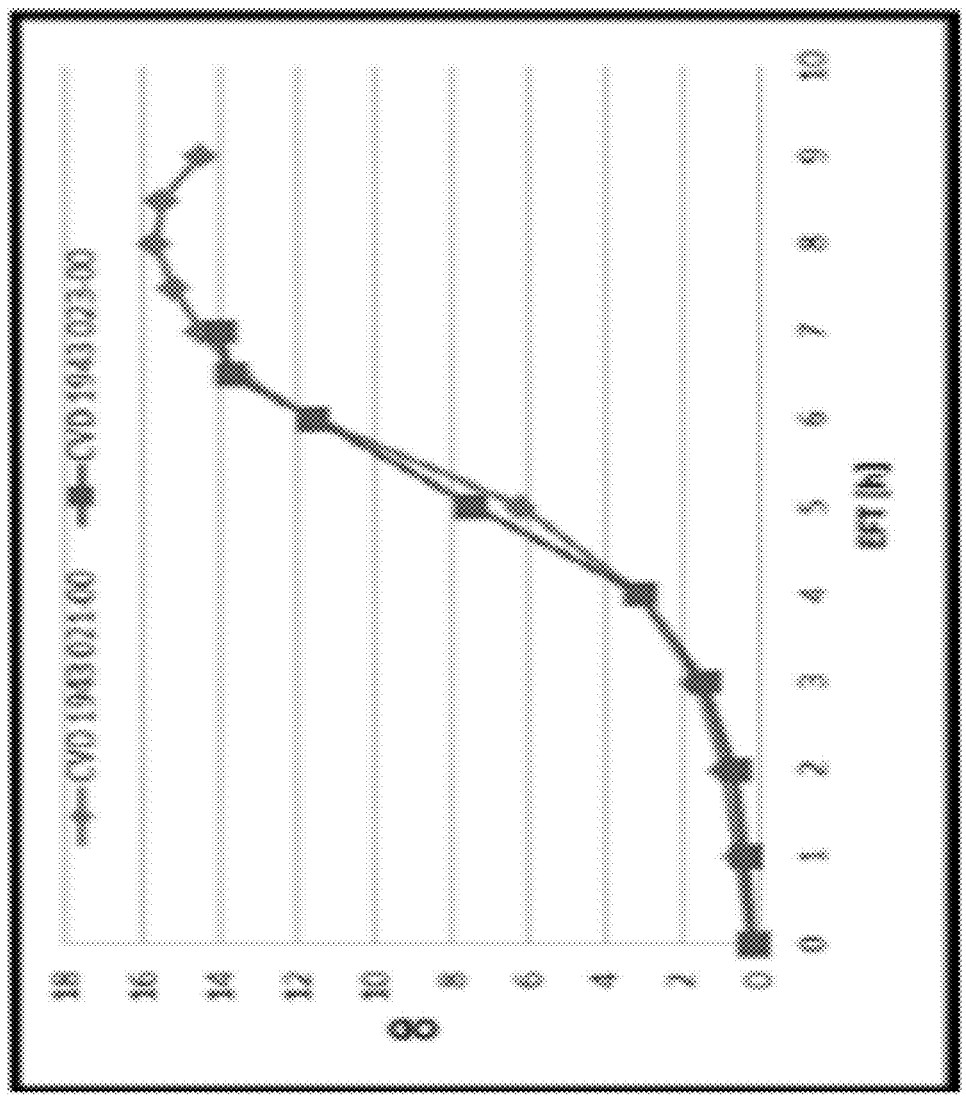
FIG. 4. Purification of FliC and COPS from attenuated CVD 1943 *S. Enteritidis*. A. $OD_{600}$ versus time for two independent 20 L scale fermentor runs of CVD 1943; B. Protein accumulation in fermentation supernatant; C. HPLC-SEC (SDS-PAGE inset) of final CVD 1943 FliC purified from fermentation supernatant; D. SDS-PAGE with polysaccharide stain on LPS from fermentation culture (lane 1=LPS standards, 2=CVD 1943 cells); E. HPLC-SEC of purified CVD 1943 COPS polysaccharide (Red=Refractive Index, Black=Abs252 nm); F. HPAEC-PAD monosaccharide composition analysis for CVD 1943 COPS (indicated peaks based on monosaccharide standards).
Figure 4B:
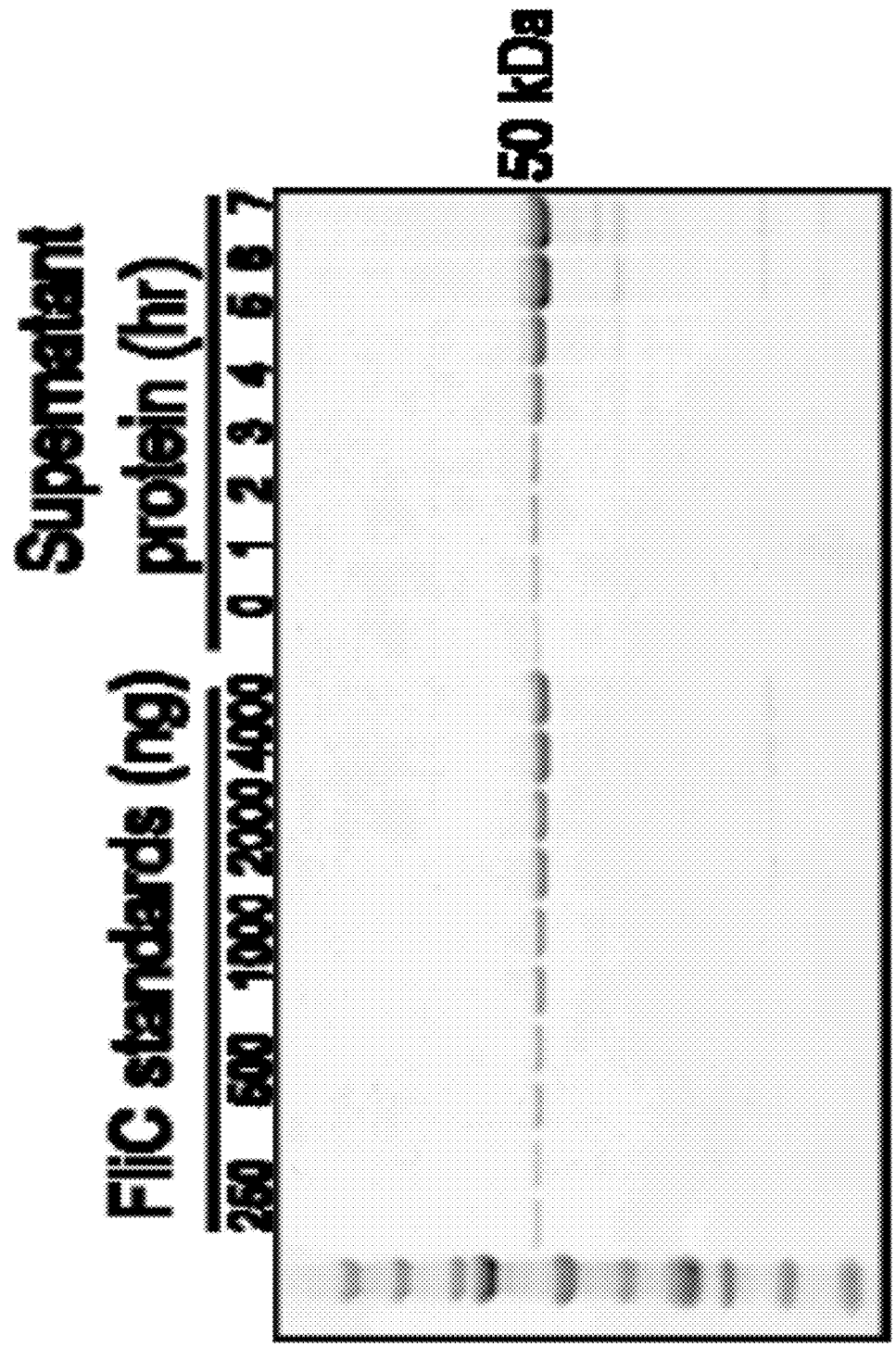
Figure 4C:
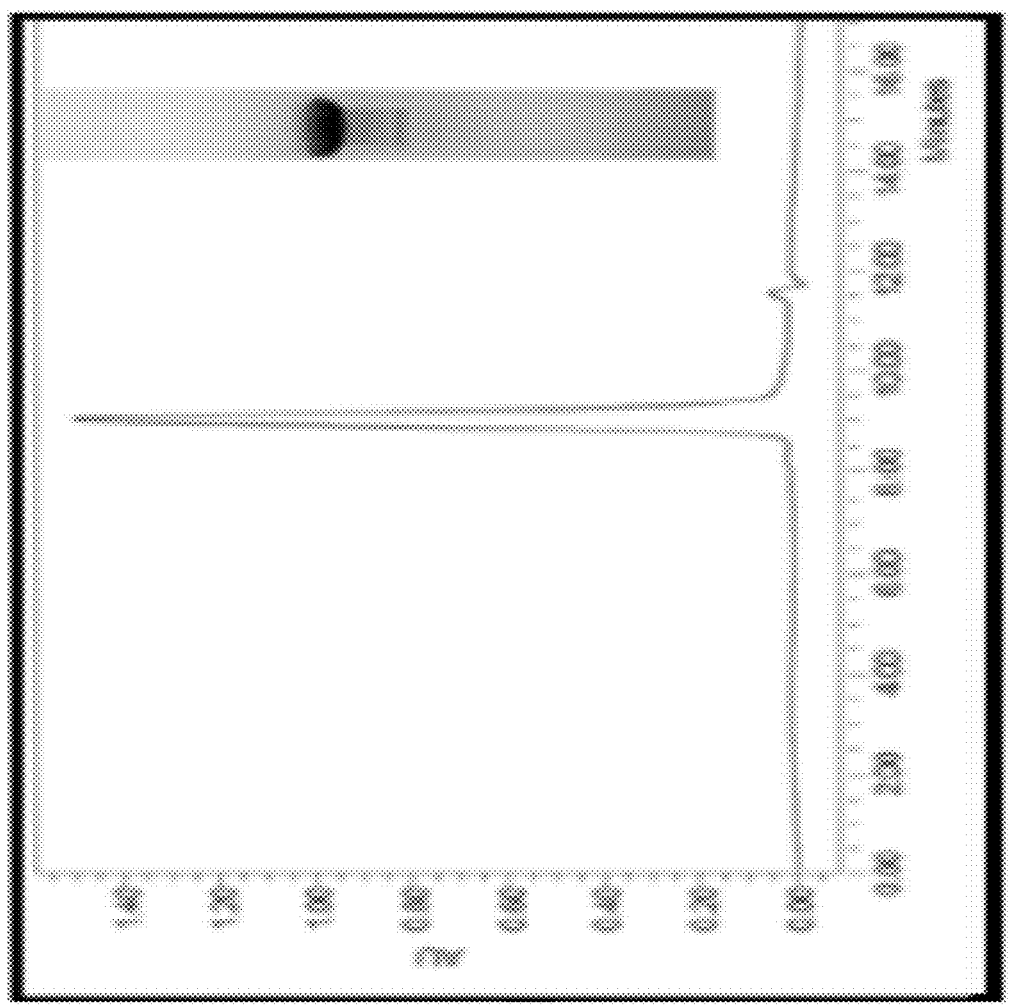
Figure 4D:
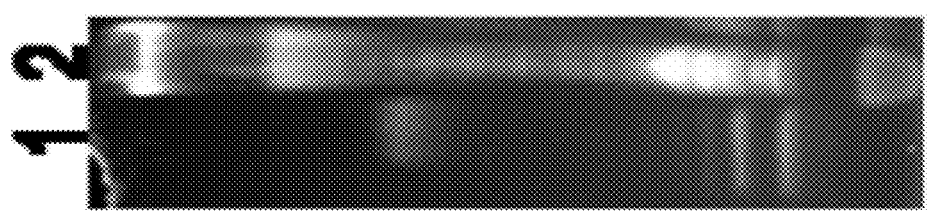
Figure 4E:
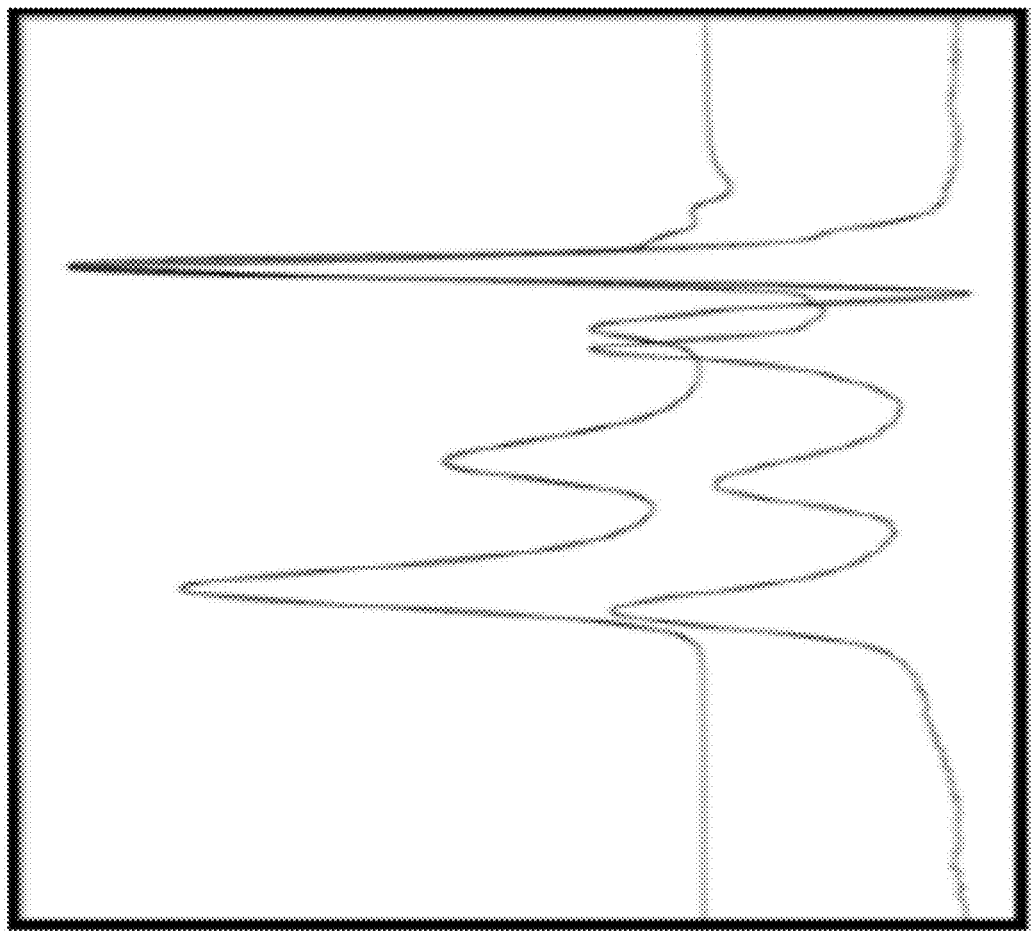
Figure 4F:
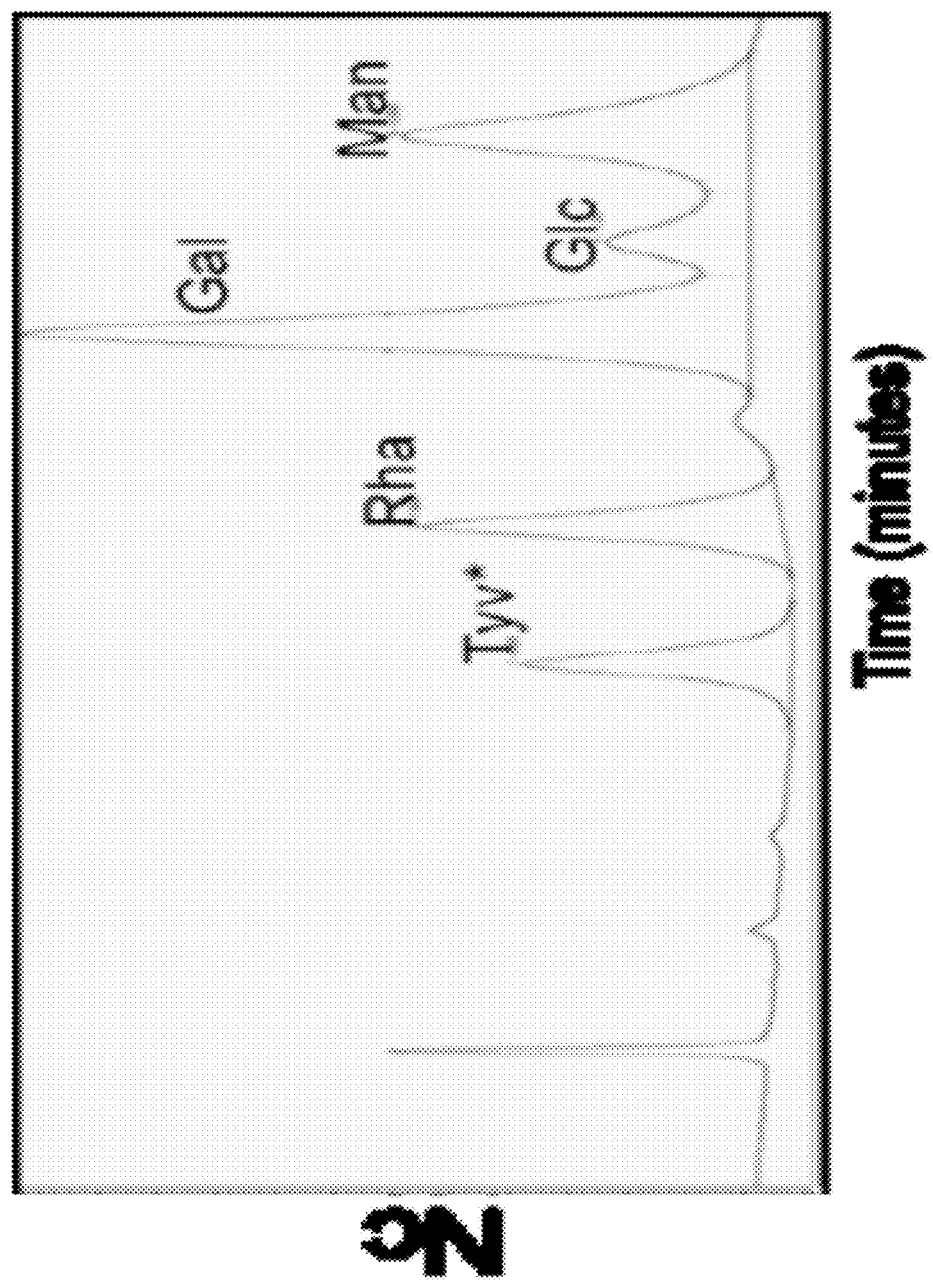
Figure 5:
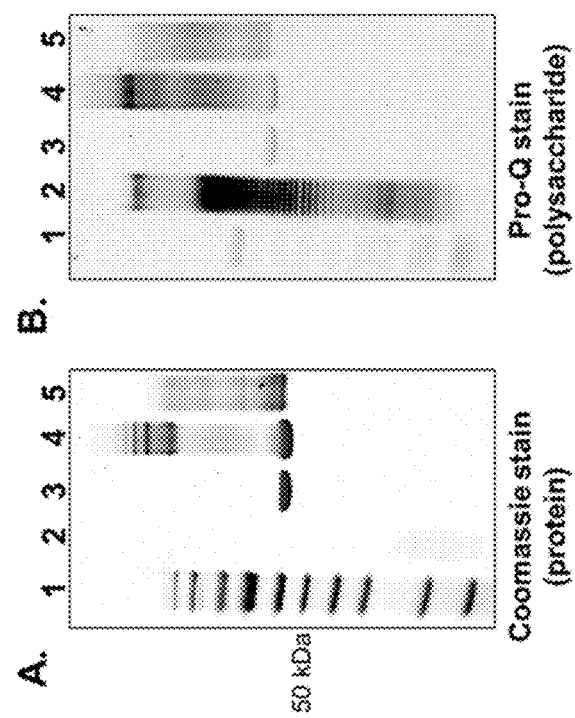
FIG. 5. Conjugation of *S. Enteritidis* COPS conjugates. (A and B) Four to 20% SDS-PAGE showing Coomassie blue (A) or Pro-Q (B) staining of COPS conjugates. Lanes 1, protein standards; 2, 10 μg *S. Enteritidis* LPS; 3, 10 μg *S. Enteritidis* flagella; 4, 10 μg COPS:FliC CDAP linked conjugate; 5, 10 μg COPS:FliC oxime linked conjugate.
Figure 6:
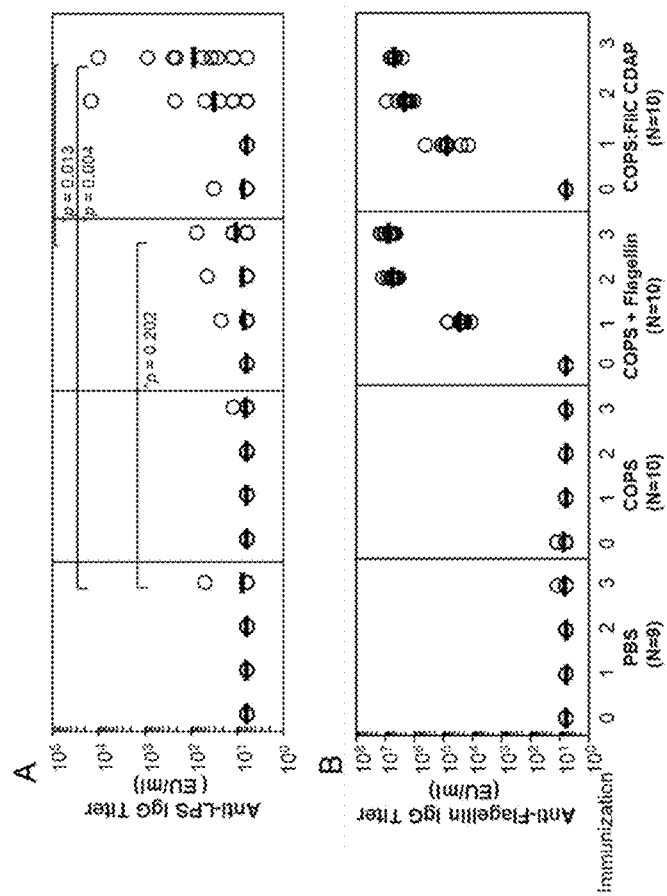
FIG. 6. Humoral immune responses in BALB/c mice following immunization with PBS sham, *S. Enteritidis* COPS, COPS admixed with flagellin monomers, or O:H 1:1 lot 1 conjugate. Serum anti-LPS IgG (A) and anti-flagellin IgG (B) titers in individual mice (○) and geometric means (■) before immunization (time 0) and at 21 days following the 1st (1), 2nd (2), or 3rd (3) immunization. "*" compared to PBS by Mann-Whitney Rank-Sum test.
Figure 7:
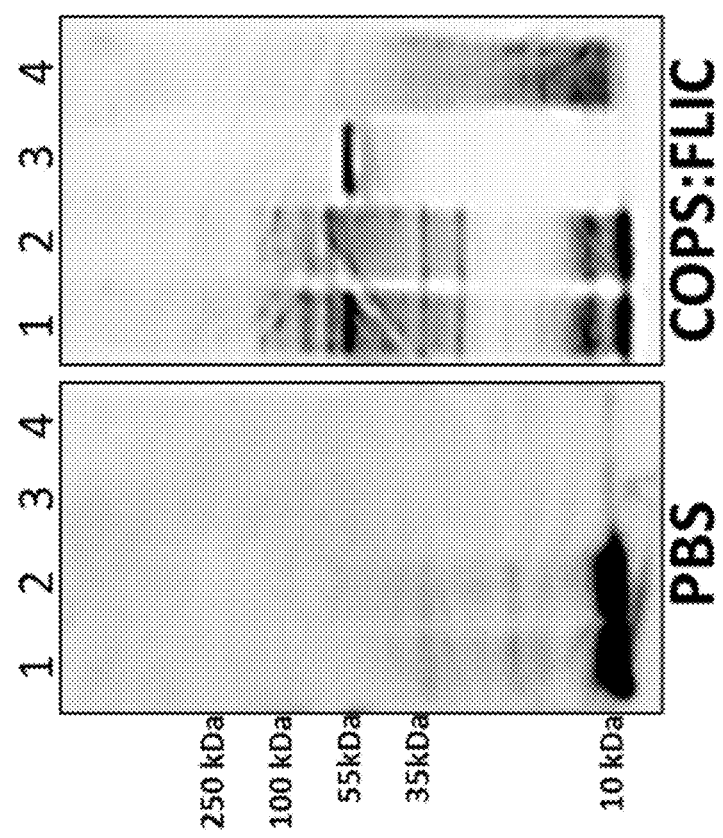
FIG. 7. Western blot with COPS:FliC sera: Pooled sera from mice immunized with PBS or *S. Enteritidis* COPS:FliC was used to probe (1) *S. Enteritidis* R11 lysate, (2) R11 flagellin mutant (ΔFliC) lysate, (3) purified *S. Enteritidis* FliC, and (4) purified *S. Enteritidis* LPS.
Figure 8:
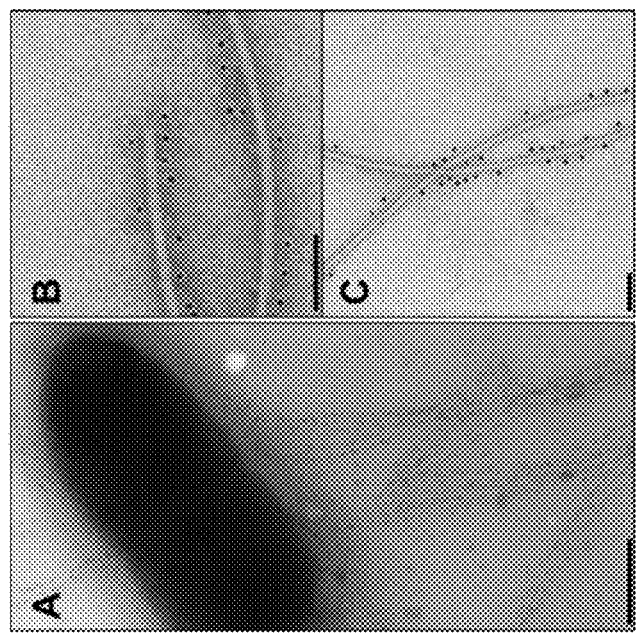
FIG. 8. Immunogold labeling of *S. Enteritidis* strain S15. Flagella labeled with sera from mice immunized with *S. Enteritidis* flagellin. Bar, 500 nm.

The identity of the final purified O1 OPS was accomplished by depolymerization with 2M Trifluoroacetic acid and analysis of the monosaccharide constituents by high-performance anion-exchange chromatography with pulsed amperometric detection (HPAEC-PAD). Monosaccharide composition analyses revealed that the OPS was comprised primarily of galactose with a minor N-acetyl-glucosamine peak detected. This is consistent with the published chemical structure of O1 OPS that is comprised entirely of galactose with a terminal N-acetyl-glucosamine residue present at the reducing end adjacent to the KDO, that is the expected site of hydrolysis by our extraction method (FIG. 1) (Vinogradov et al., *J Biol. Chem.* 2002; 277:25070-25081).

Expression and Purification of *Pseudomonas aeruginosa* Flagellin—

Figure 16:
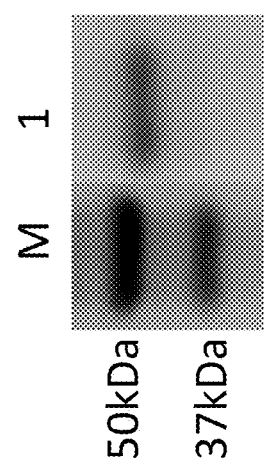

Expression of rFlaA for subsequent purification was accomplished by growing CVD 1947 containing pSEC10_rFlaA in fully defined chemical media supplemented with guanine and kanamycin at 37° C. under shaking conditions to mid-log phase. The culture supernatant containing the secreted rFlaA was clarified from cells by centrifugation and filtration with a 0.45 um filter. rFlaA was then purified from the clarified culture supernatant using sequential cation- and anion-exchange membrane chromatography steps as described (Simon R et al., *Protein Expr. Purif.* 2014; 102:1-7). SDS-PAGE and coomassie analysis of the final purified product confirmed a single ~45 kDa band (FIG. 16).

Conjugation of *Klebsiella pneumoniae* O1 OPS with Recombinant *Pseudomonas aeruginosa* FlaA—

Figure 17:
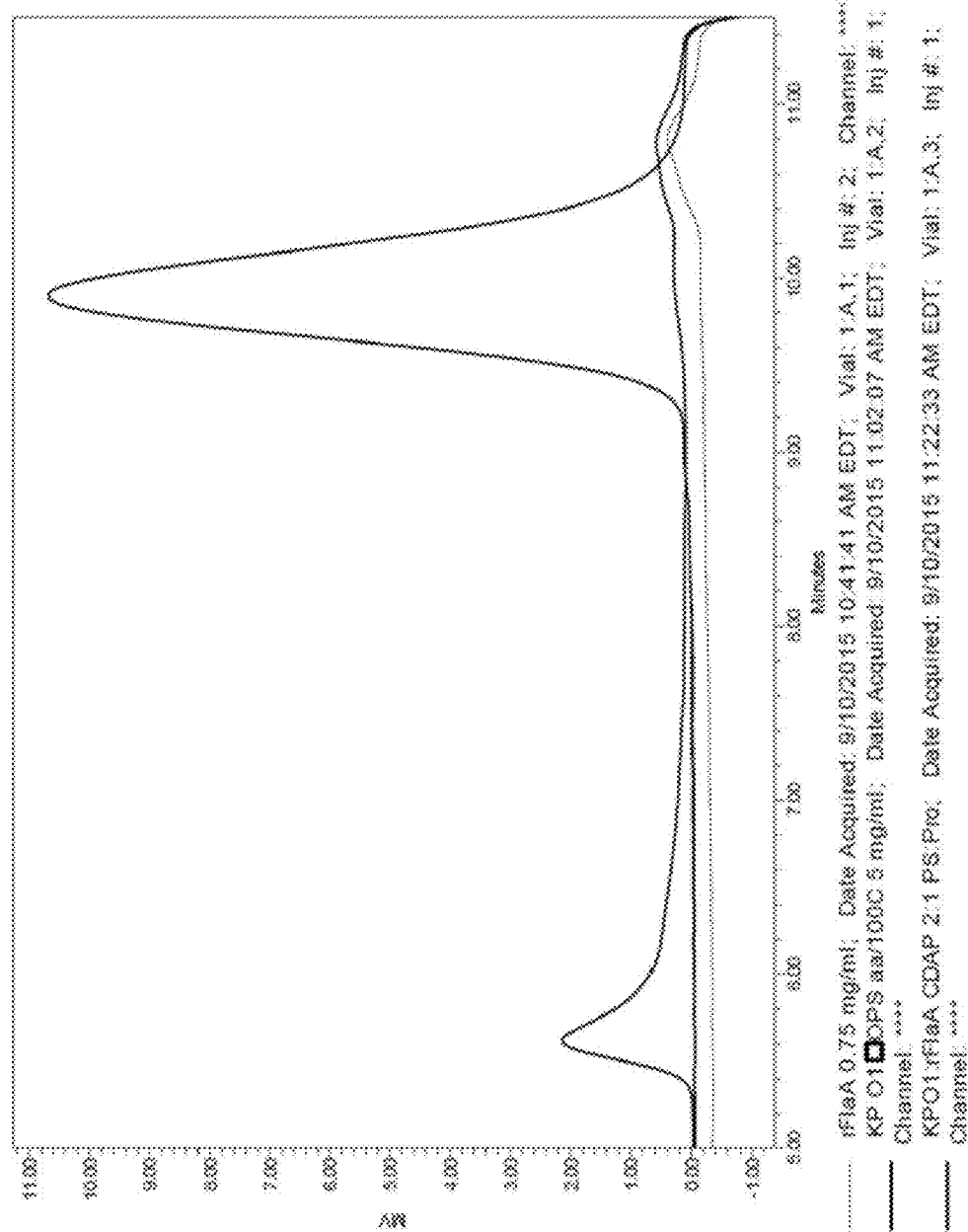
Figure 18:
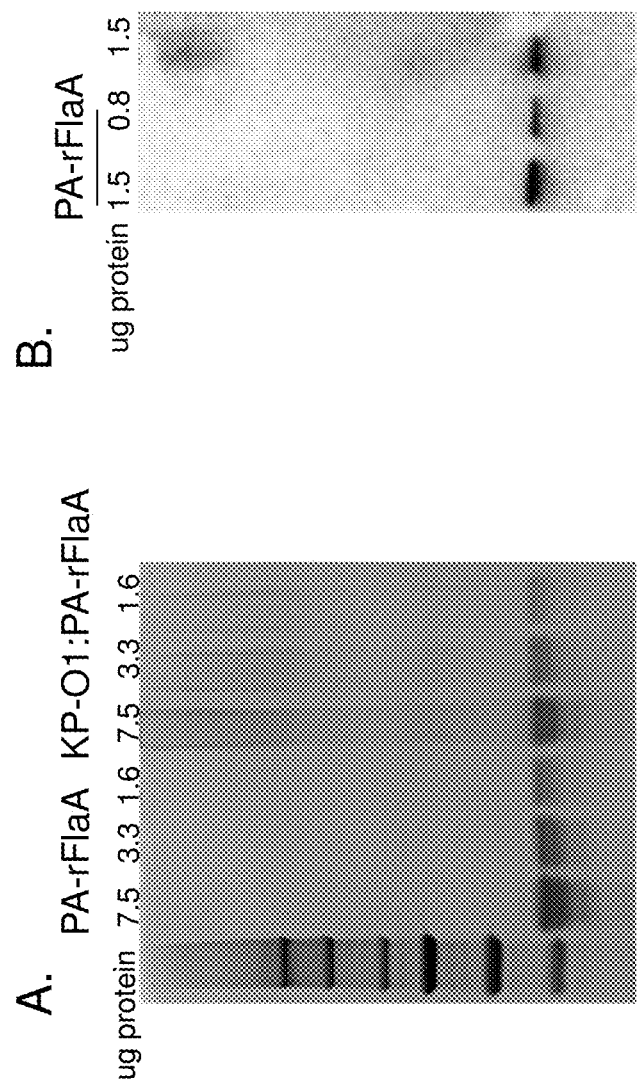

OPS was activated with CDAP at pH 9, added directly to purified recombinant FlaA, and incubated overnight at 4° C. Conjugation was assessed by HPLC-SEC (FIG. 17), where a shift in size was seen to higher molecular weight species after linkage. Unconjugated OPS and rFlaA produced distinct peaks at ~10 minutes and 10.8 minutes respectively, whereas the conjugated material produced a sharp peak at ~5.5 minutes that represents the column void volume (>650 kDa) with a large trailing tail of smaller conjugates persisting till ~9 minutes. This indicates a heterogenous conjugate population comprised by large and very large molecular weight species. Due to the very high molecular weight of the conjugate seen by HPLC-SEC, it is likely that much of the conjugated material is too large to enter an SDS-PAGE gel. Nevertheless, SDS-PAGE analysis with coomassie staining (FIG. 18A) confirmed the shift to a heterogeneous mix of higher molecular weight species seen by the smear above the level of remaining unconjugated protein. Western blot analysis performed on the purified flagellin and KP-O1:PA-rFlaA conjugate with polyclonal mouse anti-sera raised against native FlaA (FIG. 18B) confirmed identity of the conjugated material seen in the material that was of sufficient size to enter the gel matrix.

Figure 19:
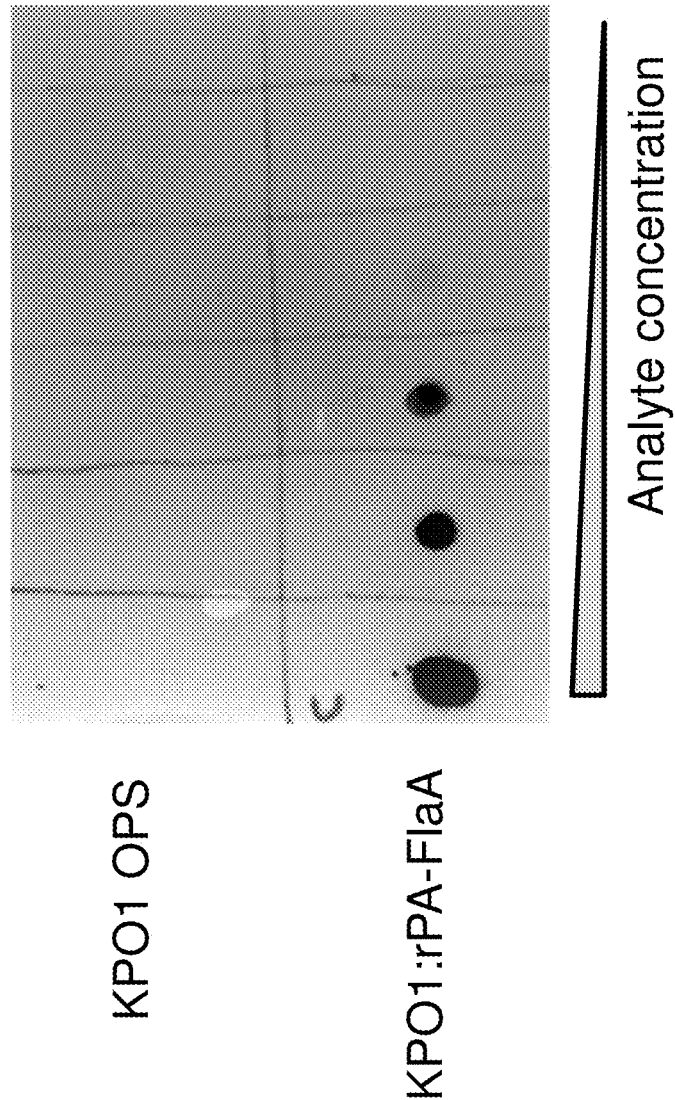

Dot blot analysis of the conjugate and unconjugated polysaccharide confirmed reactivity of the conjugate with sera from mice administered CVD 3001 (KP O1 reagent strain deleted for guaBA and capsule synthesis genes). A robust signal was seen for the conjugate, whereas the polysaccharide did not bind the membrane as no protein component was present that is required for binding, thus confirming that conjugated saccharide was reactive with the anti-O1 antibodies (FIG. 19).

Constructing and Assessing in Rodents KP:PA Conjugates with Different Combinations and Chemistries in Monovalent and Quadrivalent Formulations—

*Klebsiella pneumoniae* LPS and *Pseudomonas aeruginosa* flagellins have been demonstrated conclusively as protective against the cognate pathogens expressing these antigens; however, there are no reports of vaccination approaches to elicit protective immunity to both of these molecules in a single formulation. As LPS is unacceptably reactogenic, and isolated OPS molecules are generally non-immunogenic, a conjugate vaccine approach is warranted. Remarkably, our literature search revealed only two published reports of KP COPS conjugates (with TT or KP OMPs), and while protection was documented, ELISA antibody titers and boost responses were not assessed (Chhibber S, *Indian J Exp Biol.* 2005; 43(1):40-45; Chhibber S, *Vaccine.* 1995; 13(2):179-184).

Flagellins have been found as effective carrier proteins, however, the majority of licensed conjugate vaccines use established vaccine proteins as carriers (e.g., TT, diphtheria toxoid)(Knuf M, *Vaccine.* 2011; 29(31):4881-4890), that are already administered separately as vaccine antigens, and for which immunity from the carrier protein is not a basis for licensure (Knuf M, *Vaccine.* 2011; 29(31):4881-4890). The exception is the GlaxoSmithKline 10-valent pneumococcal conjugate vaccine Synflorix™ that uses *Haemophilus influenzae* protein D as a carrier protein to extend protection against non-typeable *H. influenzae* acute otitis media (Forsgren A et al., *Clin Infect Dis.* 2008; 46(5):726-731; Prymula R, Schuerman L, *Expert Rev Vaccines.* 2009; 8(11):1479-1500). Two major challenges are thus addressed by our development approach. First, we will confirm induction of functional immunity by both the polysaccharide hapten and protein carrier. Immunogenicity and functional efficacy for OPS and Fla induced antibodies will likely be influenced by physicochemical conjugate structure. The size, structure, and level of solvent accessible protein and polysaccharide residues have been documented to influence coupling site preference in glycoconjugates (Bardotti A et al., *Vaccine.* 2008; 26(18):2284-2296); this could affect functional immunogenicity if important protective epitopes are the preferential sites of linkage. A minimal level of vicinial polysaccharide epitopes is necessary to cross-link B-cell receptors (BCR). We have found that conjugation of equal weights of COPS and flagellin produces linkage ratios that are immunogenic (Simon R, *Infect Immun.* 2011; 79(10):4240-4249; Raphael Simon J Y W et al., *PLOS ONE.* 2013; 8(5): e64680). Lattice type conjugates provide larger surfaces for BCR cross-linking, however, CDAP activation also alters polysaccharide linkage point epitopes. End-linkage with oxime chemistry does not alter PS epitopes, but forms smaller conjugates. By screening COPS conjugates made with different chemistries and PA Fla types, we expect to identify optimal monovalent conjugate formulations. Secondly, possible interference between individual components is a recognized pitfall of multivalent vaccine formulations. Thus, it will be confirmed that the immunogenicity and efficacy of individual component OPS and flagellin antigens are preserved when combined into a quadrivalent formulation. By identifying in animals optimally immunogenic and protective monovalent conjugate architectures and confirming immunogenicity when co-formulated, effective quadrivalent formulations will be produced.

Figure 20:
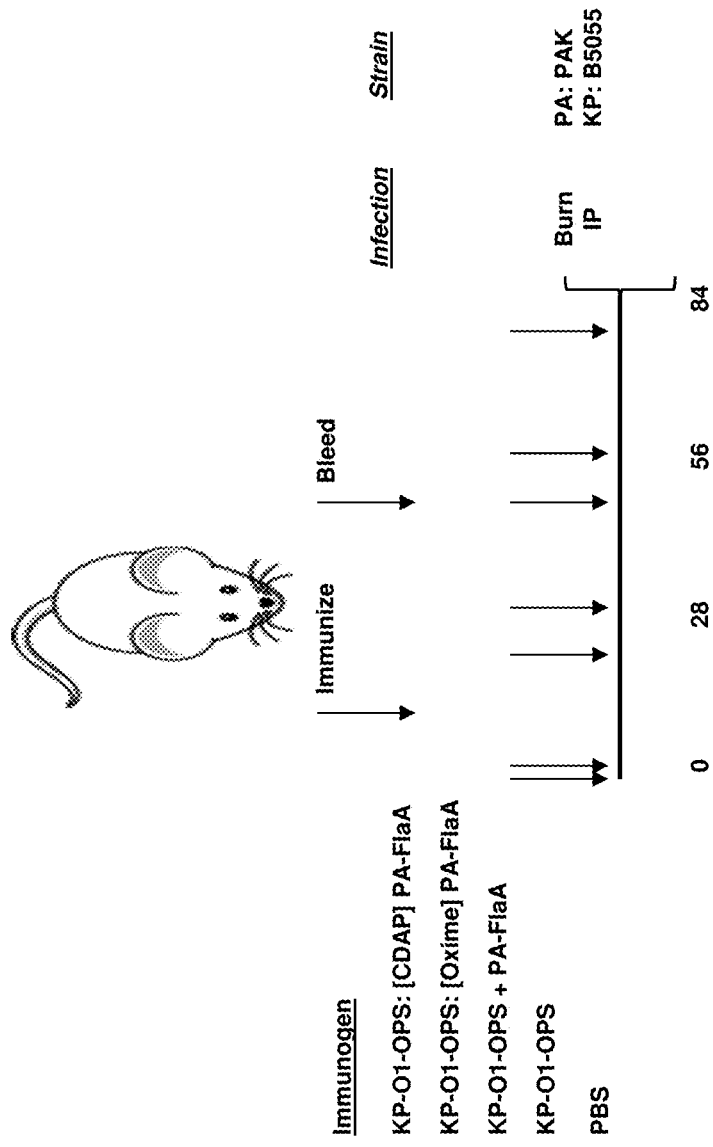

Prior to undertaking a quadrivalent conjugate screen, proof-of-concept will first be established for a single candidate monovalent antigen KP-OPS:PA-Fla conjugate type synthesized with material purified from shake flask cultures. Accordingly, we will construct candidate conjugates of KP O1 OPS with type A PA flagellin, as both of these types have been reported extensively as protective vaccine antigens using well characterized challenge strains and infection models. We will generate a sun-type KP-O1-OPS:PA-FlaA conjugate using oxime chemistry as well as a lattice type conjugate using CDAP, and immunize mice (n=30/group) 3 times at 28 day intervals with PBS, KP-O1-OPS:PA-FlaA conjugates, or O1 OPS alone or admixed with FlaA. We will assess the kinetics and induction of anti-LPS and anti-Fla antibody responses by measuring the level of vaccine induced IgG antibodies in sera before immunization and 21 days after each vaccine dose by ELISA with purified antigens, and by measuring functional activity using motility inhibition and OPA assays. We will determine whether KP-O1-OPS:PA-FlaA conjugates are protective against infection, by challenging IP with KP (n=15/group) or in burn wound infections with PA (n=15/group), as protection mediated by these KP and PA antigens is best established with these challenge routes. For challenge studies, we will use PA PAK that is a type A flagellin-expressing isolate or KP B5055 that is an encapsulated O1:K2 isolate, as both have been used extensively as challenge strains for vaccine studies in mice (FIG. 20).

Figure 21:
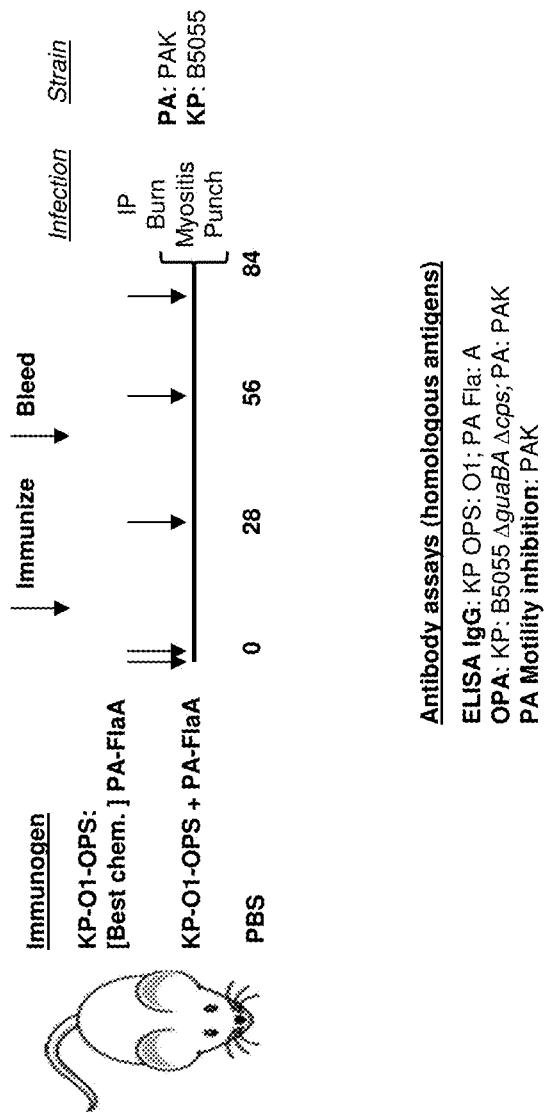

The conjugate type demonstrating the best immunogenicity and protection in will be assessed for protection against *Klebsiella pneumoniae* (KP) B5055 or *Pseudomonas aeruginosa* (PA) PAK administered by several routes of infection (burn, myositis, punch wound, or IP septicemia). Mice (n=120/group) will be immunized 3 times at 28 day intervals with PBS or KP-O1-OPS and PA FlaA conjugated or admixed. Preimmune sera and sera obtained 21 days after the final vaccination will be assessed for functional and binding antibodies with homologous antigens and strains. Mice (n=15/group) will be infected (wound and IP) with PA or KP (FIG. 21).

We will generate 16 different candidate conjugates by linking the individual KP OPS serotypes using CDAP or oxime chemistry to FlaA or FlaB, using material obtained from fermentation cultures. The two monovalent KP-O1-OPS:PA-FlaA CDAP and oxime conjugate types created above will be included for confirmation of previous results.

Figure 22:
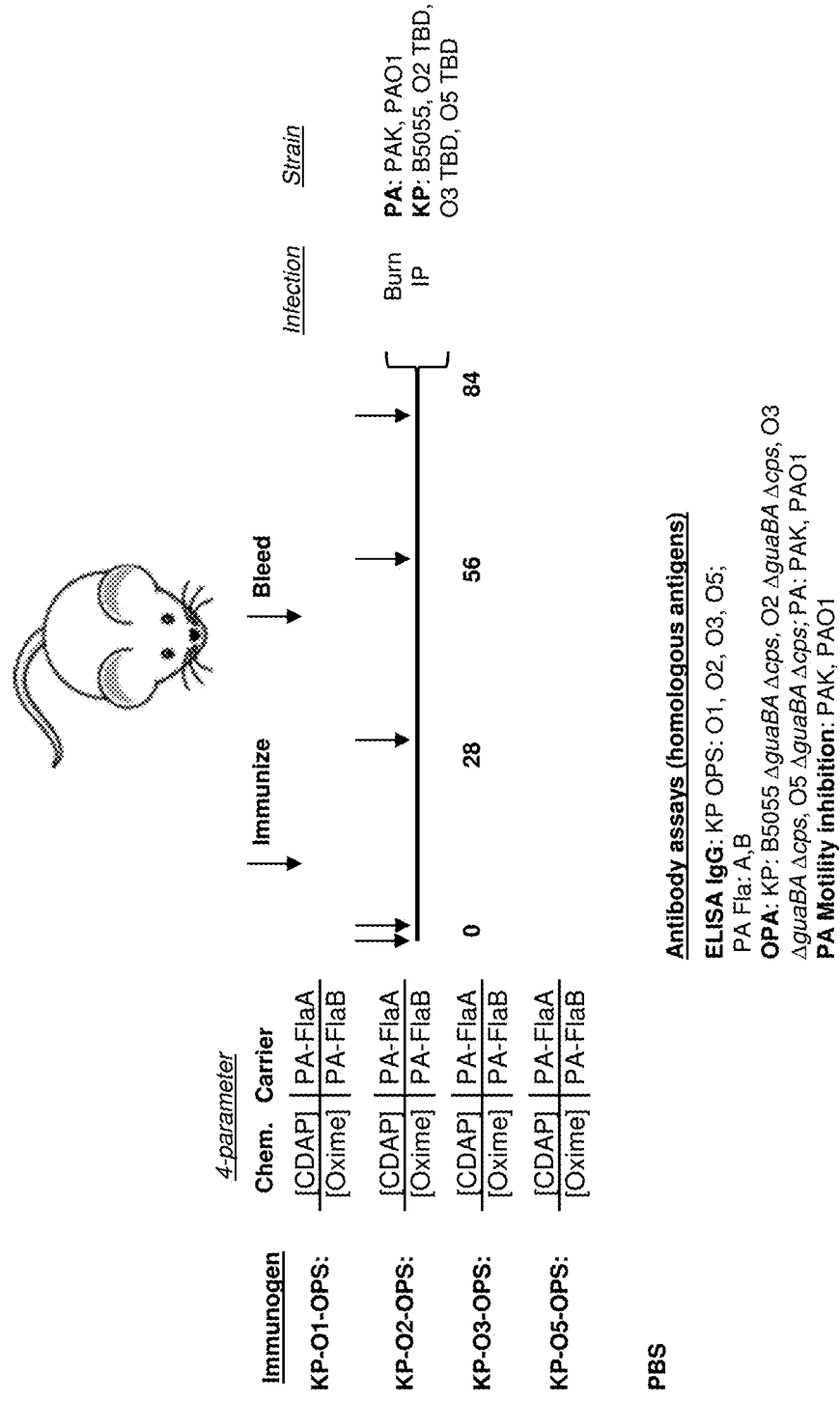

This conjugate panel will be tested individually in mice by immunizing with 3 doses spaced 28 days apart (n=30/group). Pre-immune sera and sera taken 21 days after the final dose will be assessed for homologous anti-LPS and anti-flagellin IgG levels by ELISA and functional antibodies by OPA or motility inhibition assays. We will screen for functional efficacy of vaccine-elicited antibodies in vivo by measuring protection against IP infection with the homologous KP O type expressing strain (O1: B5055; O2, O3 and O5: recombinant mouse virulent strains that we will generate; n=15/group), and burn wounds with the homologous flagellin expressing PA strain (n=15/group)(FIG. 22).

A single monovalent conjugate from each OPS type will subsequently be selected for inclusion in a quadrivalent formulation based on the following ranked criteria: 1) anti-LPS IgG levels and KP OPA antibody titers, 2) anti-flagellin IgG and functional anti-PA antibody titers, 3) protective efficacy, 4) regulatory and manufacturing considerations (yield, ease of synthesis, epitope preservation, and regulatory precedent). We place anti-OPS responses as more critical than anti-flagellin responses in our go/no-go decision tree, as moderate anti-flagellin immune responses could be compensated for in a final formulation by the inclusion of multiple conjugates that utilize the same flagellin protein carrier. The final quadrivalent conjugate formulation will include minimally at least one conjugate made with each flagellin type, and would be anticipated to impart high IgG antibody levels to both flagellin types. We recognize as well that mouse protection studies may not always fully recapitulate the true pathogenicity of a given bacterial strain in humans, nor fully approximate the mechanisms of protective immunity. This is particularly true for KP, as numerous examples exist of human clinical isolates that demonstrate poor pathogenicity in mice (Struve C, Krogfelt K A, *Environ Microbiol.* 2004; 6(6):584-590; Simoons-Smit A M, *J Med Microbiol.* 1984; 17(1):67-77; Yu V L, *Emerg Infect Dis.* 2007; 13(7):986-993). Hence, while protection is one important measure of down-selection and is expected to approximate vaccine performance in humans, we place greater credence on the capacity to induce robust seroconversion levels and high titers in our chosen functional antibody assays, as these are the anticipated correlates and mechanisms of protection for humans.

Figure 23:
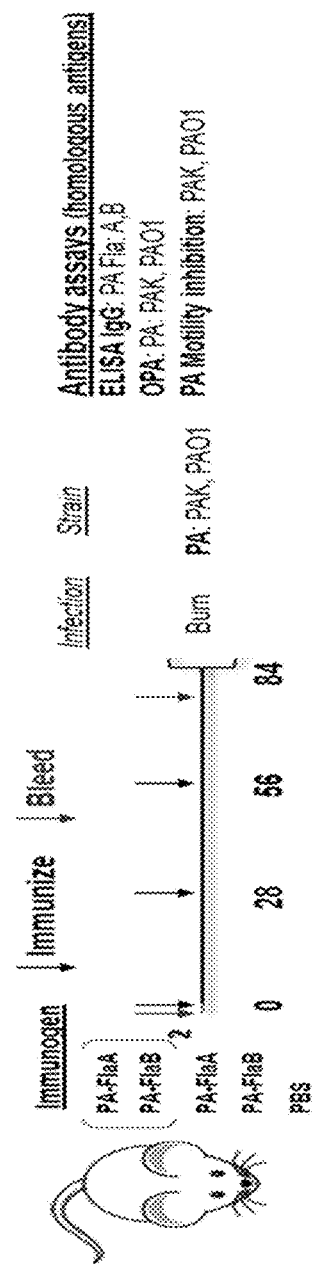

To confirm that the specific immune responses to FlaA and FlaB are maintained when co-formulated, mice will be immunized 3 times at 28 day intervals with monovalent (n=15/group) and bivalent (n=30/group) flagellin preparations. Levels of IgG and functional titers for the homologous Fla types will be determined in pre-immune sera and sera taken 21 days after the final dose. Protection will be assessed against burn infection with homologous Fla expressing PA strains (n=15/group)(FIG. 23).

Figure 24:
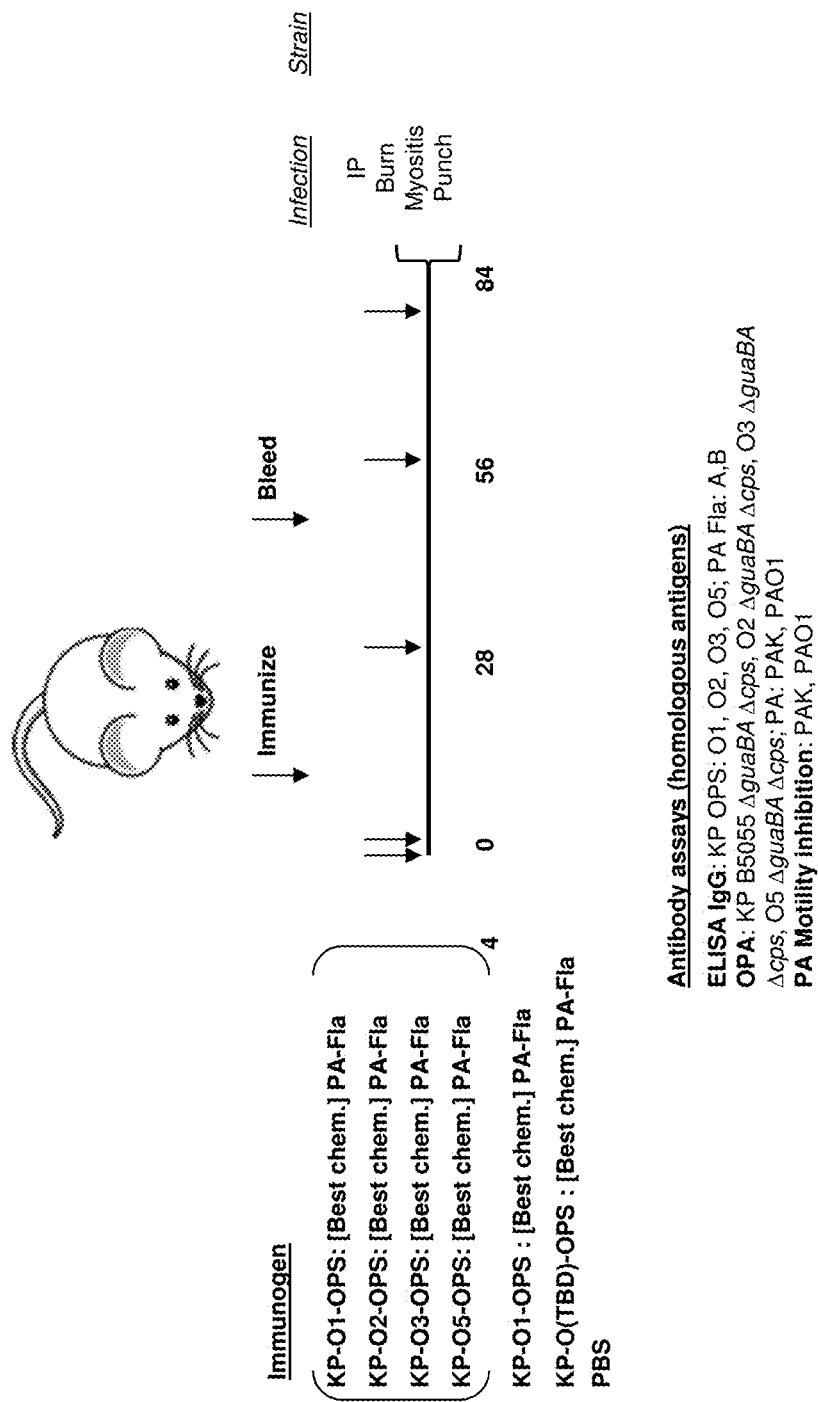

An assay will be conducted to confirm that the humoral responses and protective efficacy of the 4 down-selected monovalent COPS and flagellin conjugate vaccine components are maintained when administered as a multivalent vaccine formulation. Mice (n=240/group) will be immunized 3 times at 28 day intervals with PBS or the quadrivalent formulation, or 2 individual monovalent conjugates (n=120/group)(FIG. 24). For monovalent conjugates, we will include a KP O1 conjugate for comparison with previous proof-of-concept wound protection results, the second selected conjugate will be of a different OPS type and flagellin type, and will confirm the general protective efficacy against wound infections for monovalent and quadrivalent KP-OPS:PA-Fla conjugates. Sera obtained prior to immunization and 21 days after the final dose will be assessed for anti-LPS and anti-flagellin antibodies. We will also assess functional opsonophagocytic titers as well as inhibition of PA motility with homologous antigen pathogens. The protective efficacy of quadrivalent-relative to monovalent-vaccines to prevent invasive and wound infections will be determined using the IP, myositis, burn wound or punch-biopsy models and homologous KP O-type pathogens (n=15/group) or the homologous flagellin type expressing PA (PAK or PAO1) (n=15/group)(FIG. 24).

Figure 25:
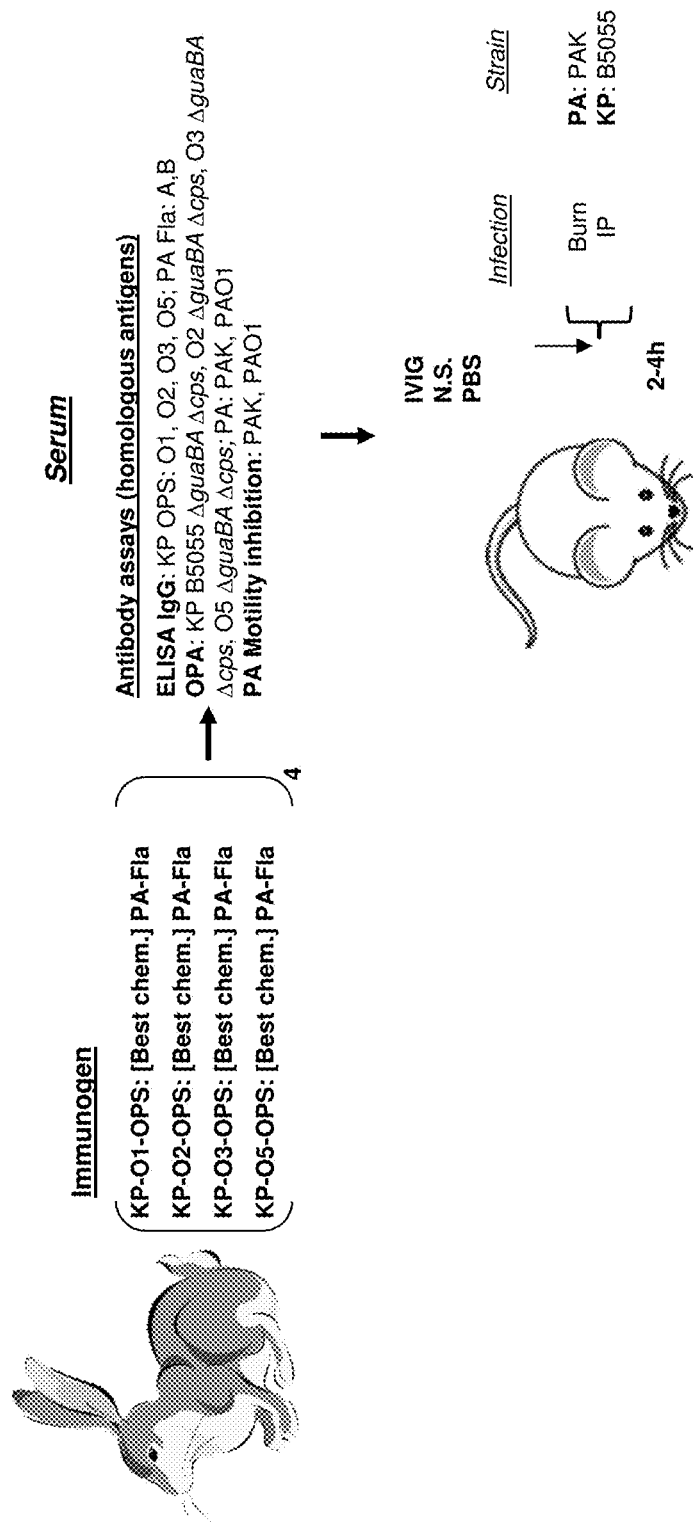

We will assess the utility of the quadrivalent conjugate formulation to generate antibody preparations that can be used therapeutically as IVIG. For this, rabbits will be hyper-immunized with quadrivalent vaccine and pooled sera will be prepared for use in passive transfer studies in mice. The level of anti-LPS and anti-flagellin IgG in rabbit sera will be determined by ELISA, as well as functional antibody titers by OPA and motility inhibition assays. Dosage levels will be approximated to the antibody titer induced by active immunization in mice. Naïve mice (n=30/group) will be intravenously administered immune sera, normal (unimmunized) rabbit sera (N.S.), or PBS, followed by IP or burn infection 2-4 hours later with KP B5055 or PA PAK, respectively (FIG. 25).

Construction of Conjugate Vaccines—

Random linked lattice-type conjugates will be generated as described (Simon R, *Infect Immun.* 2011; 79(10):4240-4249; Shafer D E et al., *Vaccine.* 2000; 18(13):1273-1281; Lees A et al., *Vaccine.* 1996; 14(3):190-198) with direct conjugation to protein lysines by activation of COPS with CDAP, and reacting with an equal ratio by weight of flagellin protein at pH 9-10. End-linked sun-type conjugates will be prepared with thioether oxime chemistry (Lees A et al., *Vaccine.* 2006; 24(6):716-729; Kubler-Kielb J., *Methods Mol Biol.* 2011; 751:317-327) by derivatizing the COPS KDO reducing end carbonyl group with a diaminoooxy cysteamine linker and reacting at a two-fold polysaccharide to protein weight with sulfo-GMBS attached at flagellin protein lysines. Conjugation will be confirmed by SDS-PAGE with Coomassie (Thermo) staining for protein and Pro-Q (Life Technologies) staining for polysaccharide, and by HPLC-SEC for size. Unreacted conjugation chemicals and conjugate components will be removed as described by size-exclusion chromatography with SUPERDEX 200 (GE) and anion exchange membrane chromatography (Sartorius) (Simon R, *Infect Immun.* 2011; 79(10):4240-4249). Final levels of polysaccharide and protein in conjugates will be determined by resorcinol assay (Monsigny M et al., *Anal Biochem.* 1988; 175(2):525-530) and BCA assay (Thermo) respectively, with unconjugated standards. Conjugates will be stored at 4° C. in 20 mM Tris pH 7 until use. We will confirm loss of TLR5 activity using the IL-8 release assay as described (Turley C B et al., *Vaccine.* 2011; 29(32):5145-5152; Taylor D N et al., *Vaccine.* 2011; 29(31):4897-4902; Liu G et al., *PLoS One.* 2011; 6(6):e20928; Song L et al., *Vaccine.* 2009; 27(42):5875-5884).

Immunization and Serological Measurements—

Six- to 8-week-old female outbred (CD-1/ICR) mice will be immunized intramuscularly on three occasions at 28 day intervals with either PBS, 2.5 µg of unconjugated flagellin or OPS, 2.5 µg by polysaccharide weight for monovalent conjugates, or 10 µs of total polysaccharide in a quadrivalent conjugate formulation. Sera will be obtained via the retroorbital plexus. Anti-flagellin and anti-OPS serum IgG titers will be assessed by ELISA as described (Simon R, *Infect Immun.* 2011; 79(10):4240-4249).

Construction of Mouse Virulent Challenge Strains—

*K. pneumoniae* O1:K2 strains are highly virulent for mice but most other serotypes, that are human pathogens, have been found to be avirulent in mice. In fact, virulence in mice is attributed to the K2 capsule. Kabha et al. (Kabha K et al., *Infect Immun*. 1995; 63(3):847-852) have shown that when the cps genes that encode the K2 capsule are cloned into an avirulent KP strain, the recombinant strain shows increased virulence for mice, albeit at a level intermediate between the fully virulent and avirulent strains. First, we will determine the virulence for our O2, O3 and O5 strains in mice by the intraperitoneal route, as this is a good test for invasive pathogenicity. If we find an $LD_{50}<10^6$ CFU, we will not manipulate the strains and will use the wild-type strains in challenge experiments. If the $LD_{50}$ is $>10^6$ CFU, we will clone the cps gene cluster that encodes K2 capsule into the putative avirulent O2, O3 and O5 strains and confirm pathogenicity in mice. We will confirm successful genetic engineering by PCR and sequencing, and the expected phenotype by western blot using polyclonal K2 antisera (Cryz S J, Jr., *J Infect Dis.* 1991; 163(5):1055-1061). For PA, we will use the well characterized PAK (FlaA) and PA:O1 (FlaB) that are pathogenic in mice.

Preparation of Bacteria for Functional Antibody Assays and Challenge Experiments—

For challenge experiments, bacteria will be prepared as described in the art (Cryz S J et al., *J Lab Clin Med.* 1986; 108(3):182-189). Bacteria are streaked on agar for single colony isolation to ensure purity. Three to 5 colonies are inoculated into rich media liquid broth and grown to mid-log phase under shaking aeration conditions at 37° C. Bacterial cultures are then pelleted, washed in PBS and adjusted to 0.3 $OD_{600}$ that we have previously determined represents approximately $1\times10^8$ CFU/ml. For OPA assays and motility assays, and challenge experiments with PA, we will use the established PAK and PAO1 strains. Expression of CPS when KP are grown in broth culture has been demonstrated as growth-phase dependent (Favre-Bonte S, *Infect Immun.* 1999; 67(2):554-561; Mengistu Y et al., *J Appl Bacteriol.* 1994; 76(5):424-430), and different CPS types may display different levels of cell coverage in broth cultures. To enable easier handling of KP, and to better standardize OPS accessibility for functional OPA assays designed to down-select conjugates, we will use the KP ΔguaBA Δcps O1, O2, O3 and O5 strains as target strains. These recombinant strains will be safer to handle from an occupational health and safety stand-point and will lack the mucoid nature of the wild-type strains. For challenge experiments, we will use wild-type capsulated strains. For all challenge strains to be used in animal experiments, in order to attain 100% attack rate in controls, we will independently determine the $LD_{50}$ for each route of infection, and base our challenge dose on the required multiple of $LD_{50}$ necessary to attain an $LD_{100}$.

Opsonophagocytic Assays.

In order to measure enhancement of bacterial uptake, a flow cytometric assay is instituted. Briefly, human PMNs are mixed with a GFP-expressing target bacterial strain in the presence or absence of antibody. The bacteria are spun onto the PMNs at 4° C., incubated for 15 min at 37° C., washed again and resuspended in medium containing gentamicin (50 μg/ml) for 15 min, washed and then resuspended in PBS for flow cytometric analysis with gating on the PMNs by forward and side scatter. The uptake of the GFP-labelled bacteria is then determined. Either GFP-expressing PA or KP is added to the PMNs in the presence and absence of pre- and post-immune mouse sera from each of the conjugate vaccines. As a positive control, PMNs and bacteria are mixed with WIG enriched in antibodies to PA and KP as we previously described (Ramachandran G et al., *J Infect Dis.* 2013; 207(12):1869-1877). As further controls, the PMNs and bacteria are incubated at 4° C. that will inhibit bacterial uptake. Mixtures are incubated at 37° C. for 30 min, washed 3 times and analyzed by flow cytometry in the Flow Cytometry Core at the CVD. The uptake and killing measured by this high throughput system will be confirmed in a HL-60 cell assay using live colony counts. Opsonophagocytic killing will be evaluated using the pneumococcal OPA assay that is accepted by the FDA. 20 μl (~700-1000 CFU) of KP or PA grown to log phase are combined with two-fold serial dilutions of serum and incubate at 37° C. for 15 min in a 5% $CO_2$ incubator to allow the antibody to opsonize the bacteria. Then, 10 μl of BRC and 40 μl of differentiated HL-60 cells are added ($4\times10^5$ cells/well) and incubated at 37° C. for 45 min. The negative control contains bacteria, HL-60 cells and complement only. OPA titer is defined as the reciprocal of the highest serum dilution that produced >50% killing in relation to the killing observed for control containing only bacteria, HL-60 cells and complement (no serum).

Motility Inhibition Assays—

The ability of conjugate vaccine antisera to block motility of PA expressing Type A and B flagella is determined. As described by Brett et al (Brett P J et al., *Infect Immun.* 1994; 62(5):1914-1919), two-fold dilutions of antisera with motility medium are mixed and the agar is allowed to set. Motility assays are performed by stabbing the agar with PA and incubating overnight. The zone of motility is measured the next day.

Hyper-Immunization of Rabbits to Obtain WIG—

New Zealand White rabbits (n=2/group) are immunized intramuscularly 4 times at 2-week intervals with the quadrivalent conjugate containing 10 μg total polysaccharide. One control rabbit is immunized with four doses of PBS to obtain normal rabbit serum. Pooled sera taken 28 days after the last immunization is assessed for titers of anti-COPS and anti-Fla IgG by end-point dilution ELISA with purified antigens and functional antibody with OPA and motility inhibition assays. Sera is heat inactivated prior to use in functional assays and passive transfer, to ablate potential serum bactericidal killing by rabbit complement.

Passive Transfer Immunization—

For passive transfer protection assays, mice are administered 0.2 ml heat-inactivated rabbit sera intravenously by the tail vein at the approximate total EU/mouse obtained with active immunization, and infected 2-4 hours later with a lethal dose of KP or PA.

Mouse Peritonitis Challenge—

Mice are infected IP with either PA or KP (at the minimal reliable $LD_{100}$) and weight and survival (or moribundity) is followed for 14 days.

Mouse Myositis Infection—

The mouse thigh muscle infection model has been used extensively to assess antimicrobial agents (Fantin B et al., *Antimicrob Agents Chemother.* 1991; 35(7):1413-1422). Following immunization at days 0, 14 and 28 with either monovalent vaccine or PBS, mice are administered an $LD_{100}$ dose of KP or PA suspended in 100 μl of PBS into the thigh muscle of the mouse and weight and survival (or moribundity) followed for 14 days.

Burned Mouse Model—

Under anesthesia and analgesia, mice are subjected to a nonlethal thermal injury with the burned mouse model described (Cryz S J, Jr., *Infect Immun.* 1984; 45(1):139-142; Stieritz D D, Holder I A. *J Infect Dis.* 1975; 131(6):688-691; Neely A N et al., *J Burn Care Rehabil.* 2002; 23(5):333-340;

Horzempa J et al., Clin Vaccine Immunol. 2008; 15(4):590-597). A heat-resistant polymer card template with a 1 by 1.5 inch opening is pressed firmly against the shaven back. Ethanol is evenly spread over the area of the back outlined by the window, ignited with a lit cotton swab, and allowed to burn for precisely 10 seconds and extinguished. Immediately after the burn, the mice are given 0.5 ml of sterile normal saline intraperitoneally as fluid replacement therapy. This method reproducibly yields a 12-15% total body surface area full-thickness burn which, by itself, is nonlethal. Burned mice are challenged with a subeschar $LD_{100}$ injection of either PA or KP. Mice are observed daily for 14 days during which time morbidity and mortality will be recorded. As controls, a separate "bystander group" is included, that will include burned but uninfected mice inoculated with saline alone.

Mouse Punch-Biopsy Model—

Mice are anesthetized by intraperitoneal injection of 100-150 µl of ketamine (100 mg/kg)/xylazine (10 mg/kg) prior to performing a dermal wounding procedure. After anesthesia, the dorsum of the mouse is shaved with an electric razor. The surgery area is sterilized with iodine and 70% alcohol. A full-thickness, excisional dermal wound is made on the back of each mouse with a 6 mm sterile biopsy punch, and a $LD_{100}$ bacterial dose in 25 µl will be inoculated on the wound site. Other groups of mice are wounded, but not inoculated with bacteria, and serve as negative controls. Wounded mice are observed for 7 days, monitoring for mortality and moribundity. As alternative endpoints prior to mortality, mice are evaluated for wound size, gross pathology, weight, and colonization by excising a 2-4 mm tissue punch biopsy from the wound bed to determine CFU/g. All challenge experiments are conducted without the use of an immunosuppressive agent, as we presume functional activity of professional phagocytes to be a key mechanism of vaccine-mediated protection.

Statistical Power—

A titer of ≥4-fold over pre-immune levels for ELISA and OPA assays, or ≥50% reduction in PA motility zone, will be assigned as the threshold for seroconversion. For comparison of seroconversion rates between monovalent vaccines, if the true underlying rate one type of conjugate achieves is 85% or greater, with 30 mice/group we will have 94% power to detect a significant difference, if seroconversion in mice getting the other type of conjugate is 40% or less (Fisher's exact test, α=0.025, 1 tail). Power will be 49% if the seroconversion rate in mice getting the other type of conjugate is 60%. For comparisons of monovalent and quadrivalent formulations, if the true seroconversion rate is 80% for each formulation, with 60 mice per group, we will have 77% power to find non-inferiority using a non-inferiority margin of 20% (i.e., to obtain a 2-sided 95% confidence interval, by a likelihood score method, for the absolute difference of monovalent-quadrivalent with upper limit≤20%). Challenging with an $LD_{100}$ of wild-type KP or PA is expected to cause 100% mortality in unimmunized mice. Thus, if mortality for a conjugate vaccine is reduced by 50% or greater, with 15 mice/group we will have 94% power to detect a significant difference (Fisher's exact test, α=0.025, 1 tail). If mortality is 10% for one vaccine and 70% for another vaccine, with 15 mice/group, we will have 89% power to find a significant difference between conjugates (Fisher's exact test, α=0.025, 1 tail). If mortality is 20% for one vaccine and 70% for the other vaccine, we will have 74% power to find a significant difference. If the true mortality rate is 10% for both monovalent and quadrivalent vaccines, with 15 mice/group we will have 69% power to show non-inferiority of the quadrivalent formulation using a non-inferiority margin of 30% (absolute difference), based on a 2-sided 95% confidence interval calculated by a likelihood score method.

Expected Result—:

It is likely that at least a single monovalent conjugate will be identified that induces high IgG titers with functional anti-bacterial properties by both the flagellin carrier protein and OPS hapten, and will protect against wound infections with homologous antigen expressing KP and PA pathogens. We anticipate that 3 doses may be required to attain significant anti-OPS IgG levels. It is a possibility as well that equivalent immunogenicity and protection will be seen between several OPS specific conjugate types in our monovalent panel. If this occurs, our basis for down-selection will be for regulatory and manufacturing considerations. We also expect that a quadrivalent mixture will recapitulate the humoral responses seen for monovalent conjugates alone. Protection is presumed to be mediated by antibodies. Hence we further anticipate that passive transfer immunization with polyclonal KP-OPS:PA-Fla vaccine elicited sera will protect against KP and PA.

Measuring Protection in Wound Models in Pigs Using Optimized Conjugate Vaccine Formulations—

The integumentary system of pigs is understood as the best approximate of human skin, exhibiting similar architecture and structural properties (Sullivan T P et al., Wound Repair Regen. 2001; 9(2):66-76). Accordingly, the quadrivalent vaccine formulation developed in mice, is tested in a porcine full-thickness wound model.

Figure 26:
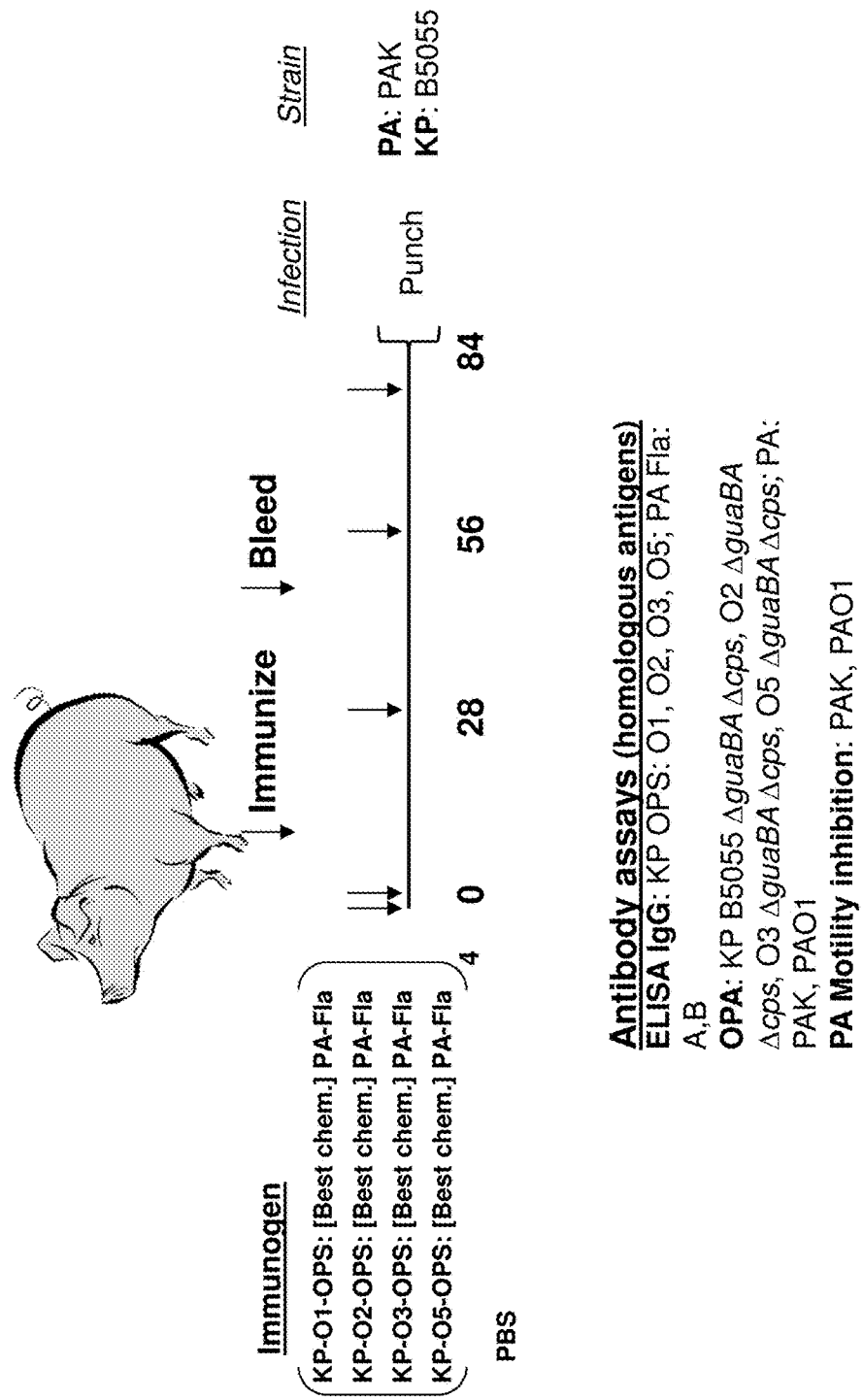

The 50% effective dose ($ED_{50}$) for various doses of KP B5055 O1:K2 and PA PAK are determined by infecting at various doses at multiple wound sites in naïve pigs. Once a reliable infectious dose is determined, 4 pigs 3 times are immunized with PBS or quadrivalent conjugate containing 25 µs of total polysaccharide, as this approximate COPS dose was used successfully in human clinical trials for Shigella (Passwell J H, Infect Immun. 2001; 69(3):1351-1357; Cohen D, Infect Immun. 1996; 64(10):4074-4077), S. Paratyphi A (Konadu E Y, Infect Immun. 2000; 68(3):1529-1534), and E. coli (Ahmed A et al., J Infect Dis. 2006; 193(4):515-521) COPS conjugates. As controls, 2 pigs are mock immunized with PBS alone. Twenty-one days after the final dose, immunized (2/individual pathogen) or control pigs (1/individual pathogen) are infected at multiple sites with moderate or high levels of KP B5055 of PA PAK (FIG. 26). Wounds sites will be isolated from each other, and can be considered as independent.

Immunization and Serological Measurements—

Thirty to 35 kg female Yorkshire pigs are immunized intramuscularly on 3 occasions at 28 day intervals as indicated. Sera is obtained before immunization and 21 days after the last dose. Anti-flagellin and anti-OPS serum IgG titers are assessed by ELISA, and functional antibodies are measured by OPA and motility inhibition assays as described for Aim 2.

Porcine Model of KP and PA Wound Infection—

A full dermal punch biopsy is used to generate a full thickness wound (beyond 0.7 mm) that passes completely through the first layer of fat cells on the pig. Each animal receives up to 48 wounds (3 groups of 16) using a 12 mm biopsy punch, along the back in the lumbar and thoracic area with each wound separated by approximately 15 mm of normal skin. Animals are inoculated with a high or low dose of KP or PA and within 10 minutes of inoculation, all wounds will be covered with a dressing. At 1, 4, and 10 days post-infection, the dressings are removed, and 6 wounds per animal will be analyzed for culture or biopsy. For each wound, two types of biopsies are performed. For CFU/g tissue, a 6 mm punch biopsy are obtained. For pathology, a sterile scalpel is used to obtain a full thickness wedge biopsy. Additional biopsies may be taken based on previous culture results or wound appearance as appropriate. A similar biopsy on each collection day will be saved for scanning electron microscopy (SEM) evaluation of biofilm. Endpoint parameters will include wound size, CFU/g, clinical scores, biofilm formation, and histopathology to evaluate wound bed healing and re-epithelialization.

Statistical Power—

Each wound is an independent observation. With 2 immunized animals and 1 control animal for either KP or PA, we will have 6 and 3 total independent wounds, respectively, by which to measure pathology or burden for a particular dose of KP or PA. We will have 86% power to find statistical significance, if the difference between the CFU/g means for immunized relative to unimmunized pigs is 2.5 times the standard deviation, which is assumed to be the same for both groups of pigs (2-sample t-test, $\alpha=0.05$, 2-sided).

Expected Results—:

We anticipate that 3 doses of quadrivalent conjugate in pigs will induce 100% seroconversion for all vaccine components. Whereas our endpoint in mouse experiments is protection from mortality, the endpoint in pigs will be wound healing. Bacteremia and ascending infections are the major complication of PA and KP wound infections, and protection against systemic spread is the primary target of our vaccine. Nevertheless, we anticipate that antibodies towards KP OPS and PA Fla could reduce overall tissue CFU/g through enhanced OPA by fixed tissue macrophages and interference with biofilm formation. Hence, faster wound recovery, improved tissue pathology and lower bacterial burden are expected to be found.

While there have been shown and described what are presently believed to be the preferred embodiments of the present invention, those skilled in the art will realize that other and further embodiments can be made without departing from the spirit and scope of the invention described in this application, and this application includes all such modifications that are within the intended scope of the claims set forth herein. All patents and publications mentioned and/or cited herein are incorporated by reference to the same extent as if each individual publication was specifically and individually indicated as having been incorporated by reference in its entirety.

What is claimed is:

1. A conjugate comprising a *Klebsiella pneumoniae* surface polysaccharide antigen and a *Pseudomonas aeruginosa* flagellin protein or antigenic fragment thereof, wherein the conjugate comprises i) *Pseudomonas aeruginosa* flagellin type A (FlaA) or an antigenic fragment thereof and/or *Pseudomonas aeruginosa* flagellin type B (FlaB) or an antigenic fragment thereof and ii) OPS from *Klebsiella pneumoniae* selected from the group consisting of *Klebsiella pneumoniae* serovars O1, O2a, O3, O5.

2. The conjugate of claim 1, wherein the surface polysaccharide antigen and the flagellin are covalently linked.

3. The conjugate of claim 1, wherein *Pseudomonas flagellin* is covalently linked to one or more OPS from a single *Klebsiella pneumoniae* serovar type.

4. The conjugate of claim 1, wherein the *Pseudomonas aeruginosa* flagellin type A (FlaA) comprises SEQ ID NO: 1.

5. The conjugate of claim 1, wherein the *Pseudomonas aeruginosa* flagellin type B (FlaB) comprises SEQ ID NO: 2.

6. A vaccine composition comprising one or more conjugates of claim 1.

7. The vaccine composition of claim 6, wherein the composition is a multivalent conjugate vaccine comprising one or more *Pseudomonas flagellins* covalently linked to one or more *Klebsiella* O polysaccharides (OPS).

8. The vaccine composition of claim 6, wherein the conjugate vaccine is a multivalent conjugate vaccine comprising two different *Pseudomonas flagellin* or an antigenic fragment thereof covalently linked to one or more *Klebsiella* O polysaccharides (OPS).

9. The vaccine composition of claim 8, wherein the multivalent conjugate vaccine comprises four different OPS antigens from *Klebsiella pneumoniae* serovars O1, O2a, O3, and O5.

10. A method of making the conjugate of claim 1, comprising covalently bonding a *Klebsiella pneumoniae* surface polysaccharide antigen and a *Pseudomonas aeruginosa* flagellin protein or an antigenic fragment thereof.

11. The method of claim 10, wherein the *Klebsiella pneumoniae* has an attenuating mutation in the guaBA locus and a mutation in the wza-wzc locus.

* * * * *